(12) United States Patent
de Menezes et al.

(10) Patent No.: US 12,017,984 B2
(45) Date of Patent: Jun. 25, 2024

(54) PROPANE/BUTANE DEHYDROGENATION COMPLEX WITH THERMAL OXIDATION SYSTEM

(71) Applicant: Honeywell International Inc., Charlotte, NC (US)

(72) Inventors: Rui de Menezes, Goa (GB); Jan De Ren, Bracknell (GB); Tom Jackson, Surrey (GB); Madan K. M. Desai, Surrey (GB); Adam J. Kanyuh, Streamwood, IL (US)

(73) Assignee: Honeywell International Inc., Charlotte, NC (US)

(*) Notice: Subject to any disclaimer, the term of this patent is extended or adjusted under 35 U.S.C. 154(b) by 103 days.

(21) Appl. No.: 17/362,378

(22) Filed: Jun. 29, 2021

(65) Prior Publication Data

US 2022/0041529 A1    Feb. 10, 2022

Related U.S. Application Data

(60) Provisional application No. 63/170,787, filed on Apr. 5, 2021, provisional application No. 63/060,884, filed on Aug. 4, 2020.

(51) Int. Cl.
*C07C 5/333* (2006.01)
*B01D 53/02* (2006.01)
(Continued)

(52) U.S. Cl.
CPC .............. *C07C 5/333* (2013.01); *B01D 53/02* (2013.01); *B01D 53/343* (2013.01); *B01D 53/50* (2013.01);
(Continued)

(58) Field of Classification Search
None
See application file for complete search history.

(56) References Cited

U.S. PATENT DOCUMENTS

| 3,567,433 | A |  | 3/1971 | Gutnikov |
| 3,963,611 | A | * | 6/1976 | Dardenne-Ankringa, Jr. .............. C02F 11/08 423/544 |

(Continued)

FOREIGN PATENT DOCUMENTS

| CA | 2706957 A1 | 6/2009 |
| CN | 101239758 A | 8/2008 |

(Continued)

OTHER PUBLICATIONS

International Search Report from corresponding PCT application No. PCT/US2021/071070 dated Nov. 3, 2021.
(Continued)

*Primary Examiner* — Youngsul Jeong
*Assistant Examiner* — Alyssa L Cepluch

(57) ABSTRACT

A process for the treatment of sulfidic spent caustic, conditioned catalyst regeneration vent gas, C4 isomerization off gas, various and hydrocarbon containing liquid and gaseous streams in addition to toxic containing streams like cyanidic off gas and waste water in a propane/butane dehydrogenation complex is described. Various effluent streams are combined in appropriate collection vessels, including an off-gas knockout drum, a hydrocarbon buffer vessel, a spent caustic buffer vessel, an optional a waste water buffer vessel, and a fuel gas knockout drum. Streams from these vessels are sent to a thermal oxidation system.

20 Claims, 23 Drawing Sheets

(51) Int. Cl.
  *B01D 53/34* (2006.01)
  *B01D 53/50* (2006.01)
  *B01D 53/68* (2006.01)
  *B01D 53/96* (2006.01)
  *C02F 1/72* (2023.01)
  *C07C 7/12* (2006.01)
  *C07C 7/148* (2006.01)
  *C10G 67/06* (2006.01)
  *C10G 67/12* (2006.01)

(52) U.S. Cl.
  CPC ............. *B01D 53/68* (2013.01); *B01D 53/96* (2013.01); *C07C 7/12* (2013.01); *C07C 7/14816* (2013.01); *C10G 67/06* (2013.01); *C10G 67/12* (2013.01); *B01D 2257/2025* (2013.01); *B01D 2257/2045* (2013.01); *B01D 2257/302* (2013.01); *B01D 2258/0283* (2013.01); *B01D 2259/40083* (2013.01); *B01D 2259/416* (2013.01); *C02F 1/72* (2013.01)

(56) References Cited

U.S. PATENT DOCUMENTS

| | | | |
|---|---|---|---|
| 4,377,470 A | 3/1983 | Hettinger, Jr. et al. | |
| 4,430,517 A | 2/1984 | Imai et al. | |
| 4,514,368 A | 4/1985 | Hubred | |
| 4,544,533 A | 10/1985 | Marcantonio | |
| 4,762,812 A | 8/1988 | Lopez et al. | |
| 5,339,755 A | 8/1994 | Smith | |
| 5,365,010 A | 11/1994 | Rao et al. | |
| 6,449,954 B2 | 9/2002 | Bachmann | |
| 6,514,904 B1 | 2/2003 | Moser et al. | |
| 7,002,048 B2 | 2/2006 | Wijesekera et al. | |
| 7,034,192 B2 | 4/2006 | Wijesekera | |
| 7,126,029 B2 | 10/2006 | Skipworth et al. | |
| 7,141,700 B1 | 11/2006 | Schmidt et al. | |
| 7,141,701 B1 | 11/2006 | Schmidt et al. | |
| 7,166,752 B2 | 1/2007 | Marshall, Jr. et al. | |
| 7,186,866 B1 | 3/2007 | Keenan et al. | |
| 7,417,003 B2 | 8/2008 | Schmidt et al. | |
| 7,674,739 B2 | 3/2010 | Elomari et al. | |
| 7,652,181 B1 | 4/2010 | Schmidt et al. | |
| 7,700,511 B2 | 4/2010 | Reynolds et al. | |
| 7,740,751 B2 | 6/2010 | Peters | |
| 7,744,828 B2 | 6/2010 | Schmidt et al. | |
| 7,841,807 B2 | 11/2010 | Naunheimer et al. | |
| 7,878,736 B2 | 2/2011 | Naunheimer et al. | |
| 7,888,537 B2 | 2/2011 | Schmidt et al. | |
| 8,242,320 B2 | 8/2012 | Schmidt et al. | |
| 8,329,603 B2 | 12/2012 | Randolph et al. | |
| 8,387,645 B2 | 3/2013 | Shafe | |
| 8,457,278 B2 | 6/2013 | Fadler | |
| 8,518,847 B2 | 8/2013 | Jan et al. | |
| 8,608,941 B2 | 12/2013 | Haizmann et al. | |
| 8,609,915 B2 | 12/2013 | Majumdere et al. | |
| 8,609,916 B2 | 12/2013 | Majumder et al. | |
| 8,679,321 B2 | 3/2014 | Negiz et al. | |
| 8,734,648 B2 | 5/2014 | Kumfer et al. | |
| 8,853,481 B2 | 10/2014 | Jan et al. | |
| 9,006,123 B2 | 4/2015 | Nabozny | |
| 9,079,816 B2 | 7/2015 | Johnson et al. | |
| 9,138,738 B1 | 9/2015 | Glover et al. | |
| 9,150,469 B2 | 10/2015 | Bullen et al. | |
| 9,181,150 B1 | 11/2015 | Smith et al. | |
| 9,206,362 B2 | 12/2015 | Haizmann et al. | |
| 9,290,826 B2 | 3/2016 | Da Costa et al. | |
| 9,302,951 B2 | 4/2016 | Stevens et al. | |
| 9,321,783 B2 | 4/2016 | Ibert et al. | |
| 9,327,259 B2 | 5/2016 | Hartman et al. | |
| 9,328,037 B2 | 5/2016 | Riley et al. | |
| 9,359,917 B2 | 6/2016 | Koseoglu et al. | |
| 9,360,252 B2 | 6/2016 | Furlong et al. | |
| 9,399,604 B2 | 7/2016 | Martins et al. | |
| 9,416,321 B2 | 8/2016 | Eizenga et al. | |
| 9,469,818 B2 | 10/2016 | Baldriaghi et al. | |
| 9,523,050 B2 | 12/2016 | Pandranki et al. | |
| 9,567,264 B2 | 2/2017 | Fichtl | |
| 9,637,699 B2 | 5/2017 | Ellig et al. | |
| 9,718,047 B2 | 8/2017 | Moser et al. | |
| 9,745,523 B2 | 8/2017 | Ganguly et al. | |
| 9,815,756 B2 | 11/2017 | Schmidt et al. | |
| 9,822,314 B2 | 11/2017 | Ray | |
| 9,914,675 B2 | 3/2018 | Buchbinder et al. | |
| 9,914,880 B2 | 3/2018 | Fichtl et al. | |
| 9,914,883 B2 | 3/2018 | Dutta et al. | |
| 10,041,004 B2 | 8/2018 | Govindhakannan et al. | |
| 10,240,099 B2 | 3/2019 | Mani et al. | |
| 10,384,186 B2 | 8/2019 | Egolf et al. | |
| 10,399,852 B2 | 9/2019 | De Ren et al. | |
| 10,429,066 B2 | 10/2019 | Schröter et al. | |
| 10,577,539 B2 | 3/2020 | Brodeur-Campbell et al. | |
| 10,577,547 B2 | 3/2020 | Wexler et al. | |
| 2004/0040761 A1 | 3/2004 | Duesel, Jr. et al. | |
| 2013/0087481 A1 | 4/2013 | Heraud et al. | |
| 2015/0094486 A1 | 4/2015 | Buchbinder et al. | |
| 2016/0168054 A1 | 6/2016 | Kalnes et al. | |
| 2016/0346761 A1* | 12/2016 | Kanazirev | B01D 53/261 |
| 2019/0144766 A1 | 5/2019 | Yokomizo et al. | |
| 2019/0225563 A1 | 7/2019 | Pretz | |
| 2019/0292949 A1 | 9/2019 | Sonnek et al. | |
| 2020/0222851 A1 | 7/2020 | De Ren et al. | |

FOREIGN PATENT DOCUMENTS

| | | |
|---|---|---|
| CN | 109939550 A | 6/2019 |
| EP | 0320094 A2 | 6/1989 |
| EP | 1218890 A2 | 7/2002 |
| WO | 2016195995 A1 | 12/2016 |

OTHER PUBLICATIONS

Written Opinion from corresponding PCT application No. PCT/US2021/071070 dated Nov. 3, 2021.

Levy, Edward et al., Recovery of Water from Boiler Flue Gas Using Condensing Heat Exchangers, Final Technical Report issued Jun. 2011, Energy Research Center.

Liu, Xinpeng et al, Desulfurization and regeneration performance of heteropoly compound/ionic liquid solutions at high temperature, Chemical Engineering Journal 316, 2017, 171-178.

International Preliminary Report on Patentability from corresponding PCT application No. PCT/US2021/071070 dated Feb. 7, 2023.

Extended European Search Report from corresponding European patent application No. EP21853267.9, dated Apr. 26, 2024.

* cited by examiner

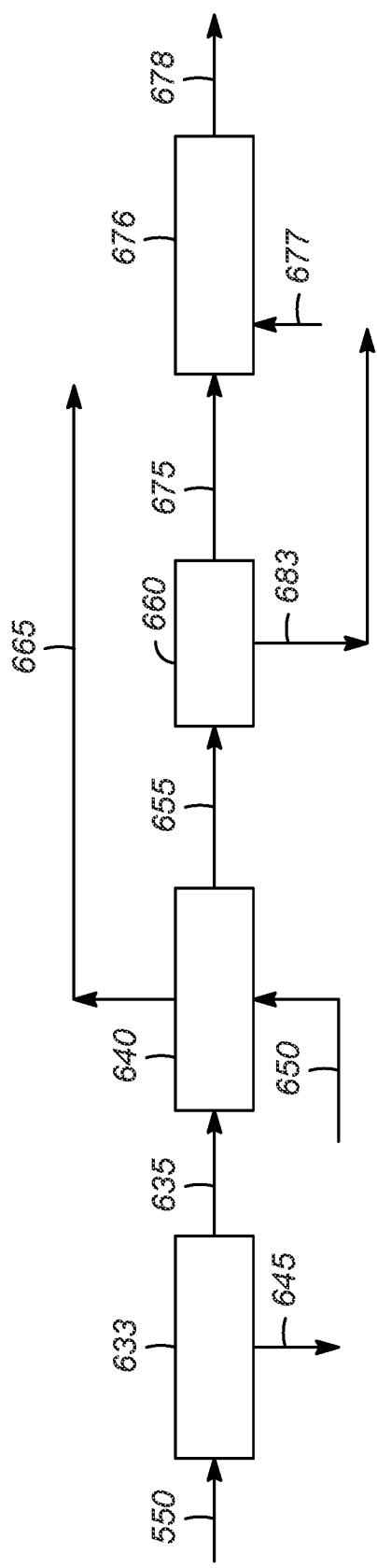
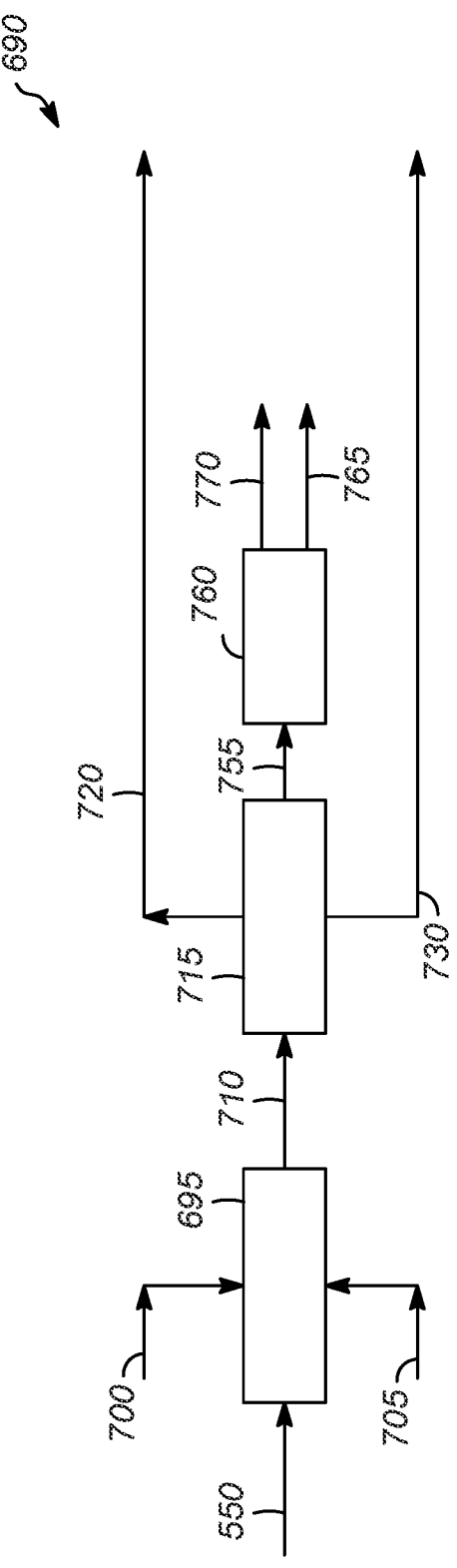
FIG. 7A
FIG. 7B

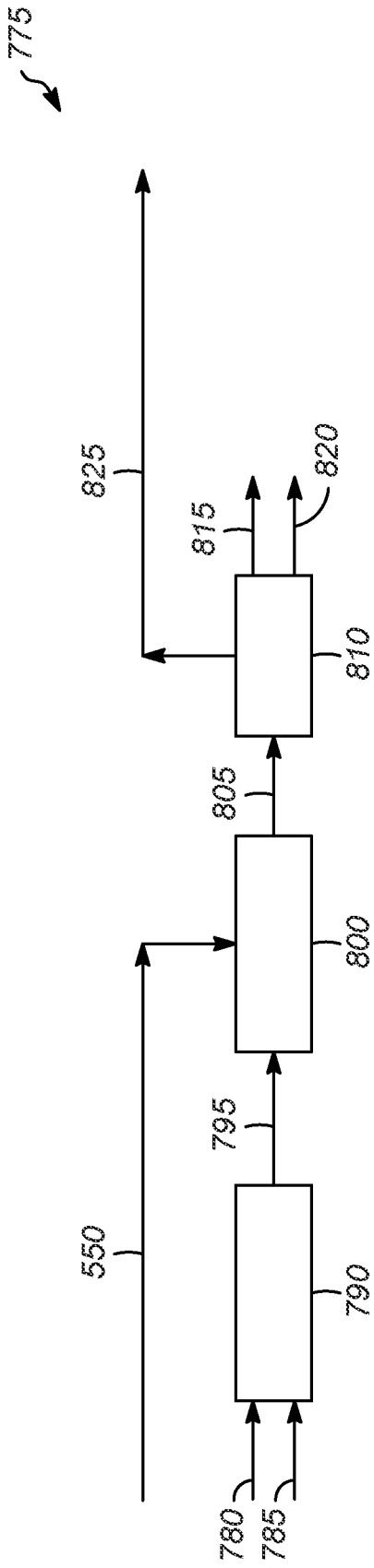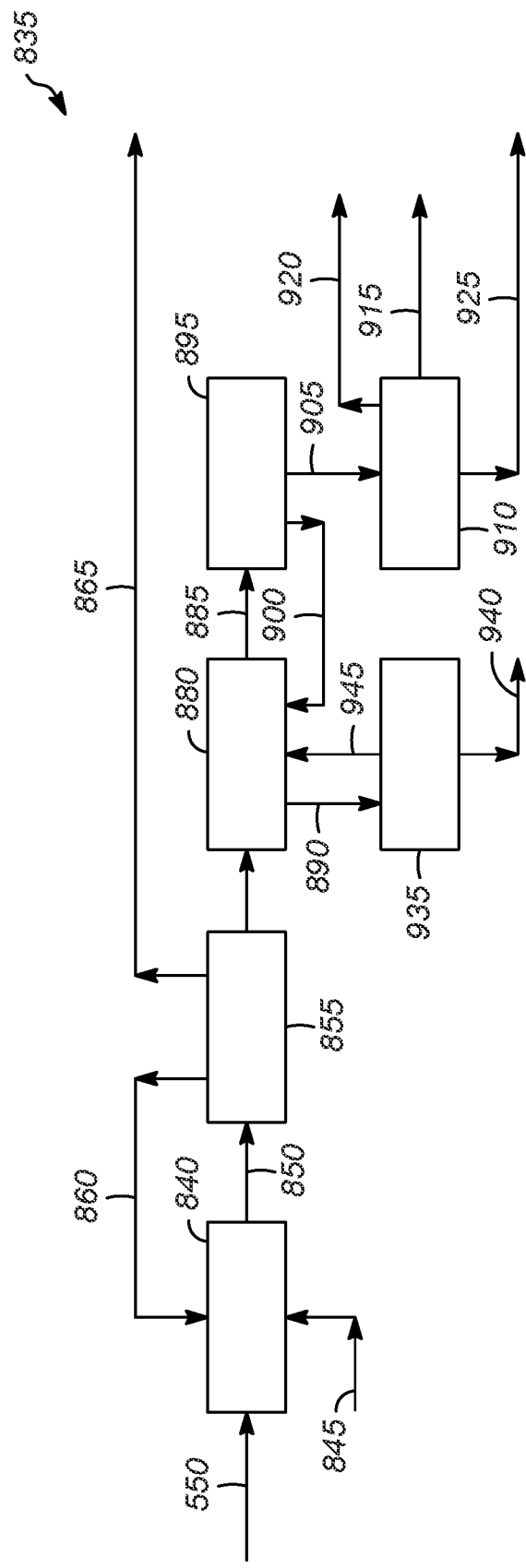

PROPANE/BUTANE DEHYDROGENATION COMPLEX WITH THERMAL OXIDATION SYSTEM

RELATED APPLICATIONS

This application claims the benefit of U.S. Provisional Patent Application Ser. Nos. 63/060,884 filed on Aug. 4, 2020, and 63/170,787 filed Apr. 5, 2021, the entirety of which are incorporated herein by reference.

BACKGROUND

The dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers, and other products which are well known to those skilled in the art. Examples of dehydrogenation include the conversion of propane to propylene and the conversion of butane to butylene. Both of these reactions have important industrial applications. Propylene is one of the world's largest produced petrochemical commodities and is used in the production of polypropylene, acrylonitrile, acrylic acid, propylene oxide, oxo-alcohols, acrolein, glycols, plasticizers, cumene, isopropyl alcohol, and acetone. Iso-butylene can be polymerized to provide tackifying agents for adhesives, viscosity-index additives for motor oils, and impact-resistant and antioxidant additives for plastics. Another example of the growing demand for iso-butylene is the production of oxygen-containing gasoline blending components.

Those skilled in the art of hydrocarbon conversion processing are well versed in the production of olefins by means of catalytic dehydrogenation of paraffinic hydrocarbons. In addition, many patents have issued which teach and discuss the dehydrogenation of hydrocarbons in general. For example, U.S. Pat. No. 4,430,517 (Imai et al) discusses a dehydrogenation process and catalyst for use therein.

Propane and butane dehydrogenation units could be located as stand-alone units, or they could be part of a larger complex with downstream derivative units and/or allied process units which producing a variety of effluent and/or emission streams requiring safe treatment and disposal meeting the requisite process and regulatory requirements. In the existing complex, often such facilities could be staggered or mutually exclusive to the individual process unit. Therefore, it would be desirable to reduce the number of pieces of equipment within the complex by integrating the treatment facilities, reducing the footprint while achieving the requisite treatment meeting the regulatory requirements for the effluent streams. Further, it would also be desirable to reduce the consumption of treatment chemicals, utilize the waste gaseous emission streams with calorific value which otherwise would have been flared achieving savings in fuel gas, treat the low volume COD/BOD (chemical oxygen demand/biological oxygen demand) bearing aqueous effluent streams. It would also be desirable to reduce the complexity of the waste streams and low value calorific containing streams processing.

BRIEF DESCRIPTION OF THE DRAWINGS

FIGS. 7A-7D are illustrations of embodiments of propylene derivative process units according to the present invention.

DETAILED DESCRIPTION

Figure 1:
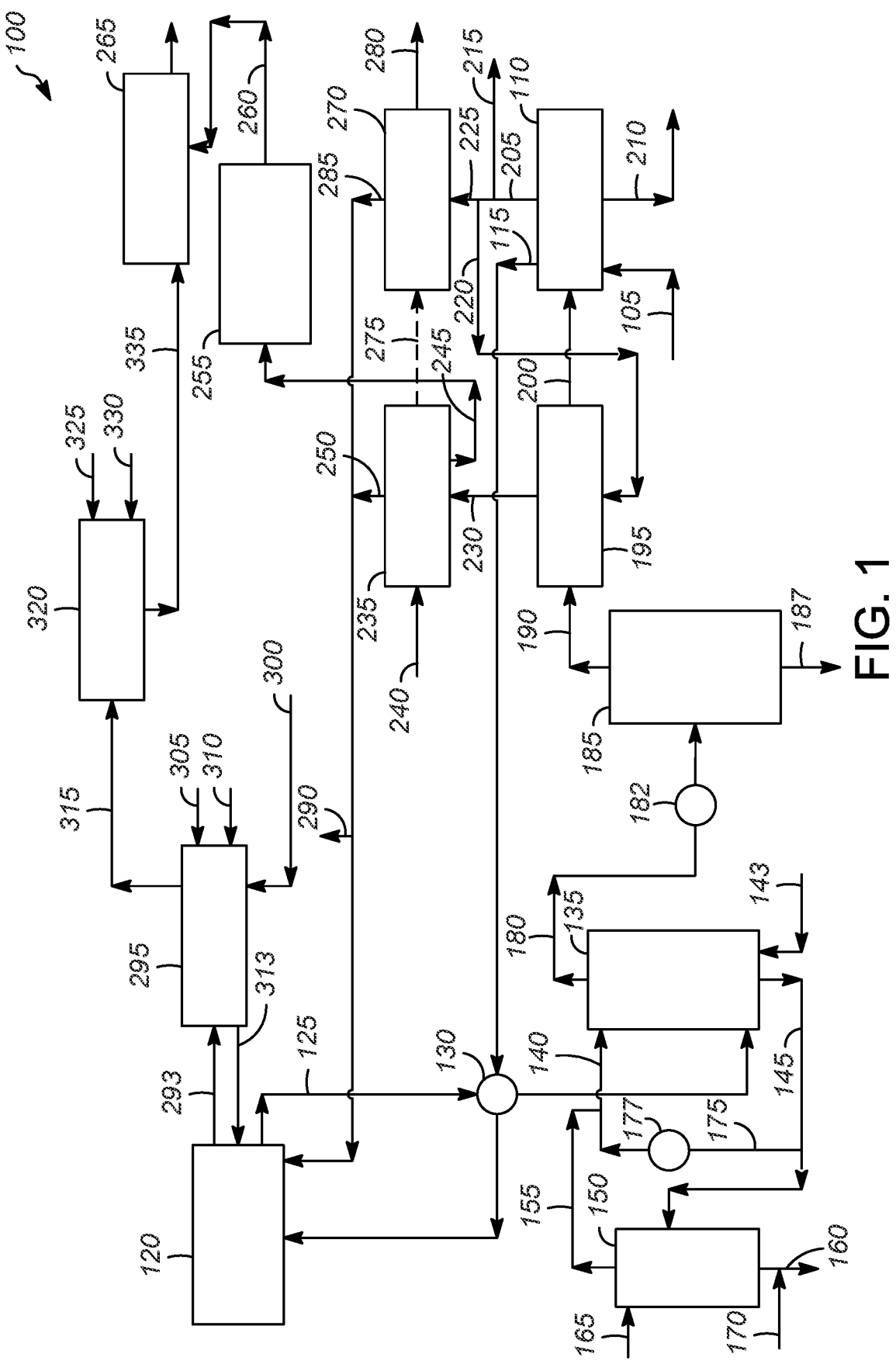
FIG. 1 is an illustration of one embodiment of a propane/butane dehydrogenation complex.

The present invention provides proper treatment of hydrocarbon containing liquid and gaseous streams in the propane and/or butane dehydrogenation complex. In some cases, the propane and/or butane dehydrogenation complex include propylene and/or iso-butylene derivative process units. Various effluent streams from different parts of the propane/butane dehydrogenation complex are combined in appropriate collection vessels, including an off-gas knockout drum, a hydrocarbon buffer vessel, a fuel gas knockout drum, a spent caustic buffer vessel, and a waste water buffer vessel. Streams from these vessels are sent to a thermal oxidation system. This allows the elimination of a number of components from the conventional process, including one or more of the spent sulfidic caustic treatment section, regeneration vent gas treatment section, butane isomerization off gas scrubber, CN destruction system and dedicated thermal oxidizing system, as well as the associated piping, instrumentation, controls, and mechanical and structural components, reducing both capital costs and operating costs. In addition, the process reduces the cost of treatment chemicals, and the size of certain streams may also be reduced.

Effluent streams are classified as low or high based on their heating value. Effluent streams can be considered to be low calorific when the stream has a heating value less than the threshold amount and classified as high calorific when the heating value exceeds the threshold. For example, the threshold heating value could be 40 BTU/SCF for gaseous effluent streams, and 2500 BTU/lb could be a threshold heating value for liquid effluent streams. The specific threshold for the division between high and low calorific value may vary. However, the division allows integration of the process based on the heating value for the stream.

One aspect of the invention is an integrated propane or butane dehydrogenation and thermal oxidation and flue gas treatment process. In one embodiment, the process comprises: dehydrogenating an alkane feed stream comprising propane, butane, or mixtures thereof in a dehydrogenation reaction zone in the presence of a dehydrogenation catalyst under dehydrogenation conditions to form a dehydrogenated product stream comprising propylene, iso-butylene, or mixtures thereof; recovering the dehydrogenated product stream; at least one of: introducing a sulfidic spent caustic stream from a regenerant gas scrubbing zone into a spent caustic buffer vessel; introducing at least one of a spent solvent stream from a solvent recovery section, and a purge stream from a solvent recovery section into a hydrocarbon buffer vessel; and thermally oxidizing at least one of a spent caustic stream from the spent caustic buffer vessel, a liquid hydrocarbon stream from the hydrocarbon buffer vessel, an off-gas stream from an off-gas knockout drum, and a fuel gas stream from a fuel gas knockout drum in a thermal oxidation system.

In some embodiments. thermally oxidizing at least one of the spent caustic stream, the liquid hydrocarbon stream, the off-gas stream, and the fuel gas stream comprises: thermally oxidizing the at least one of the spent caustic stream, the liquid hydrocarbon stream, the off-gas stream, and the fuel gas stream in a thermal oxidizing section to form a flue gas consisting essentially of at least one of $H_2O$, $Na_2CO_3$, $Na_2SO_3$, $Na_2SO_4$, $CO_2$, $N_2$, $O_2$, SOx, NOx, NaCl, HCl, $Cl_2$, dioxins, and furans; optionally recovering waste heat from the flue gas in a waste heat recovery section; removing at least one of SOx, HCl, and $Cl_2$ from the flue gas in a SOx removal section to form a de-SOx outlet flue gas consisting essentially of at least one of $H_2O$, $CO_2$, $N_2$, $O_2$, NOx, dioxins, and furans, wherein removing the at least one of SOx, HCl, and $Cl_2$ from the flue gas comprises: quenching the flue gas in a quench section to form quenched flue gas after recovering the waste heat; and contacting a caustic solution or an $NH_3$ based solution with the quenched flue gas in a SOx scrubbing section to form the de-SOx outlet flue gas and a liquid stream comprising at least one of $H_2O$, $Na_2SO_3$, $Na_2SO_4$, $NaHSO_3$, $Na_2CO_3$, NaCl, $(NH_4)SO_4$, and $NH_4Cl$; or reacting the flue gas with a reactant in an SOx reaction section to form a reaction section flue gas consisting essentially of at least one of $H_2O$, $CO_2$, $N_2$, $O_2$, NaCl, $Na_2CO_3$, $Na_2SO_4$, $NaNO_3$, $CaCl_2$, $CaSO_4$, $Ca(NO_3)_2$, $MgCl_2$, $MgCO_3$, $MgSO_4$, $Mg(NO_3)_2$, NOx, $Cl_2$, dioxins, and furans, wherein the reactant comprises at least one of $NaHCO_3$, $NaHCO_3 \cdot Na_2CO_3 \cdot 2(H_2O)$, $CaCO_3$, $Ca(OH)_2$, and $Mg(OH)_2$; and optionally filtering the reaction section flue gas in a filter section to remove at least one of NaCl, $Na_2CO_3$, $Na_2SO_4$, $NaNO_3$, $CaCl_2$, $CaCO_3$, $CaSO_4$, $Ca(NO_3)_2$, $MgCl_2$, $MgCO_3$, $MgSO_4$, and $Mg(NO_3)_2$, to form the de-SOx outlet flue gas; optionally removing NOx from the de-SOx outlet flue gas in a NOx removal section to form a de-NOx outlet flue gas consisting essentially of at least one of $H_2O$, $CO_2$, $N_2$, $O_2$, dioxins, and furans; and optionally removing dioxin, furan, or both in a dioxin-furan removal section from the de-SOx outlet flue gas or the de-NOx outlet flue gas to form a treated outlet flue gas consisting essentially of at least one of $H_2O$, $CO_2$, $N_2$, and $O_2$.

In some embodiments, removing NOx from the de-SOx outlet flue gas comprises reacting NOx with anhydrous $NH_3$, aqueous $NH_3$, or urea.

In some embodiments, the process further comprises: cooling the dehydrogenated product stream with a solvent forming a cooled dehydrogenated product stream and a used solvent stream; and separating at least a portion of the used solvent stream into a recovered solvent stream and the spent solvent stream in the solvent recovery section; and introducing at least one of the spent solvent stream from the solvent recovery section, and the purge stream from the solvent recovery section to the hydrocarbon buffer vessel.

In some embodiments, the process further comprises: cooling the dehydrogenated product stream; passing the cooled dehydrogenated product stream to an adsorbent bed to produce a purified dehydrogenated product stream; separating the purified dehydrogenated product stream into a recycle feed stream comprising unreacted propane, butane, or mixtures thereof, a recovered dehydrogenated product stream comprising the propylene, butylene, or mixtures thereof, and a net gas stream comprising hydrogen in a cryogenic separation zone; regenerating the adsorbent bed by passing at least a portion of the net gas stream from the cryogenic separation zone to the adsorbent bed and forming a regenerant gas stream; introducing a NaOH stream and the regenerant gas stream into a regenerant gas scrubbing zone to remove sulfur from the regenerant gas stream forming the sulfidic spent caustic stream and a scrubbed regenerant gas stream; and introducing the sulfidic spent caustic stream to the spent caustic buffer vessel.

In some embodiments, the process further comprises at least one of: passing at least a portion of the net gas stream from the cryogenic separation zone to a hydrogen purification zone forming a purified hydrogen stream and a tail gas stream; passing at least a portion of the tail gas stream to at least one of a fired heater as fuel and the fuel gas knockout drum; passing the regenerant gas stream to at least one of the dehydrogenation reaction zone, the hydrogen purification zone, and the fuel gas knockout drum; and passing at least a portion of the net gas stream from the cryogenic separation zone to the fuel gas knockout drum.

In some embodiments, the process further comprises: regenerating the dehydrogenation catalyst in a catalyst regeneration zone forming regenerated catalyst and a catalyst regeneration vent gas stream; adjusting at least one of a pressure or a temperature of the catalyst regeneration vent gas stream to form a conditioned catalyst regeneration vent gas stream; at least one of: passing at least a portion of the conditioned catalyst regeneration vent gas stream to the spent caustic buffer vessel, and thermally oxidizing at least a portion of the conditioned catalyst regeneration vent gas stream; and recycling the regenerated catalyst to the dehydrogenation reaction zone.

In some embodiments, the conditioned catalyst regeneration vent gas stream comprises chlorine gas and wherein the temperature is adjusted using a portion of the sulfidic spent caustic stream which reacts with the chlorine gas.

In some embodiments, the conditioned catalyst regeneration vent gas stream comprises chlorine gas; and introducing the conditioned catalyst regeneration vent gas stream into the spent caustic buffer vessel; and wherein the chlorine gas in the conditioned catalyst regeneration vent gas stream reacts with sulfide, NaOH, and water in the spent sulfidic caustic stream decreasing an amount of reducing agent needed to reduce the chlorine gas compared to a regenerant vent gas treatment system using $NaHSO_3$ or $H_2O_2$.

In some embodiments, the process further comprises: controlling a pressure in at least one of the spent caustic buffer vessel and the hydrocarbon buffer vessel in a push-pull system by introducing a gas stream comprising at least one of fuel gas, off-gas, or waste gas into the at least one of the spent caustic buffer vessel and the hydrocarbon buffer vessel; sending an excess gas stream to the off-gas knockout drum; separating a liquid stream from the excess gas stream in the off-gas knockout drum; and passing the liquid stream to the hydrocarbon buffer vessel.

In some embodiments, the process further comprises: passing the dehydrogenated product stream to a propylene-iso-butylene derivative process unit to form a propylene-iso-butylene derivative product comprising a propylene derivative product, an iso-butylene derivative product, or mixtures thereof, and at least one of a gaseous effluent, a hydrocarbon liquid effluent, and an aqueous effluent; recovering the propylene-iso-butylene derivative product; passing at least one of: the gaseous effluent to the off-gas knockout drum, and the hydrocarbon liquid effluent to the hydrocarbon surge vessel; and optionally passing the aqueous effluent to an aqueous effluent treatment plant.

In some embodiments, the propylene-iso-butylene derivative process unit comprises a propylene derivative process unit comprising a polymerization unit, further comprising; polymerizing the propylene in a polymerization section to form the propylene derivative product comprising polypropylene; separating the polypropylene from the propylene in a monomer recovery section using steam forming a polypropylene stream and a steamer off-gas stream; optionally extruding the polypropylene stream in an extruder section to form a polypropylene product and a tempered water bleed stream; passing at least one of the steamer off-gas stream from the monomer recovery unit to the fuel gas knockout drum, and the tempered water bleed stream from the extruder section to a waste water buffer vessel; and thermally oxidizing a waste water stream from the waste water buffer vessel.

In some embodiments, the propylene-iso-butylene derivative process unit comprises a propylene derivative process unit comprising an acrylonitrile unit, further comprising: reacting the propylene with ammonia and air in an ammoxidation reaction section to form an acrylonitrile reaction mixture; removing a cyanidic off-gas stream and a cyanidic waste water stream from the acrylonitrile mixture; separating the acrylonitrile reaction mixture into an HCN product stream and an acrylonitrile product stream; passing at least one of the cyanidic off-gas stream to the off-gas knockout drum and the cyanidic waste water stream to a waste water buffer vessel; and thermally oxidizing a waste water stream from the waste water buffer vessel.

In some embodiments, the propylene-iso-butylene derivative process unit comprises a propylene derivative process unit comprising an oxo-alcohol unit, further comprising: reacting the propylene with synthesis gas in an oxo-alcohol reaction section to form a reaction mixture comprising butyraldehyde; separating the reaction mixture into an n-butyraldehyde stream, an iso-butyraldehyde stream, and an oxo-alcohol off-gas stream; passing the oxo-alcohol off-gas stream to the off-gas knockout drum.

In some embodiments, the propylene-iso-butylene derivative process unit comprises a propylene derivative process unit comprising an acrylic acid unit, further comprising: partially oxidizing the propylene in an acrylic acid reaction section to form a reaction mixture comprising acrylic acid, acetic acid, $CO_2$, and water; quenching the reaction mixture and separating the quenched reaction mixture into a liquid stream comprising the acrylic acid and the acetic acid, a recycle gas stream, and an acrylic acid off-gas stream; separating the acrylic acid and the acetic acid from the liquid stream in a solvent extraction section to form a lean aqueous raffinate stream and a solvent rich stream comprising the acrylic acid, the acetic acid, and the solvent; fractionating the solvent rich stream in a fractionation section to form a recycle solvent stream and a crude acid stream comprising the acrylic acid and the acetic acid; purifying the crude acid stream in a product purification section to form an acrylic acid product stream, an acetic acid stream, and an acrylic acid waste organic stream; stripping the lean aqueous stream in a stripping section to form an acrylic acid waste water stream and an acid stream; passing at least one of the recycle solvent stream and the acid stream to the solvent extraction section; passing at least one of the acrylic acid off-gas stream to the off-gas knockout drum, the acrylic acid waste organic stream to the hydrocarbon surge drum, and the acrylic acid waste water stream to a waste water buffer vessel; and thermally oxidizing a waste water stream from the waste water buffer vessel.

In some embodiments, the propylene-iso-butylene derivative process unit comprises an iso-butylene derivative process unit comprising a methyl tert-butyl ether (MTBE) unit, further comprising: reacting the iso-butylene with natural gas in a MeOH/MTBE reaction section to produce a MTBE stream comprising methyl tert-butyl ether (MTBE), an oxygenate removal unit (ORU) off-gas stream, a fusel oil stream (a waste stream from methanol manufacturing process which mainly contains heavier alcohols), and a spent alcohol-oily water stream comprising at least one of spent alcohol and oily water; recovering the MTBE stream; optionally cracking a portion of the MTBE to form an iso-butylene stream comprising high purity iso-butylene, a MTBE light ends purge stream, and a MTBE heavies purge stream; passing at least one of the MTBE light ends purge stream to the off-gas knockout drum, the ORU off-gas stream to the off-gas knockout drum, the fusel oil stream to the hydrocarbon buffer vessel, the spent alcohol-oily water stream to the hydrocarbon buffer vessel, the MTBE light ends purge stream to the off-gas knockout drum, and the MTBE heavies purge stream to the off-gas knockout drum.

In some embodiments, the propylene-iso-butylene derivative process unit comprises an iso-butylene derivative process unit comprising an ethyl tert-butyl ether (ETBE) unit, further comprising: reacting the iso-butylene with natural gas in an EtOH/ETBE reaction section to produce an ETBE stream comprising ethyl tert-butyl ether, an oxygenate containing stream, and a spent alcohol-oily water stream comprising at least one of spent alcohol and oily water; recovering the ETBE stream; optionally separating the oxygenate containing stream into an isobutane stream and an ORU off-gas stream, and recycling the isobutane stream to the dehydrogenation reaction zone, and wherein the recycled isobutane stream comprises at least a portion of the alkane feed stream; passing at least one of the spent alcohol-oily water stream to the hydrocarbon buffer vessel, and the ORU off-gas stream to the off-gas knockout drum.

In some embodiments, the propylene-iso-butylene derivative unit comprises an iso-butylene derivative process unit comprising an alkylate unit, further comprising: reacting the iso-butylene in an indirect alkylation section to form an iso-octene stream and an oxygenate containing stream; hydrogenating the iso-octene stream to form an iso-octane stream; recovering the iso-octane stream; optionally separating the oxygenate containing stream into an isobutane stream and an ORU off-gas stream, and recycling the isobutane stream to the dehydrogenation reaction zone and wherein the recycled isobutane stream comprises at least a portion of the alkane feed stream; passing the ORU off-gas stream to the off-gas knockout drum.

In some embodiments, the alkane feed comprises butane and the product stream comprises iso-butylene, further comprising: separating the butane feed stream into a butane stream comprising n-butane and an isobutane stream comprising isobutane and a C5+ heavies purge stream in a de-isobutanizer zone; passing the butane stream to the dehydrogenation zone; isomerizing the isobutane stream in a butane isomerization zone to form a butane isomerate stream; passing the butane isomerate stream to the deisobutanizer section; passing at least one of the C5+ heavies purge stream to the hydrocarbon buffer vessel and an isomerization off-gas stream from the butane isomerization zone to the off-gas knockout drum.

In some embodiments, the alkane feed stream comprises propane and the product stream comprises propylene further comprising: separating the product stream into an unreacted propane stream, a recovered product stream comprising the propylene, and a de-ethanizer off-gas stream; passing the recovered product stream to a product recovery zone; and recycling the unreacted propane stream to the dehydrogenation reaction zone; and passing the de-ethanizer off-gas stream to the fuel gas knockout drum.

In some embodiments, the process further comprises: passing a process fluid stream through a first side of a primary heat exchanger, wherein the process fluid stream comprises all or a portion of at least one of a boiler feed water or oil stream, a combustion air stream, and an offgas stream from a polypropylene storage silo; passing an exhaust vapor stream from the thermal oxidation system through a second side of the primary heat exchanger, wherein the exhaust vapor stream comprises the treated outlet flue gas, the de-NOx outlet flue gas, or the de-SOx outlet flue gas; transferring heat from the exhaust vapor stream to the process fluid stream, cooling the exhaust vapor stream forming a cooled exhaust stream and heating the process fluid stream forming a heated process fluid stream, wherein the heated process fluid stream comprises at least one of a heated boiler feed water or oil stream, a heated combustion air stream, and a heated offgas stream; passing at least one of: the heated boiler feed water or oil stream to the waste heat recovery section, the heated combustion air stream to the thermal oxidizing section, and the heated offgas stream to the thermal oxidizing section; and passing the cooled exhaust stream to an exhaust stack.

In some embodiments, the process further comprises: passing a waste liquid stream to a first side of a secondary heat exchanger before passing the exhaust vapor stream to the primary heat exchanger to reduce a temperature of the exhaust vapor stream forming a second cooled vapor stream and to heat the waste liquid stream forming a heated waste liquid stream, wherein the waste liquid stream comprises at least one of the spent caustic stream from the spent caustic buffer vessel, and a waste water stream from a waste water buffer vessel, spent caustic buffer vessel; passing the second cooled vapor stream to the primary heat exchanger and wherein passing the exhaust vapor stream through the second side of the primary heat exchanger comprises passing the second cooled exhaust vapor stream through the second side of the primary heat exchanger; and passing the heated waste liquid stream to the thermal oxidizing section of the thermal oxidation system.

In some embodiments, the exhaust vapor stream is cooled in the primary heat exchanger to a temperature at or below a dew point to condense water from the exhaust vapor stream, forming a first condensate stream.

In some embodiments, the process further comprises: passing the first condensate stream to at least one of a feed preparation section of a propane dehydrogenation complex, a methyl tert-butyl ether (MTBE) synthesis unit of a MTBE/high purity iso-butylene derivative process unit, an ethyl tert-butyl ether (ETBE) synthesis unit of an ETBE derivative process unit, and an indirect alkylation reaction section of an alkylate derivative process unit.

In some embodiments, the cooled exhaust vapor stream is passed to a third heat exchanger before being passed to the exhaust stack, and wherein the cooled exhaust vapor stream is further cooled in the third heat exchanger to a temperature at or below a dew point to condense water from the cooled exhaust vapor stream, forming a second condensate stream.

In some embodiments, the process further comprises: passing the second condensate stream to at least one of a feed preparation section of a propane dehydrogenation complex, a methyl tert-butyl ether (MTBE) synthesis unit of a MTBE/high purity iso-butylene derivative process unit, an ethyl tert-butyl ether (ETBE) synthesis unit of an ETBE derivative process unit, and an indirect alkylation reaction section of an alkylate derivative process unit.

FIG. 1 illustrates a conventional propane and/or butane dehydrogenation complex 100.

An alkane feed stream 105 comprising propane and/or butane is sent to a cryogenic separation zone 110 to vaporize the liquid feed. The alkane feed stream 115 exits the cryogenic separation zone 110 as a vapor and is sent to the dehydrogenation reaction zone 120.

The operating conditions of the dehydrogenation reaction zone 120 typically include: a temperature in the range of 500° C. to 1000° C., a pressure in a range of 0 to 1379 kPa, and a space velocity of 0.1 to 10 $hr^{-1}$ weight hourly space velocity (WHSV). The catalyst comprises typically a noble metal, such as platinum, palladium, and/or a Group VI element, such as chromium, molybdenum, and tungsten, supported on inorganic oxides, such as alumina, silica, magnesia, or mixtures thereof. Optionally, a Group 13 element, such as indium or gallium, and/or a Group 14 element, such as tin or germanium or mixtures thereof can be incorporated as a modifier. Optionally, alkali and/or alkali earth metals can also be incorporated to modify and improve the catalyst activity, selectivity, and stability. The hydrocarbons are contacted with the dehydrogenation catalyst in a fixed catalyst bed system, a moving catalyst bed system, a fluidized bed system, etc., or in continuous or sequential switched operation. The dehydrogenation zone may comprise one or more separate reaction zones with heating in between to ensure that the desired reaction temperature can be maintained at the entrance to each reaction zone. The hydrocarbon may be contacted with the catalyst bed in either upward, downward, or radial flow fashion.

The dehydrogenated product stream 125 from the dehydrogenation reaction zone 120 generally will contain unconverted dehydrogenatable hydrocarbons (e.g., propane and/or isobutane), hydrogen, and the products of dehydrogenation reactions (e.g., propylene and/or iso-butylene).

The dehydrogenated product stream 125 can be cooled by heat exchange with the alkane feed stream 115 in a heater exchanger 130 and sent to a reactor effluent contact cooler 135, for example. The dehydrogenated product stream 125 can be further cooled by contact with a solvent 140. Additional solvent can be added with make-up solvent stream 143.

The used solvent stream 145 can be sent to a solvent recovery section 150 comprising one or more distillation columns, for example. The used solvent stream 145 is separated into a recovered solvent stream 155, and a spent solvent stream 160. The recovered solvent stream 155 can be recycled to the reactor effluent contact cooler 135. A portion 175 of the used solvent stream 145 can bypass the solvent recovery section 150, be cooled in solvent cooler 177, and be sent to the reactor effluent contact cooler 135. A recycled light aromatic solvent stream 165 (from a depropanizer bottoms stream (not shown)) is sent to the solvent recovery section 150. A purge stream 170 (also from the depropanizer bottoms stream) is mixed with the spent solvent stream 160. The spent solvent stream 160 is sent to disposal or storage.

The cooled dehydrogenated product stream 180 can be compressed, cooled in reactor effluent cooler 182, and sent to discharge drum 185 where the liquid that condenses from the compressed reactor effluent is separated as recycle wash oil or solvent stream 187. In some embodiments, the recycle wash oil or solvent stream 187 is mainly light aromatic components, it can be returned to the solvent recovery section 150. In other embodiments, the recycle wash oil or solvent stream 187 comprises mainly water from condensed steam. In this case, recycle wash oil or solvent stream 187 is sent to waste water treatment.

The cooled dehydrogenated product stream 190 from the discharge drum 185 is sent to an adsorbent bed 195 to remove sulfur. The purified dehydrogenated product stream 200 is sent to the cryogenic separation zone 110 to separate a net gas stream 205 rich in hydrogen from the recovered dehydrogenated product stream 210 comprising propylene and/or butylene. The recovered dehydrogenated product stream 210 can be sent for further separation and processing as needed. Unreacted propane and/or butane is sent back to the dehydrogenation reaction zone 120.

The net gas stream 205 can be split into an excess net gas stream 215, a regeneration net gas stream 220, and a third net gas stream 225. Excess net gas stream 215 can be used as fuel gas, for example or in other processes.

Regeneration net gas stream 220 is sent to the adsorbent bed 195 to regenerate the adsorbent by removing acid gas. The regenerant gas stream 230 from the adsorbent bed 195 is sent to the regenerant gas scrubbing zone 235. A NaOH stream 240 is introduced into the regenerant gas scrubbing zone 235 to remove sulfur from the regenerant gas stream 230 forming a sulfidic spent caustic stream 245 and a scrubbed regenerant gas stream 250.

The sulfidic spent caustic stream 245 is sent to a spent sulfidic caustic treatment zone 255 to remove the sulfur. The liquid effluent 260 from the spent sulfidic caustic treatment zone 255 is sent to an effluent treatment plant 265 for further treatment.

The third net gas stream 225 is sent to a hydrogen purification zone 270. Optionally, a hydrogen stream 275 from the regenerant gas scrubbing zone 235 can be sent to the hydrogen purification zone 270. A purified hydrogen stream 280 and a tail gas stream 285 are formed in the hydrogen purification zone 270. The purified hydrogen stream 280 is sent for use in other areas of the plant as needed. The tail gas stream 285 can be used as fuel gas for fired heaters, for example in the fired heater section of the dehydrogenation reaction zone 120. An excess tail gas stream 290 can be used as fuel gas for fired heaters elsewhere, for example.

Spent dehydrogenation catalyst 293 from the dehydrogenation reaction zone 120 can be sent to a catalyst regeneration zone 295 with an air stream 300 to remove coke from the catalyst. An $N_2$ stream 305 and a $Cl_2$ stream 310 are introduced into the catalyst regeneration zone 295. The regenerated catalyst 313 is then returned to the dehydrogenation reaction zone 120.

The catalyst regeneration process generates a catalyst regeneration vent gas stream 315 which is sent to a regeneration vent gas treatment zone 320. A NaOH stream 325 and a $NaHSO_3$ stream 330 are introduced into the regeneration vent gas treatment zone 320 to react with the chlorine present in the catalyst regeneration vent gas stream 315 forming a chloridic spent caustic stream 335. The chloridic spent caustic stream 335 is sent to the effluent treatment plant 265.

Figure 2:
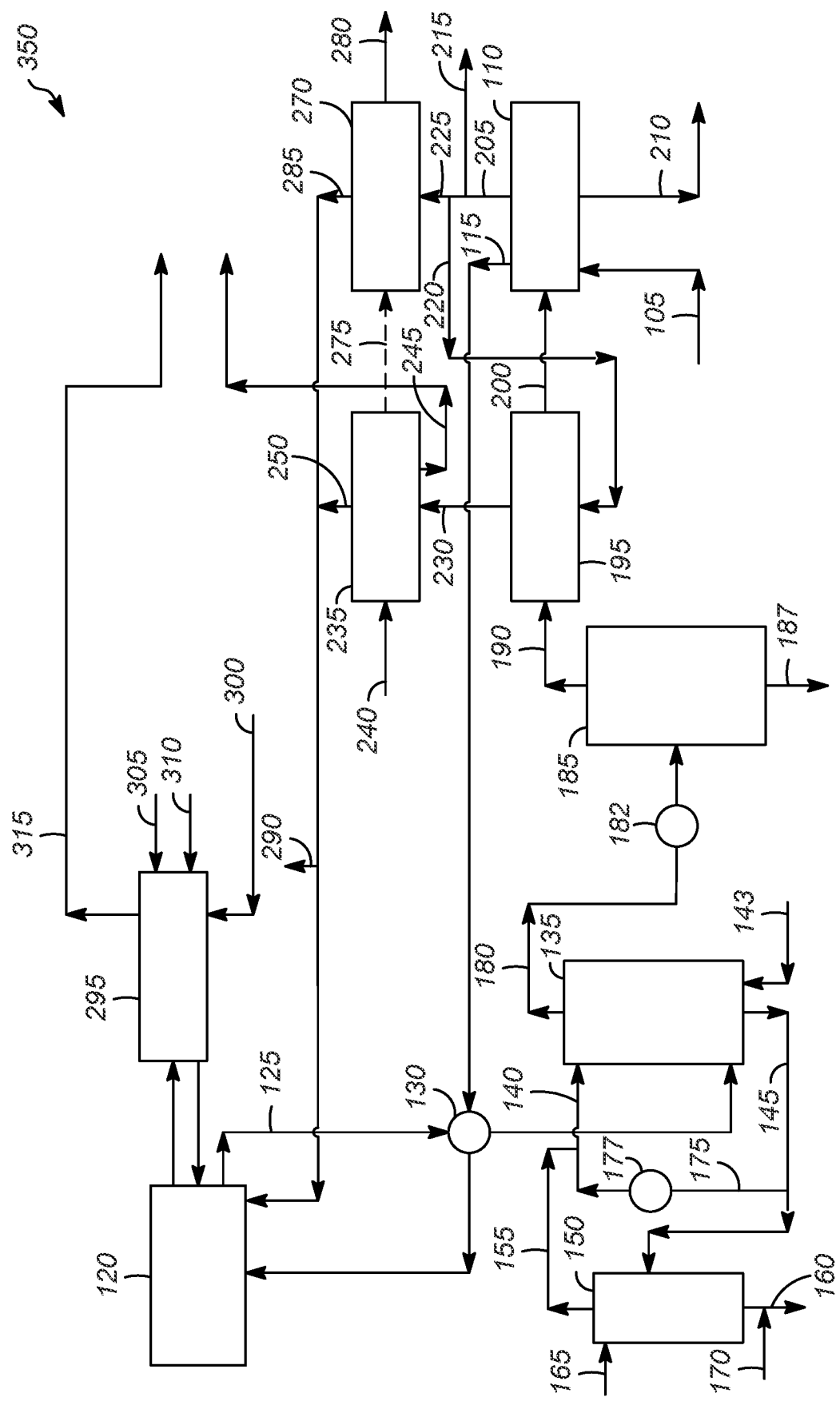
FIGS. 2-3 are an illustration of one embodiment of a propane/butane dehydrogenation complex according to the present invention.
Figure 3:
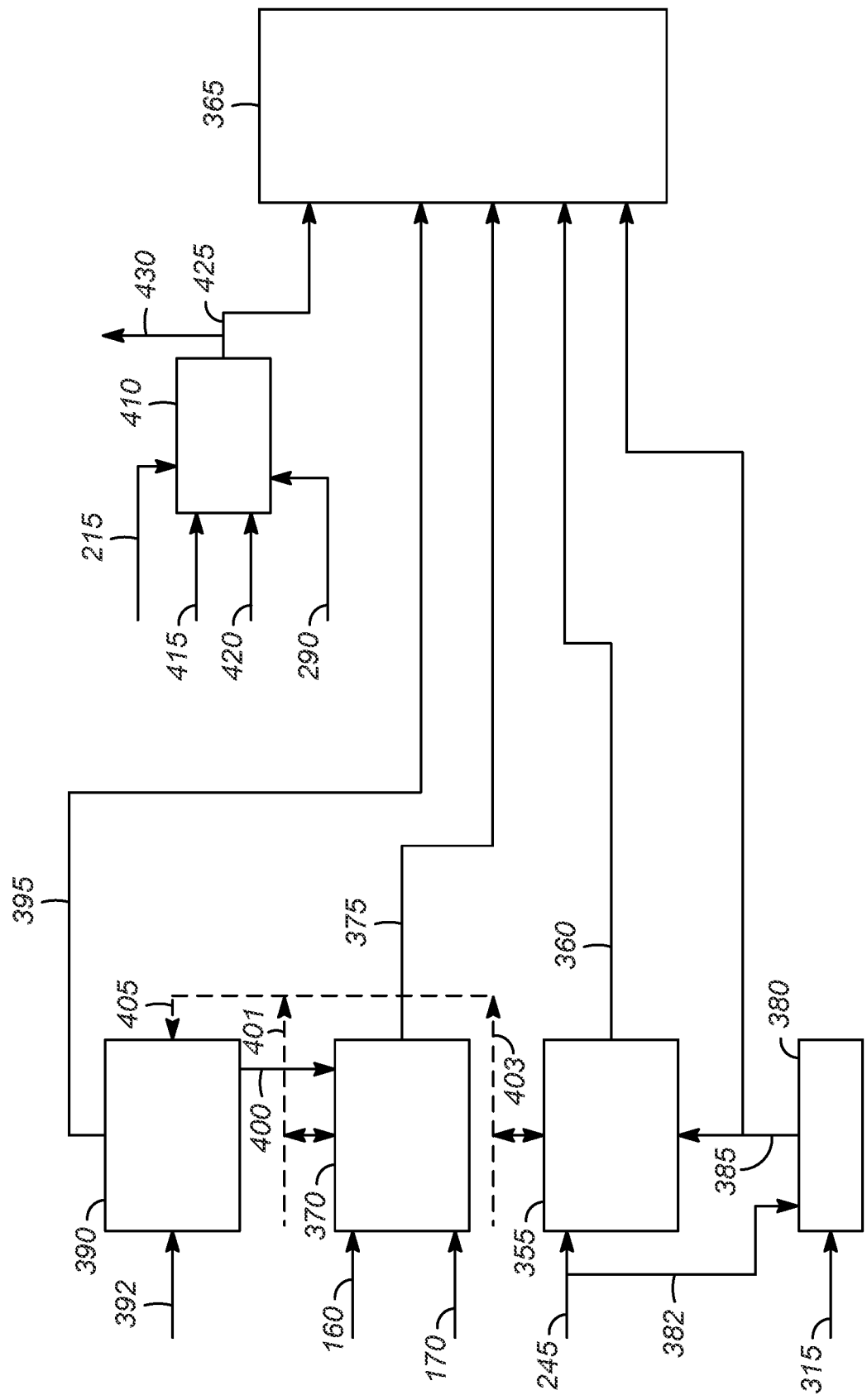

FIGS. 2-3 illustrate the use of the present invention in the propane and/or butane dehydrogenation complex of FIG. 1. In this embodiment, the spent sulfidic caustic treatment zone 255, the effluent treatment plant 265, and the regeneration vent gas treatment zone 320 are eliminated as shown in FIG. 2.

As shown in FIG. 3, the sulfidic spent caustic stream 245 from the regenerant gas scrubbing zone 235 is sent to a spent caustic buffer vessel 355. A spent caustic stream 360 from the spent caustic buffer vessel 355 is sent to a thermal oxidation system 365, which will be described in more detail below.

One or more of the spent solvent stream 160 from the solvent recovery section 150, and the purge stream 170 from the solvent recovery section 150 are sent to a hydrocarbon buffer vessel 370. A liquid hydrocarbon stream 375 from the hydrocarbon buffer vessel 370 is sent to the thermal oxidation system 365.

The catalyst regeneration vent gas stream 315 can be sent to a conditioning section 380 where the temperature and/or the pressure of the catalyst regeneration vent gas stream 315 can be adjusted as needed. Pressure adjustment can be accomplished using methods including, but not limited to, a blower or a steam ejector. The temperature can be adjusted using methods including, but not limited to, direct or indirect cooling using various types of heat exchanges, or by direct mixing with water, air, or flue gas.

The catalyst regeneration vent gas stream 315 will contain moisture and will likely also contain acid gas components, such as HCl and $Cl_2$. Because of this, catalyst regeneration vent gas stream 315 should not be below the dew point, except where the quench is done with a caustic solution. Consequently, the temperature reduction in the conditioning section 380 can be done using a slip stream 382 from the sulfidic spent caustic stream 245. In most cases, no additional NaOH would be needed.

The conditioned catalyst regeneration vent gas stream 385 can be sent directly to the thermal oxidation system 365. In this case, only the pressure may need to be adjusted. Alternatively, the conditioned catalyst regeneration vent gas stream 385 can be sent to the spent caustic buffer vessel 355. In this case, both the pressure and the temperature will likely need to be adjusted.

By sending the conditioned catalyst regeneration vent gas stream 385 to the spent caustic buffer vessel 355, the inherent redox potential advantage between the catalyst regeneration vent gas stream 315, which contains $Cl_2$, and the sulfidic spent caustic stream 245, which contains NaHS/$Na_2S$, can be used to neutralize the $Cl_2$ and oxidize the NaHS/$Na_2S$. In the conventional configuration where the catalyst regeneration vent gas stream 315 is send to a regeneration vent gas treatment zone 320, the $Cl_2$ is addressed by adding a reducing agent like $NaHSO_3$ to convert the $Cl_2$ to HCl via the following reactions:

$$NaHSO_3+Cl_2+H_2O \rightarrow NaHSO_4+2HCl.$$

This is followed by a NaOH scrubbing reaction where:

$$HCl+NaOH \rightarrow NaCl++H_2O$$

and $$NaHSO_4+NaOH \rightarrow Na_2SO_4+H_2O.$$

Because the sulfidic spent caustic stream 245 is reducing in nature, it can be used to convert $Cl_2$, thereby eliminating the need for a reducing agent like $NaHSO_3$.

In addition, because there will always be an excess of $NaHS/Na_2S$ compared to $Cl_2$, the invention also utilizes the following reactions:

$$Na_2S+3Cl_2+5NaOh \rightarrow NaHSO_3+6NaCl+2H_2O$$

$$NaHS+3Cl_2+6NaOH \rightarrow NaHSO_3+6NaCl+2H_2O.$$

The net remaining $NaHS/Na_2S$ will be oxidized in the thermal oxidation system 365 by $O_2$ from ambient air.

One or more streams 392 with significant acid content (which raises corrosion concerns) or nitrogen bearing compounds (which raises concerns about NOx formation) can be sent to the off-gas knockout drum 390. These streams can be contaminated, and as such, cannot be sent to the fuel gas knockout drum, which deals with clean fuel streams. Examples of such streams include, but are not limited to, cyanidic off-gas stream 720 from the product recovery section 715 (FIG. 5B) and acrylic acid off-gas stream 865 from the quench and off-gas separation section 855 (FIG. 5D), discussed below. An off-gas stream 395 from the off-gas knockout drum 390 can be sent to the thermal oxidation system 365. A liquid condensable stream 400 from the off-gas knockout drum 390 can be sent to the hydrocarbon buffer vessel 370.

The hydrocarbon buffer vessel 370 and the spent caustic buffer vessel 355 can be operated with a push/pull system using liquefied petroleum gas/waste gas/fuel gas to maintain a constant pressure. There is a gas stream 401, 403 into and out of each of the hydrocarbon buffer vessel 370 and the spent caustic buffer vessel 355 to maintain a constant pressure. When the pressure is high, gas will be pushed out of the hydrocarbon buffer vessel 370 and the spent caustic buffer vessel 355 to the off-gas knockout drum 390, while it will be pulled into the hydrocarbon buffer vessel 370 and the spent caustic buffer vessel 355 when the pressure is low via the waste gas/fuel gas supply line 405.

Excess net gas stream 215 and excess tail gas stream 290 can be sent to a fuel gas knockout drum 410. The fuel gas knockout drum 410 can take fuel containing stream, such as an off-gas degassing drum stream 415 and fuel gas and/or natural gas stream 420 from other parts of the plant, if desired. A fuel gas stream 425 from the fuel gas knockout drum 410 can be sent to the thermal oxidation system 365. A portion 430 of the fuel gas stream 425 can be used in other parts of the complex as needed. It should be noted that a fuel gas knock drum could be a part of the conventional propane and/or butane dehydrogenation complex 100, although not shown in FIG. 1.

Figure 4:
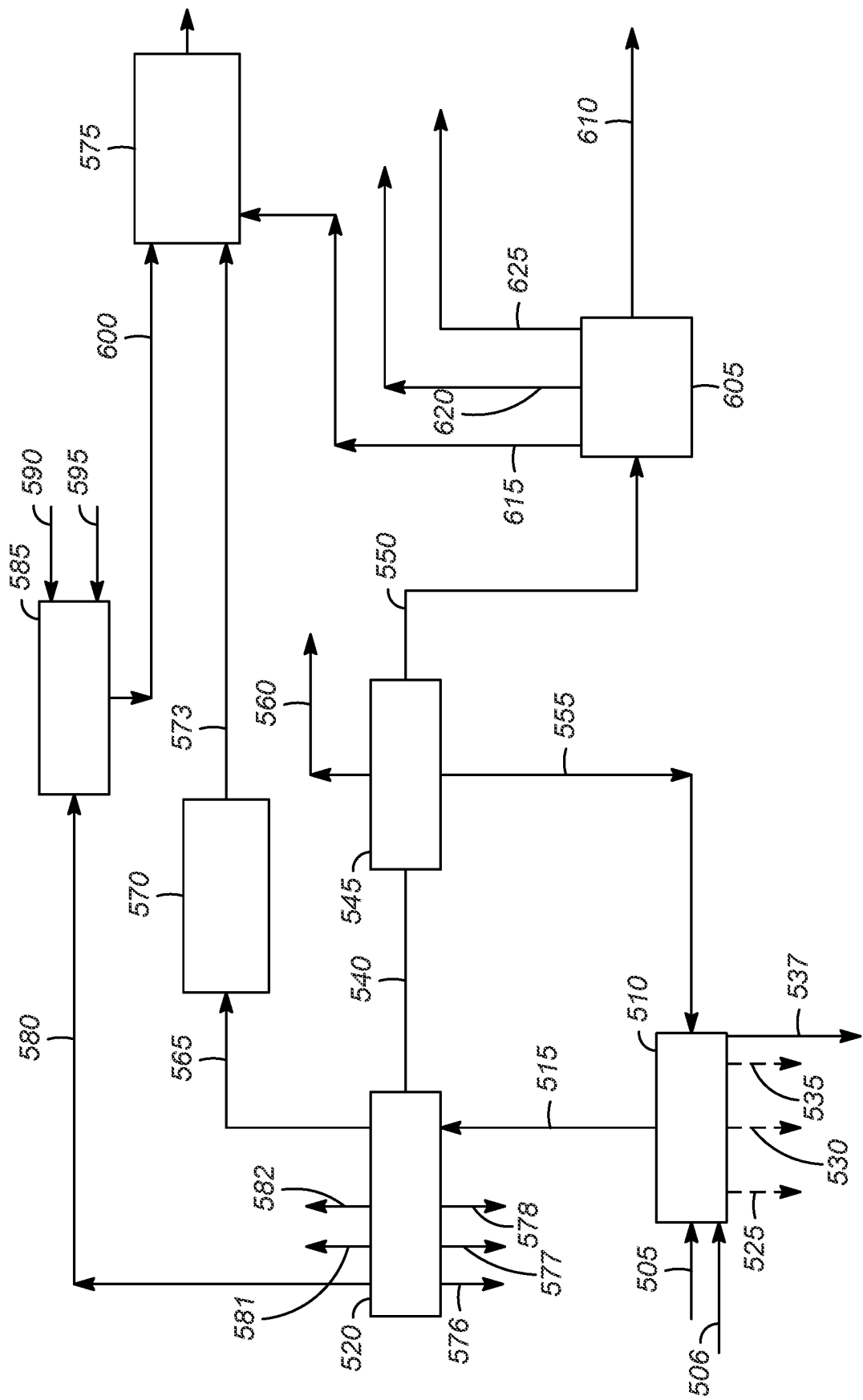
FIG. 4 is an illustration of one embodiment of a propane dehydrogenation complex with propylene derivative process units.

FIG. 4 is a simplified illustration of a propane dehydrogenation complex 500 including a propylene derivative process units.

The propane feed stream 505 and make-up wash water stream 506 are sent to a feed preparation section 510. A propane stream 515 from the feed preparation section 510 is sent to the propane dehydrogenation section 520. Depending on the feed source, in some embodiments, wash water purge stream 525, a spent carbonyl sulfide (COS) removal solvent stream 530, a sulfidic spent caustic stream 535, and MeOH waste water stream 537 are sent for disposal. Suitable disposal methods include chemical neutralization, wet air oxidation system, dilution, deep well injection, and waste water treatment.

The dehydrogenation effluent stream 540 is sent to a product recovery section 545 where it is divided into a propylene stream 550, a recycle propane stream 555 and a de-ethanizer off-gas stream 560. The recycle propane stream 555 is sent to the feed preparation section 510. The de-ethanizer off-gas stream 560 is sent to a mixed fuel gas drum for use as fuel in heaters in the dehydrogenation process.

The sulfidic spent caustic stream 565 is sent to the spent sulfidic caustic treatment section 570. The liquid effluent 573 from the spent sulfidic caustic treatment section 570 is sent to the effluent treatment plant 575.

Spent solvent stream 576 from the propane dehydrogenation section 520, wash oil stream 577 from the propane dehydrogenation section 520, and purge stream 578 from the propane dehydrogenation section 520 are sent disposal or storage. Excess net gas 581 from the propane dehydrogenation section 520 is sent to a mixed fuel gas drum for use as fuel in heaters in the dehydrogenation process. Excess tail gas 582 from the propane dehydrogenation section 520 is used as fuel gas.

The catalyst regeneration vent gas stream 580 is sent to the regeneration vent gas treatment section 585. A NaOH stream 590 and a $NaHSO_3$ stream 595 are introduced into the regeneration vent gas treatment section 585 to react with the chlorine present in the catalyst regeneration vent gas stream 580 forming a chloridic spent caustic stream 600. The chloridic spent caustic stream 600 is sent to the effluent treatment plant 575.

The propylene stream 550 from the product recovery section 545 is sent to a propylene derivative process unit 605. The propylene derivative process unit 605 produces a propylene derivative stream 610 which is recovered. One or more additional streams are also produced. There can be one or more aqueous effluent streams 615, one or more gaseous effluent streams 620, and one or more rich hydrocarbon effluent streams 625 (i.e., high calorific/low selling value streams having a heating value greater than 2500 BTU/lb). The aqueous effluent streams 615 are sent to the effluent treatment plant 575. The gaseous effluent streams 620 are sent to a flare relief header, a fuel gas network, and/or a dedicated thermal oxidizer. The rich hydrocarbon effluent streams 625 are sent to storage.

Figure 5A:
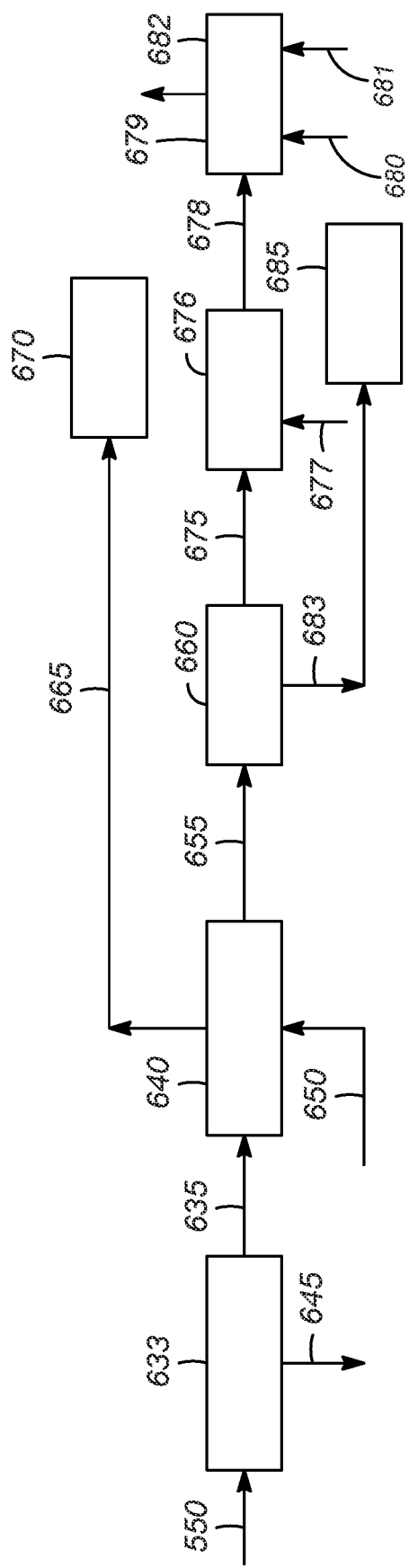
FIGS. 5A-5D are illustrations of embodiments of propylene derivative process units.

FIGS. 5A-D illustrate several propylene derivative process units. FIG. 5A shows a polypropylene derivative process unit 630. The propylene stream 550 is sent to a polymerization section 633. A polypropylene effluent stream 635 is sent to the monomer recovery section 640. A purge stream 645 is typically sent to the de-ethanizer in the product recovery section 545. Steam stream 650 is introduced into the monomer recovery section 640 to remove propylene monomer. The purified polypropylene 655 is sent to the extruder section 660. Steamer off-gas stream 665 is sent to a relief header 670. In other embodiments, steamer off-gas stream 665 is recycled to the reactor effluent contact cooler 135 for recovery. The polypropylene is extruded into a polypropylene product 675 which is sent to polypropylene storage silo 676. Air stream 677 is circulated in the polypropylene storage silo 676. The off-gas stream 678 is sent to regenerative thermal oxidizer (RTO) 679 along with combustion air 680 and fuel gas 681. The purified air stream 682 can be released to the atmosphere. A tempered water bleed stream 683 is sent to a waste water treatment plant 685.

Figure 5B:
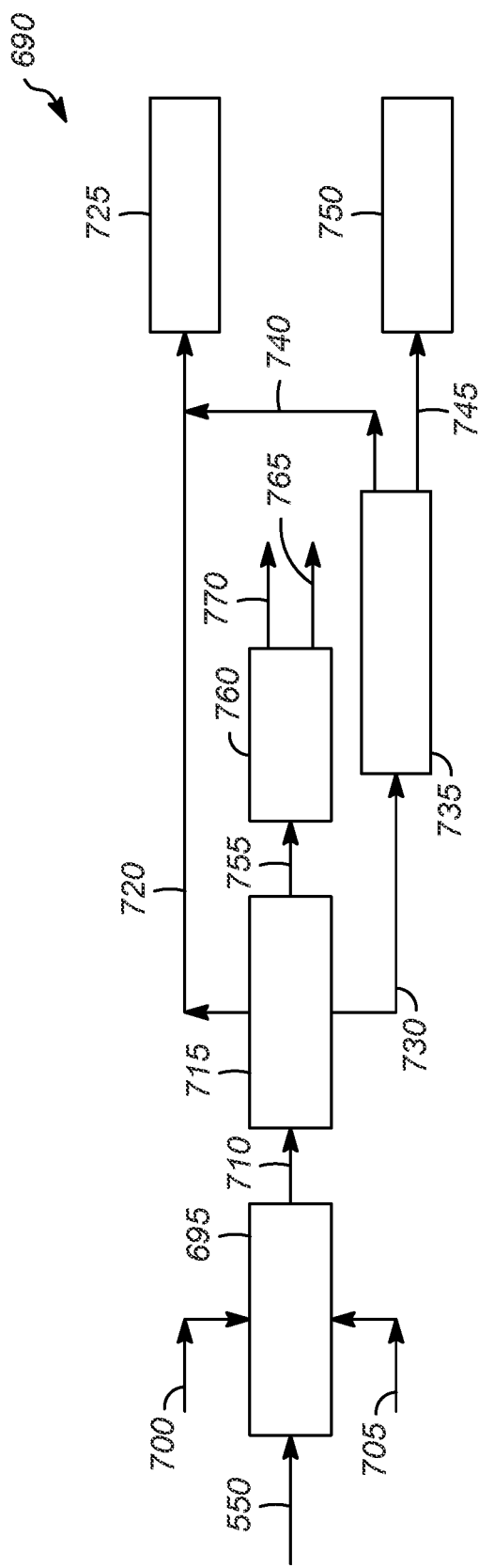

FIG. 5B shows an acrylonitrile derivative process unit 690. The propylene stream 550 is sent to the acrylonitrile reaction section 695 along with an $NH_3$ stream 700 and an air stream 705. The acrylonitrile reactor effluent 710 is sent to a product recovery section 715. A cyanidic off-gas stream 720 from the product recovery section 715 is sent to a dedicated thermal oxidizer 725. A cyanidic waste water stream 730 from the product recovery section 715 is sent to cyanide destruction section 735. The gaseous effluent 740 from the cyanide destruction section 735 is sent to the dedicated thermal oxidizer 725. The liquid effluent 745 from the cyanide destruction section 735 is sent to a waste water treatment plant 750. The effluent 755 from the product recovery section 715 is sent to a product purification section 760 to form an acrylonitrile product stream 765 and an HCN product stream 770.

Figure 5C:
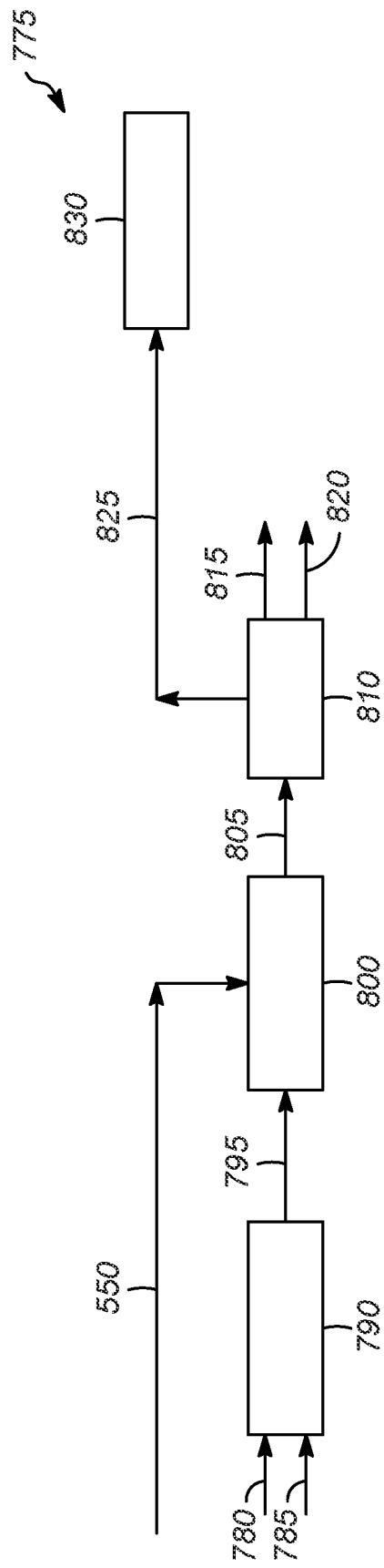

FIG. 5C shows an oxo-alcohols derivative process unit 775. Natural gas 780 and steam 785 are sent to a synthesis gas section 790. The synthesis gas 795 and propylene stream 550 are sent to the oxo-alcohols section 800. The oxo-alcohols unit effluent 805 is sent to product separation section 810 where it is separated into an n-butyraldehyde stream 815 and an iso-butyraldehyde stream 820. The oxo-alcohol off-gas stream 825 is sent to a relief header or fuel gas network 830.

Figure 5D:
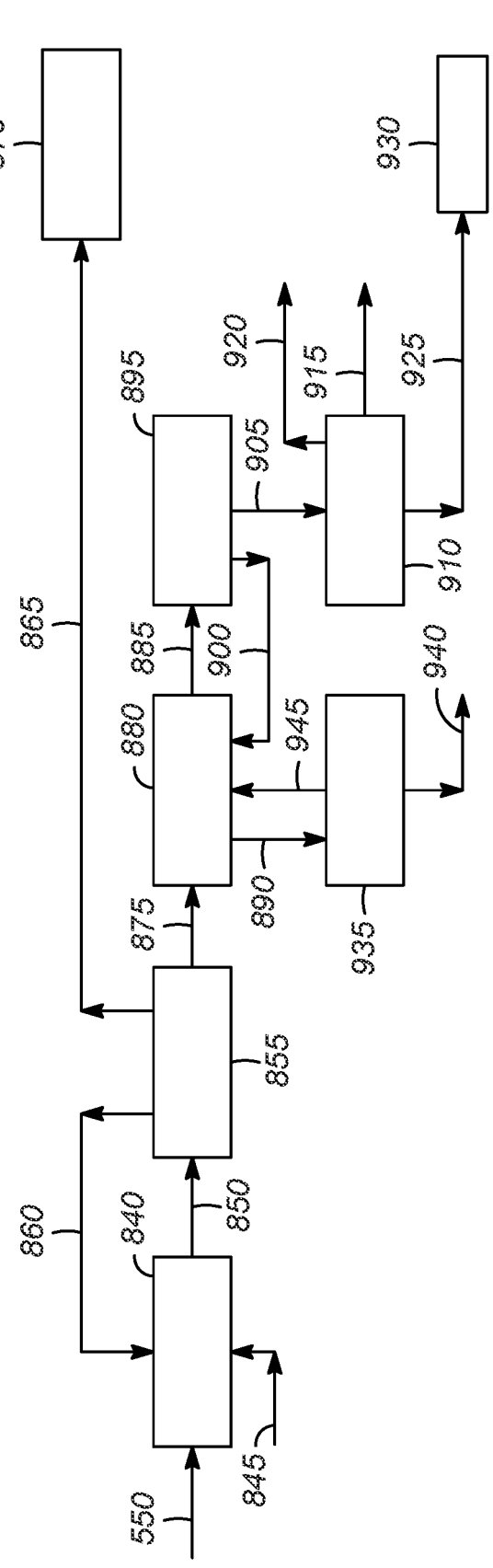

FIG. 5D illustrates an acrylic acid derivative process unit 835. The propylene stream 550 is sent to an acrylic acid reactor section 840 along with air stream 845. The acrylic acid effluent 850 is sent to a quench and off-gas separation section 855. Recycle stream 860 is sent back to the acrylic acid reactor section 840. Acrylic acid off-gas stream 865 is sent to a relief header or fuel gas network 870. The liquid effluent stream 875 from the quench and off-gas separation section 855 is sent to the solvent extraction section 880 where a solvent rich stream 885 and a lean aqueous raffinate stream 890 are formed. The solvent rich stream 885 is sent to a fractionation section 895 and separated into a recycle solvent stream 900 and a crude acid stream 905 comprising acrylic acid and acetic acid. The recycle solvent stream 900 from fractionation section 895 is recycled to the solvent extraction section 880. The crude acid stream 905 from the fractionation section 895 is purified in a product purification section 910 to form an acrylic acid product stream 915, an acetic acid stream 920, and an acrylic acid waste organic stream 925. The acrylic acid waste organic stream 925 is sent to a disposal section 930. The lean aqueous raffinate stream 890 is stripped in a solvent stripping section 935 to form an acrylic acid waste water stream 940 and an acid stream 945. The acid stream 945 is sent to solvent extraction section 880. The acrylic acid waste water stream 940 is sent to waste water treatment.

Figure 6:
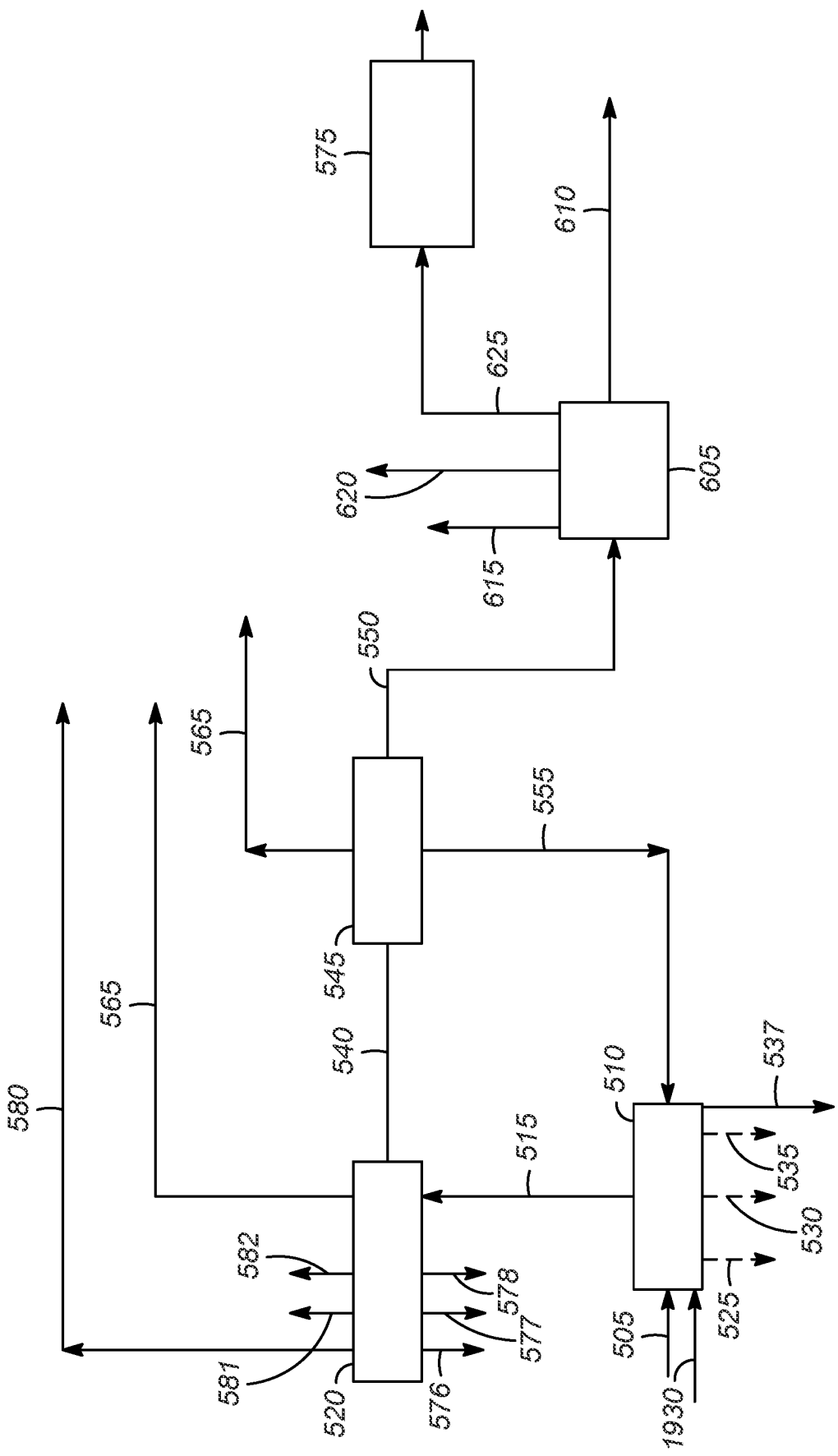
FIG. 6 is an illustration of a portion of one embodiment of a propane dehydrogenation complex with propylene derivative process units according to the present invention.

FIGS. 6, 7A-7D, and 8 illustrate the same basic propane dehydrogenation complex shown in FIGS. 4 and 5A-5D according to the present invention. As shown in FIG. 6, the spent sulfidic caustic treatment section 570 and the regeneration vent gas treatment section 585 from FIGS. 4 and 5A-5D have been eliminated, reducing equipment costs. As a result, there is no liquid effluent 573 from the spent sulfidic caustic treatment section 570 or chloridic spent caustic stream 600 to be sent to the effluent treatment plant 575 from FIGS. 4 and 5A-5D, allowing the effluent treatment plant to be smaller.

Figure 8:
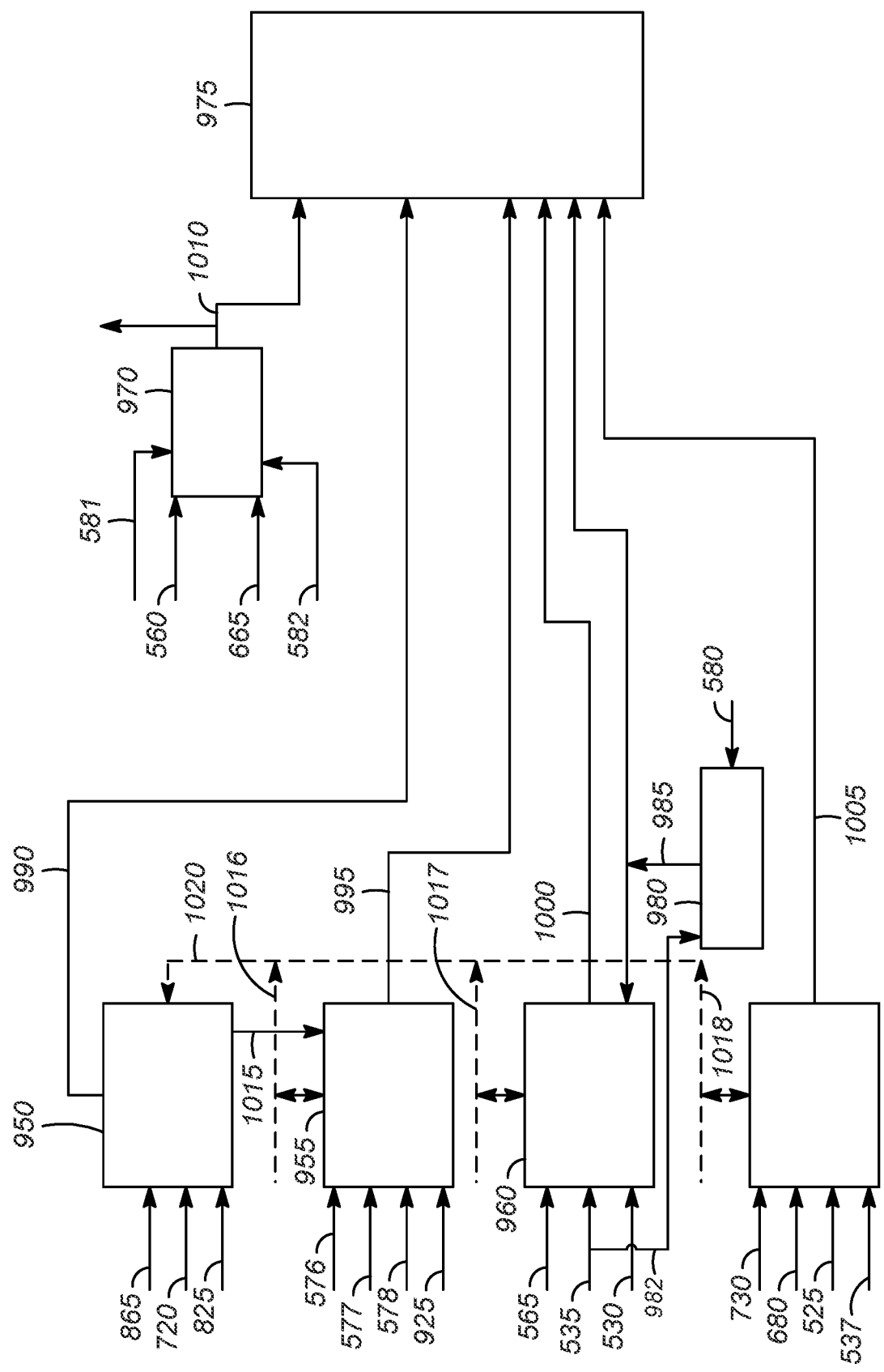
FIG. 8 is an illustration of another portion of the propane dehydrogenation complex with propylene derivative process units of FIGS. 6 and 7A-7D according to the present invention.

As shown in FIG. 8, the process includes an off-gas knockout drum 950, a hydrocarbon buffer vessel 955, a spent caustic buffer vessel 960, a waste water buffer vessel 965, a fuel gas knockout drum 970, and a thermal oxidation system 975.

As shown in FIGS. 6 and 8, the wash water purge stream 525 from the feed preparation section 510 is sent to the waste water buffer vessel 965. The spent COS removal solvent stream 530 from the feed preparation section 510 is sent to the spent caustic buffer vessel 960. The sulfidic spent caustic stream 535 from the feed preparation section 510 is sent to the spent caustic buffer vessel 960. The sulfidic spent caustic stream 565 from the propane dehydrogenation section 520 is sent to the spent caustic buffer vessel 960. The spent solvent stream 576, wash oil stream 577, and purge stream 578 from the propane dehydrogenation section 520 are sent to the hydrocarbon buffer vessel 955. The excess net gas 581 and excess tail gas 582 from the propane dehydrogenation section 520 are sent to the fuel gas knockout drum 970. The catalyst regeneration vent gas stream 580 from the propane dehydrogenation section 520 is sent to the conditioning section 980. A slip stream 982 from the sulfidic spent caustic stream 535 can be sent to the conditioning section 980 for temperature reduction. The conditioned catalyst regeneration vent gas stream 985 can be sent directly to the thermal oxidation system 975 or to the spent caustic buffer vessel 960. The de-ethanizer off-gas stream 560 from the product recovery section 545 is sent to the fuel gas knockout drum 970.

The treatment of the gaseous effluent streams 620 and rich hydrocarbon effluent streams 625 from the propylene derivative process units 605 will discussed below with respect to each derivative process unit.

As shown in FIGS. 7A and 8, for the polypropylene derivative process unit 630, the waste water treatment plant is eliminated. The steamer off-gas stream 665 from the monomer recovery section 640 is sent to the fuel gas knockout drum 970. The tempered water bleed stream 683 from the extruder section 660 is sent to the waste water buffer vessel 965.

As shown in FIGS. 7B and 8, in the acrylonitrile derivative process unit 690, the dedicated thermal oxidizer, cyanide destruction section, and waste water treatment plant are removed. The cyanidic off-gas stream 720 from the product recovery section 715 is sent to the off-gas knockout drum 950. The cyanidic waste water stream 730 from the product recovery section 715 is sent to the waste water buffer vessel 965.

As shown in FIGS. 7C and 8, in the oxo-alcohols derivative process unit 775, the oxo-alcohol off-gas stream 825 from the product separation section 810 is sent to the off-gas knockout drum 950, rather than the relief header or fuel gas network.

As shown in FIGS. 7D and 8, for the acrylic acid derivative process unit 835, the acrylic acid off-gas stream 865 from the quench and off-gas separation section 855 is sent to the off-gas knockout drum 950. The acrylic acid waste organic stream 925 from the product purification section 910 is sent to the hydrocarbon buffer vessel 955.

An off-gas stream 990 from the off-gas knockout drum 950, a liquid hydrocarbon stream 995 from the hydrocarbon buffer vessel 955, a spent caustic stream 1000 from the spent caustic buffer vessel 960, a waste water stream 1005 from the waste water buffer vessel 965, and a fuel gas stream 1010 from the fuel gas knockout drum 970 are sent to the thermal oxidation system 975.

A liquid condensable stream 1015 can be sent from the off-gas knockout drum 950 to the hydrocarbon buffer vessel 955

The hydrocarbon buffer vessel 955, the spent caustic buffer vessel 960, and the waste water buffer vessel 965 can be operated with a push/pull system using liquefied petroleum gas/waste gas/fuel gas to maintain a constant pressure. There is a vent gas stream 1016, 1017, 1018 into and out of each of the hydrocarbon buffer vessel 955, the spent caustic buffer vessel 960, and the waste water buffer vessel 965 to maintain a constant pressure. When the pressure is high, gas will be pushed out of the hydrocarbon buffer vessel 955, the spent caustic buffer vessel 960, and the waste water buffer vessel 965, while it will be pulled into the hydrocarbon buffer vessel 955, the spent caustic buffer vessel 960, and the waste water buffer vessel 965 when the pressure is low via the waste gas/fuel gas supply line 1020.

Figure 9:
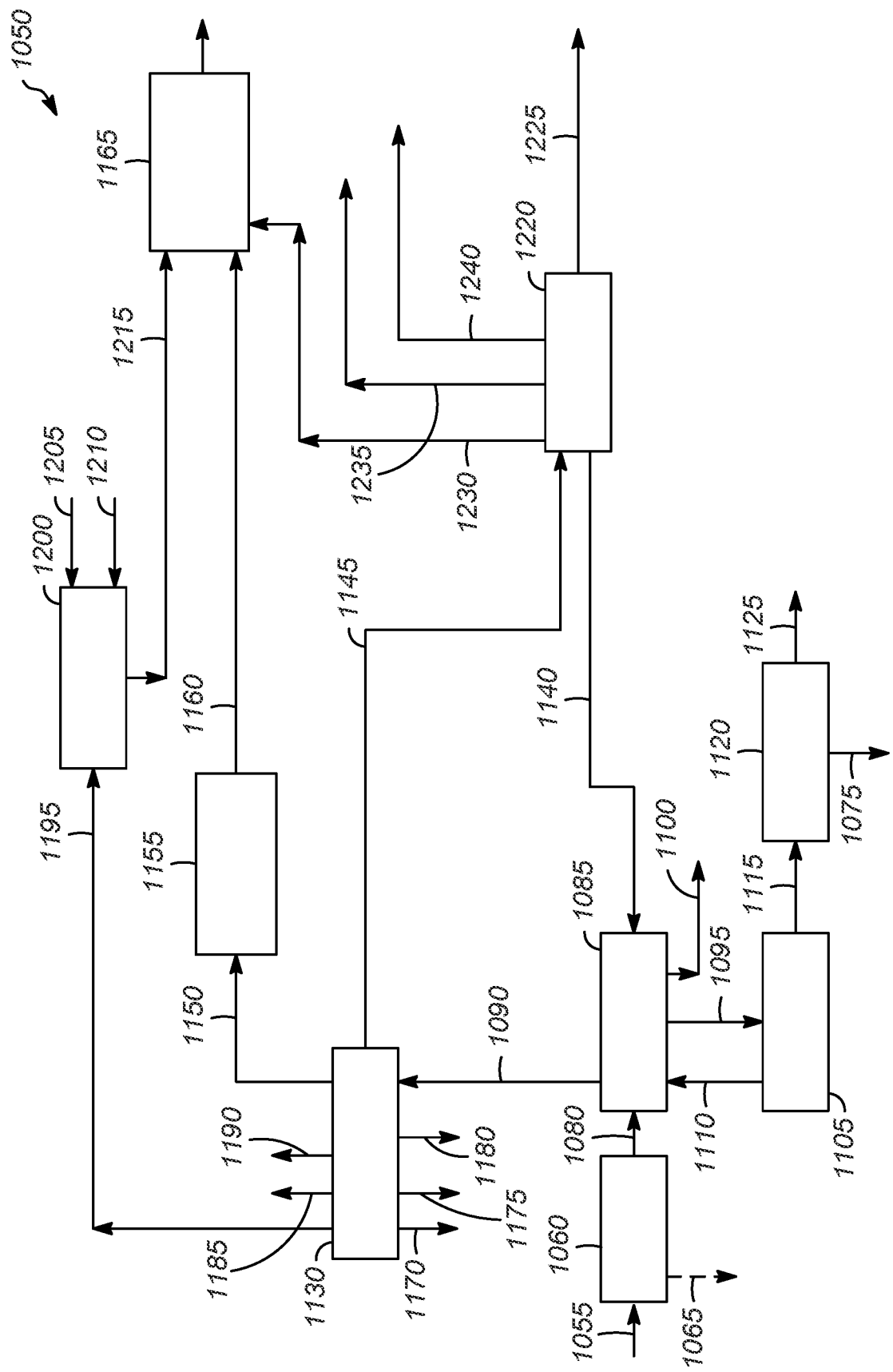
FIG. 9 is an illustration of one embodiment of a butane dehydrogenation complex with iso-butylene derivative process units.

FIG. 9 is a simplified illustration of a butane dehydrogenation complex 1050 including an iso-butylene derivative process unit.

The butane feed stream 1055 is sent to a feed preparation section 1060. Wash water purge stream 1065 is sent for disposal. Suitable disposal methods include chemical neutralization, wet air oxidation system, dilution, deep well injection, and waste water treatment.

A butane stream 1080 from the feed preparation section 1060 is sent to a de-isobutanizer (DIB) column 1085 for separation into an iso-butane stream 1090, an n-butane stream 1095, and a C5+ heavies purge stream 1100. The C5+ heavies purge stream 1100 may be blended with a product stream (depending on the vapor pressure and purity specifications), recycled to a refinery, or used as fuel. The n-butane stream 1095 is sent to a butane isomerization zone 1105. The isomerized butane stream 1110 is sent to the DIB column 1085. A butane isomerization off-gas stream 1115 is sent to a caustic scrubber 1120 to remove HCl. The scrubbed butane isomerization off-gas stream 1125 is sent to butane dehydrogenation section 1130 for recovery and recycle of butanes.

The iso-butane stream 1090 is sent to the butane dehydrogenation section 1130. The iso-1butylene product stream 1145 comprising iso-butylene and unreacted isobutane from the butane dehydrogenation section 1130 is sent to the iso-butylene derivative process unit 1220, as described further below.

The sulfidic spent caustic stream 1150 is sent to the spent sulfidic caustic treatment section 1155. The liquid effluent 1160 from the spent sulfidic caustic treatment section 1155 is sent to the waste water treatment plant 1165.

An aromatics rich spent solvent stream 1170 carrying washed down polynuclear aromatic heavies from the butane dehydrogenation section 1130, wash oil stream 1175, and heavies purge stream 1180 from the butane dehydrogenation section 1130, and a spent caustic stream 1075 used to neutralize HCl from a stripper in the caustic scrubber 1120, and a C5+ heavies purge stream 1100 from the bottoms of the DIB column 1085 are sent for disposal outside the complex as waste.

Excess net gas 1185 and excess tail gas 1190 from the butane dehydrogenation section 1130 is sent to a mixed fuel gas drum for use as fuel in heaters in the dehydrogenation process.

The catalyst regeneration vent gas stream 1195 is sent to the regeneration vent gas treatment section 1200. A NaOH stream 1205 and a NaHSO$_3$ stream 1210 are introduced into the regeneration vent gas treatment section 1200 to react with the chlorine and H$_2$S present in the catalyst regeneration vent gas stream 1195 forming a chloridic spent caustic stream 1215. The NaOH removes the HCl and H$_2$S by converting it to NaCl, NaHSO$_3$, Na$_2$SO$_3$, and Na$_2$SO$_4$, while the NaHSO$_3$ converts Cl$_2$ to HCl followed by reaction of NaOH with HCl to form NaCl. The chloridic spent caustic stream 1215 is sent to the waste water treatment plant 1165.

The iso-butylene product stream 1145 from the butane dehydrogenation section 1130 is sent to an iso-butylene derivative process unit 1220. The iso-butylene derivative process unit 1220 produces an iso-butylene derivative stream 1225 which is recovered. One or more additional streams are also produced. There can be one or more aqueous effluent streams 1230, one or more gaseous effluent streams 1235, and one or more rich hydrocarbon effluent streams 1240 (i.e., high calorific/low selling value streams having a heating value greater than 2500 BTU/lb). The aqueous effluent streams 1230 are sent to the waste water treatment plant 1165. The gaseous effluent streams 1235 are sent to a relief header if the flow is small (e.g., less than 0.5% iso-butylene rich stream). If the gaseous effluent streams 1235 are larger flow rates, they can be sent to a fuel gas drum. The rich hydrocarbon effluent streams 1240 are sent to the fuel network or disposal. An unreacted isobutane rich raffinate stream 1140 is sent to the DIB column 1085.

Figure 10A:
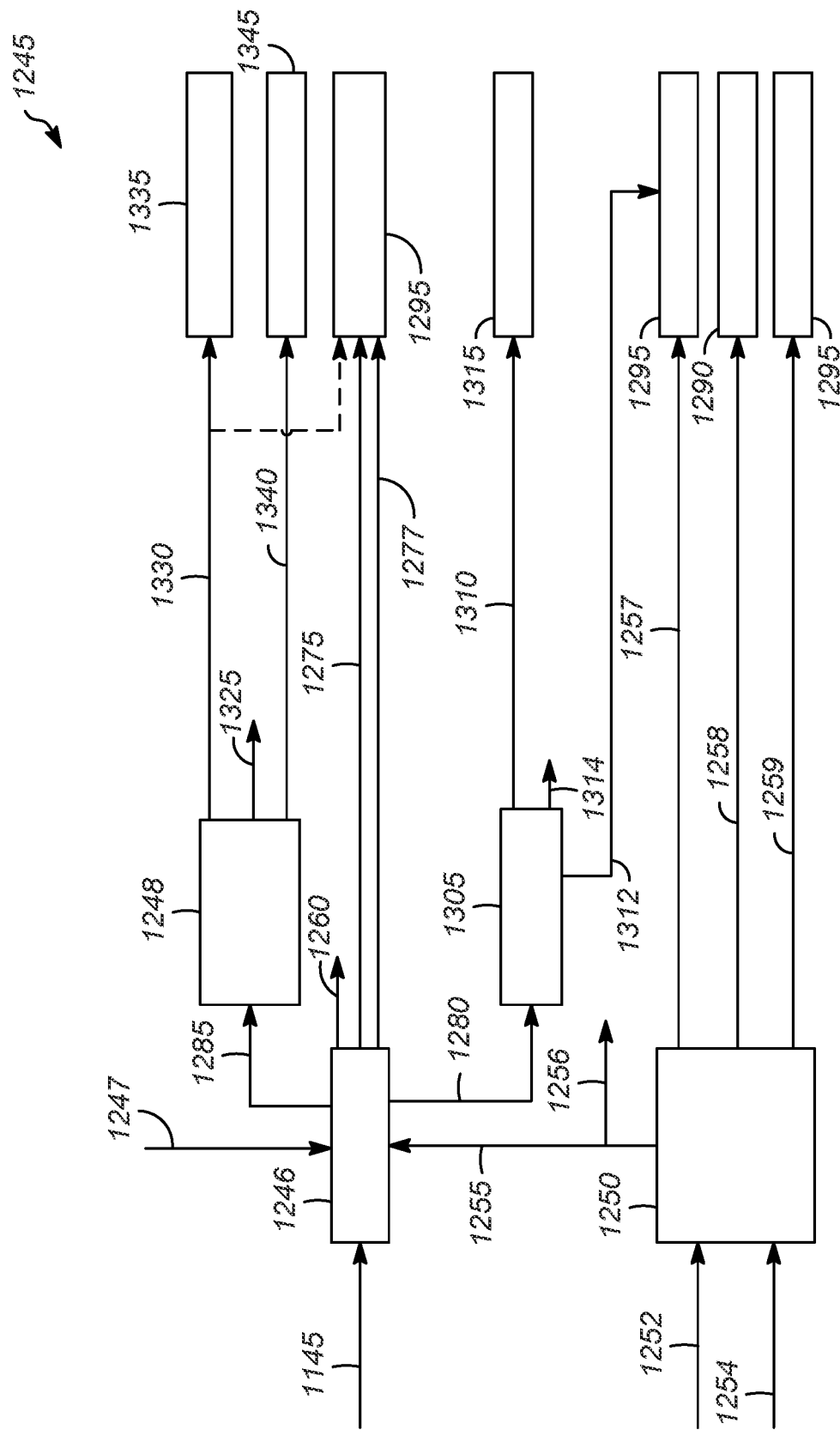
FIGS. 10A-10C are illustrations of embodiments of iso-butylene derivative process units.
Figure 10B:
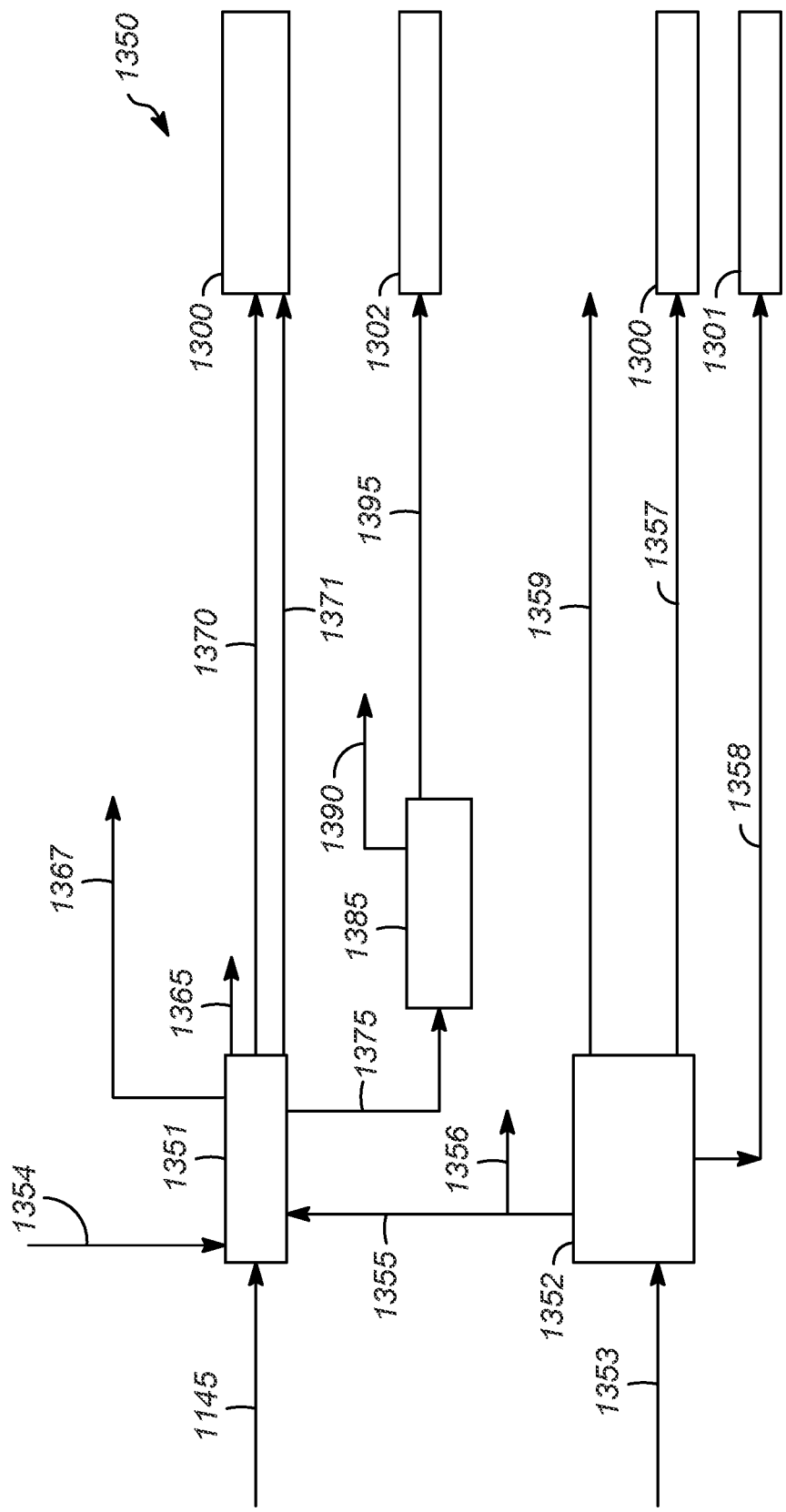
Figure 10C:
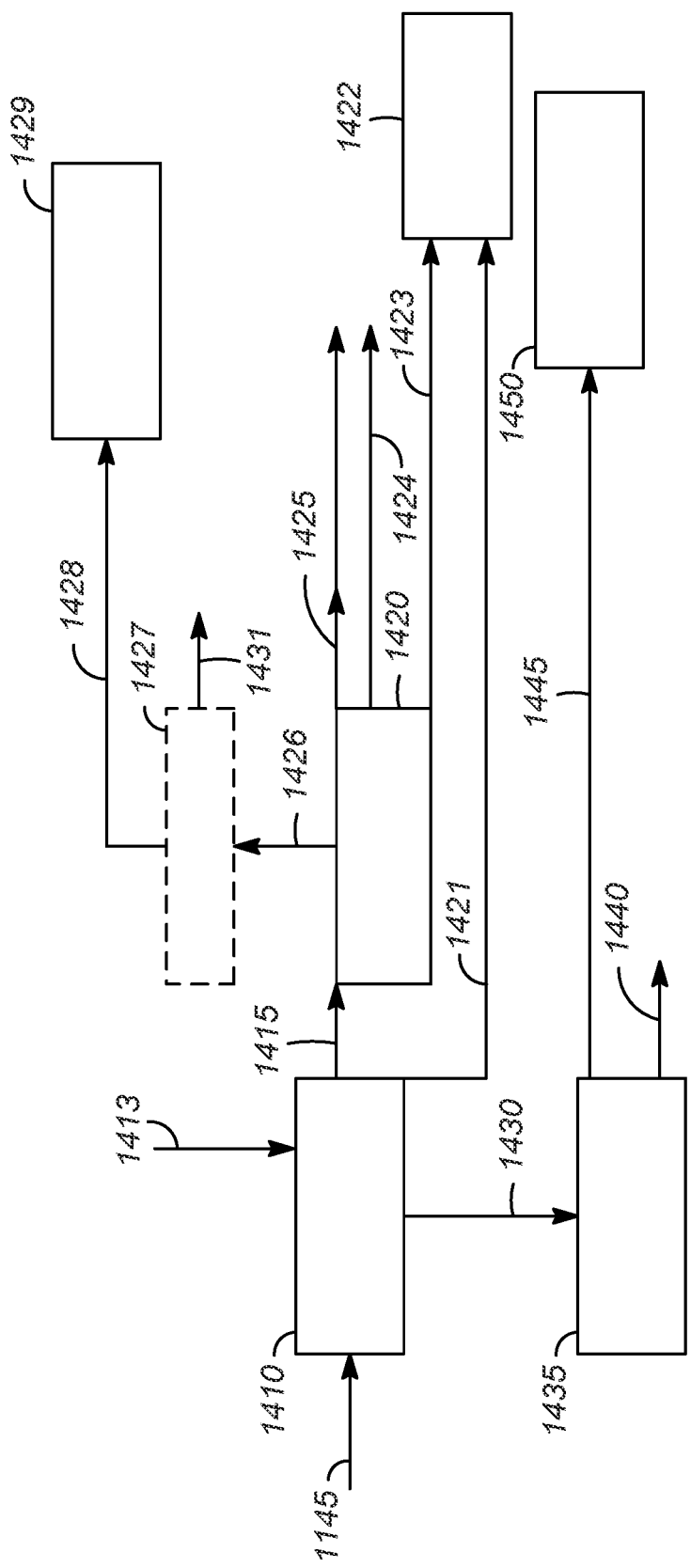

FIGS. 10A-C illustrate several iso-butylene derivative process units. FIG. 10A shows a methyl tert-butyl ether (MTBE)/high purity iso-butylene derivative process unit 1245. It includes an MTBE synthesis unit 1246, high purity iso-butylene process unit 1248, and methanol synthesis unit 1250.

A natural gas stream 1252 and steam stream 1254 are fed to a steam reformer in the methanol synthesis unit 1250 to produce synthesis gas which is then sent into the methanol synthesis reactor where crude methanol is produced. Crude methanol is then fractionated in a train of fractionators yielding methanol stream 1255. In some embodiments, a portion of the methanol stream 1255 can be recovered as methanol product stream 1256, if desired. A light ends purge MeOH stream 1258 and a fusel oil stream 1257 are also produced which are to be taken out from the system as waste streams. The light ends purge MeOH stream 1258 comprising MeOH is sent to relief header/fuel gas pool 1290. The fusel oil stream 1257 is sent to an effluent treatment plant 1295. A waste water effluent stream 1259 could also be generated which could be sent to effluent treatment plant 1295.

Methanol stream 1255, and iso-butylene product stream 1145, and make-up wash water stream 1247 are sent to the MTBE synthesis reactor in the MTBE synthesis unit 1246 to produce an MTBE product stream 1260. The unreacted C$_4$ hydrocarbon stream 1280, comprising mainly iso-butane, normal butane, and butenes with trace levels of oxygenates is sent to an oxygenate removal unit (ORU) 1305. In the ORU, unreacted C$_4$ hydrocarbon stream 1280 is fractionated to remove the light ends as an ORU off-gas stream 1310 which is sent to the relief header or fuel gas pool 1315, a very minor water stream 1312 which is sent to the effluent treatment plant 1295, and an oxygenated unreacted C$_4$ hydrocarbon stream 1314 which is recycled to the butane dehydrogenation section 1130.

A waste stream 1275 of spent alcohol-oily water stream and a MTBE waste water wash stream 1277 containing MTBE, acetone, and/or acrylonitrile are generated in the MTBE synthesis unit 1246 and sent to effluent treatment plant 1295.

A portion of the MTBE stream 1285 is sent to a high purity iso-butylene process unit 1248 to produce a high purity iso-butylene stream 1325 (typically greater than 99.9 wt % iso-butylene). Light ends purge MTBE stream 1330 comprising $C_4$ and $C_5$ hydrocarbons and water is sent to relief header/fuel gas network 1335 (and/or effluent treatment plant 1295, depending on the design). A heavies purge MTBE stream 1340 comprising predominantly tertiary butyl alcohol (TBA) and di-iso-butylene (DIB) is sent for disposal 1345.

FIG. 10B shows an ethyl tert-butyl ether (ETBE) derivative process unit 1350. It includes an ETBE synthesis unit 1351 and an ethanol synthesis unit 1352.

A bio-mass stream 1353 is sent to the ethanol synthesis unit 1352 which produces an ethanol stream 1355. Suitable sources of biomass include, but are not limited to, molasses, corn sugar, and beet sugar. A portion of the ethanol stream 1355 can be recovered as ethanol product stream 1356. Depending on the process adopted, the ethanol synthesis unit 1352 also produces one of more of a waste water stream 1357 which is sent to the effluent treatment plant 1300, a solid waste stream 1358 which can be a solid waste treatment facility 1301, and a fermenter vent gas stream 1359 which can be vented to the atmosphere.

The iso-butylene product stream 1145, ethanol stream 1355 from the ethanol synthesis unit 1352, and make-up wash water 1354 are reacted in the ETBE synthesis unit 1351 to produce an ETBE stream 1365. A rerun column bottoms stream 1367 (e.g., the heavies fraction from the MTBE process) is sent to fuel blending or storage. A waste stream 1370 of spent alcohol-oily water, and a water wash ETBE stream 1371 comprising ETBE are also produced and sent for treatment in the effluent treatment plant 1300.

The unreacted isobutane and iso-butylene stream 1375 which contains oxygenates is sent to the oxygenate removal unit (ORU) 1385 to produce an isobutane rich stream 1390 and an ORU off-gas stream 1395. The isobutane rich raffinate stream 1390 is recycled back to the DIB column 1085. The ORU off-gas stream 1395 is sent to relief header or fuel gas pool 1302.

FIG. 10C illustrates an alkylate derivative process unit 1405. The iso-butylene product stream 1145 is sent to an indirect alkylation reaction section 1410 to produce an iso-octene stream 1415. The iso-octene stream 1415 is hydrogenated in a hydrogenation section 1420 to produce an alkylate stream 1425. There is a water wash ETBE waste stream 1421 comprising ETBE, acetone, and/or acrylonitrile which is sent to the waste water treatment plant 1422. The sour water stream 1423 is also sent to the waste water treatment plant 1422. A heavies stream 1424 is sent to fuel blending or storage. In some embodiments, there is a hydrogenation off-gas stream 1426 which is sent to an optional sulfur removal unit 1427 which produces an $H_2S$ containing off-gas stream 1428 which is sent to relief header 1429. Sulfur free off-gas stream 1431 is sent to the fuel gas system. An oxygenate stream 1430 is sent to an oxygenate removal unit (ORU) 1435 which produces an isobutane stream 1440 and an ORU off-gas stream 1445. The isobutane stream 1440 is recycled to the DIB column 1085. The ORU off-gas stream 1445 is sent to relief header or fuel gas pool 1450.

Figure 11:
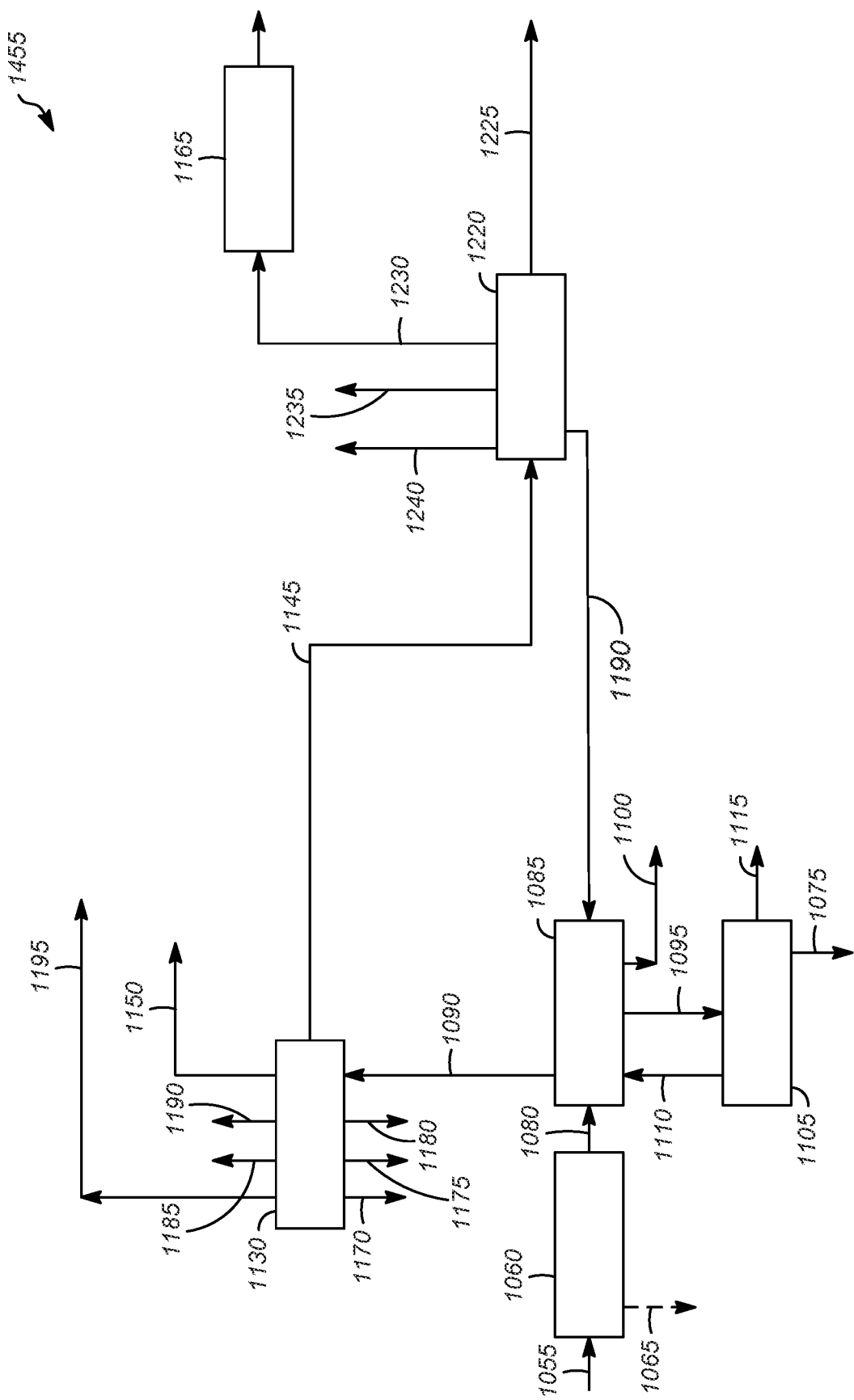
FIG. 11 is an illustration of a portion of one embodiment of a butane dehydrogenation complex with iso-butylene derivative process units according to the present invention.

FIGS. 11, 12A-12C illustrate the same basic butane dehydrogenation complex 1455 shown in FIGS. 9 and 10A-10C according to the present invention. As shown in FIG. 11, the spent sulfidic caustic treatment section and the regeneration vent gas treatment section have been eliminated. As a result, there is no liquid effluent from the spent sulfidic caustic treatment section or chloridic spent caustic stream to be sent to the waste water treatment plant 1165.

Figure 13:
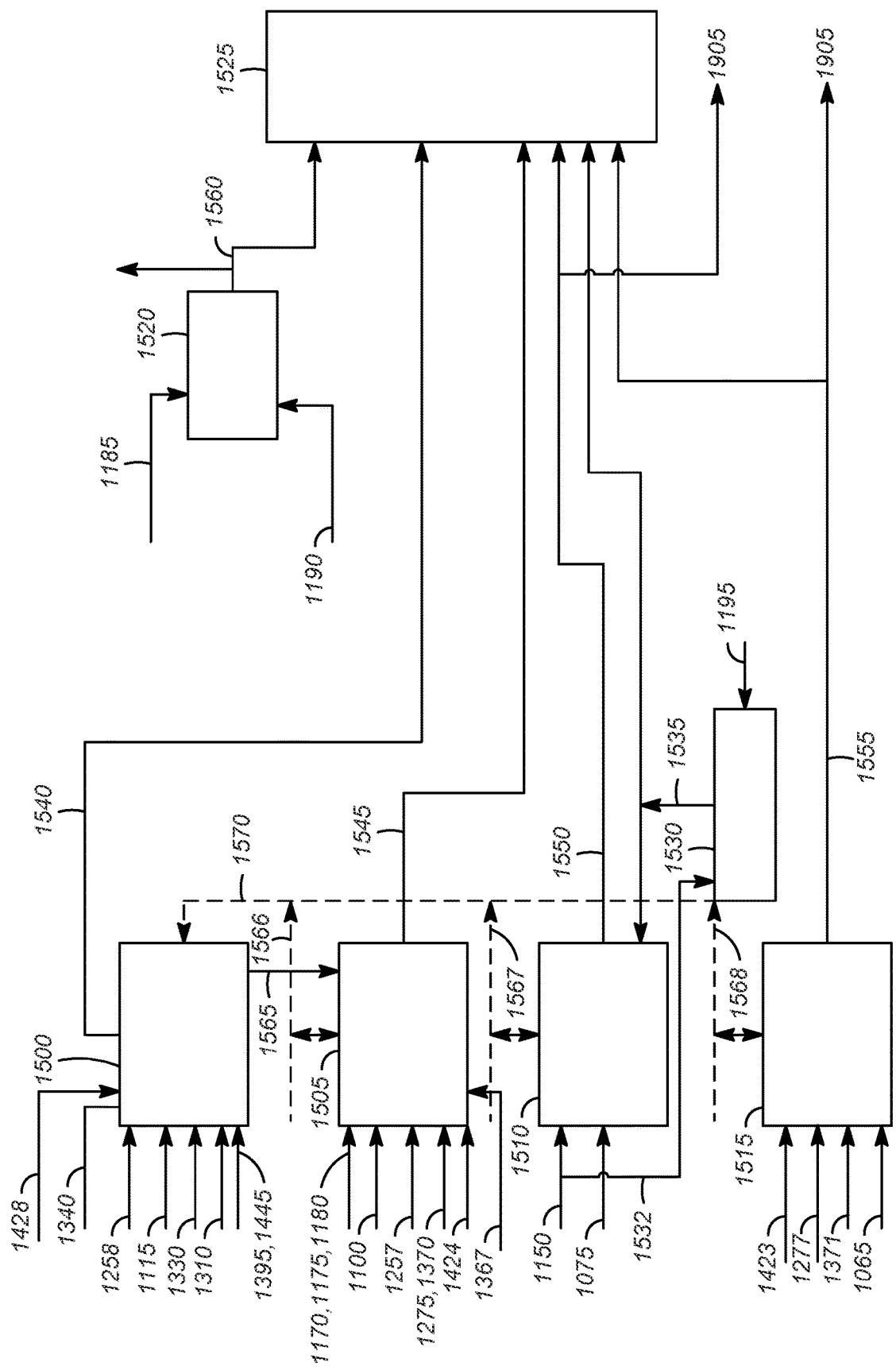
FIG. 13 is an illustration of another portion of the butane dehydrogenation complex with iso-butylene derivative process units of FIGS. 11 and 12A-12C according to the present invention.

As shown in FIG. 13, the process includes an off-gas knockout drum 1500, a hydrocarbon buffer vessel 1505, a spent caustic buffer vessel 1510, a waste water buffer vessel 1515, a fuel gas knockout drum 1520, and a thermal oxidation system 1525.

As shown in FIGS. 11 and 13, the wash water purge stream 1065 from the feed preparation section 1060 is sent to the waste water buffer vessel 1515. The spent caustic stream 1075 from the feed preparation section 1060 is sent to the spent caustic buffer vessel 1510. The sulfidic spent caustic stream 1150 from the butane dehydrogenation section 1130 is sent to the spent caustic buffer vessel 1510. The aromatics rich spent solvent stream 1170, wash oil stream 1175, and heavies purge stream 1180 from the butane dehydrogenation section 1130 are sent to the hydrocarbon buffer vessel 1505. The excess net gas 1185 and excess tail gas 1190 from the butane dehydrogenation section 1130 are sent to the fuel gas knockout drum 1520. The catalyst regeneration vent gas stream 1195 from the butane dehydrogenation section 1130 is sent to the conditioning section 1530. A slip stream 1532 from the sulfidic spent caustic stream 1150 can be sent to the conditioning section 1530 for temperature reduction. The conditioned catalyst regeneration vent gas stream 1535 can be sent directly to the thermal oxidation system 1525 or to the spent caustic buffer vessel 1510. The C5+ heavies purge stream 1100 is sent to the hydrocarbon buffer vessel 1505. The butane isomerization off-gas stream 1115 from the butane isomerization zone 1105 is sent to the off-gas knockout drum 1500.

The aqueous effluent stream(s) 1230 are sent to the waste water treatment plant 1165. The treatment of the gaseous effluent streams 1235 and rich hydrocarbon effluent streams 1240 from the iso-butylene derivative process units 1220 will discussed below with respect to each derivative process unit.

Figure 12A:
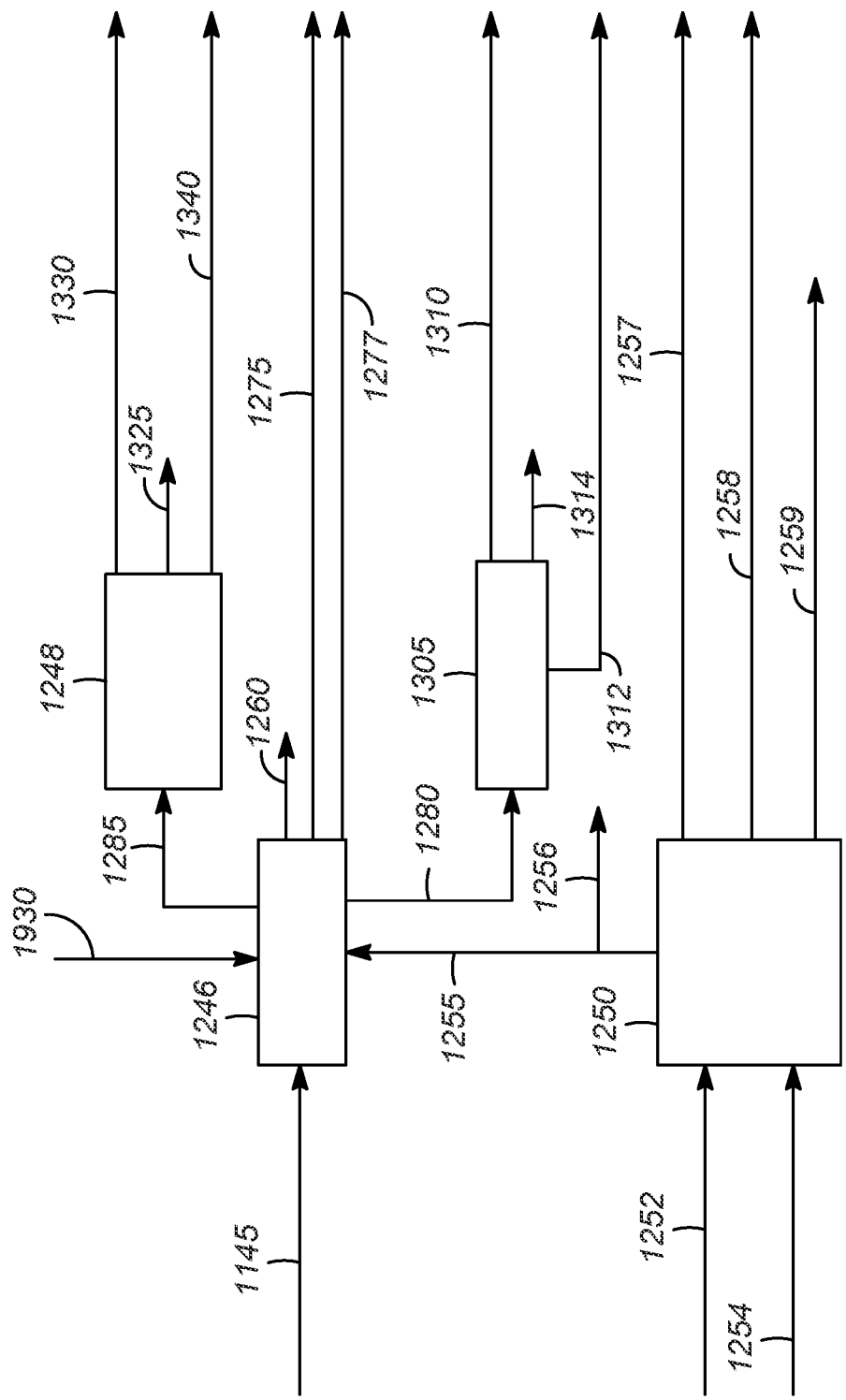
FIGS. 12A-12C are illustrations of embodiments of iso-butylene derivative process units according to the present invention.

As shown in FIGS. 12A and 13, for the MTBE/high purity iso-butylene derivative process unit 1460, connections to the relief header/fuel gas pool, effluent treatment plant, and disposal are removed. The light ends purge MTBE stream 1330, and the heavies purge MTBE stream 1340 from the high purity iso-butylene process unit 1248 are sent to the off-gas knockout drum 1500. The ORU off-gas stream 1310 from the ORU 1305 is sent to the off-gas knockout drum 1500. The waste stream 1275 of spent alcohol/oily water from the MTBE synthesis unit 1246 is sent the hydrocarbon buffer vessel 1505. The MTBE waste water wash stream 1277 is sent to the waste water buffer vessel 1515, along with water stream 1312. The light ends purge MeOH stream 1258 is sent to the off-gas knockout drum 1500. The fusel oil stream 1257 from the methanol synthesis unit 1250 is sent the hydrocarbon buffer vessel 1505.

Figure 12B:
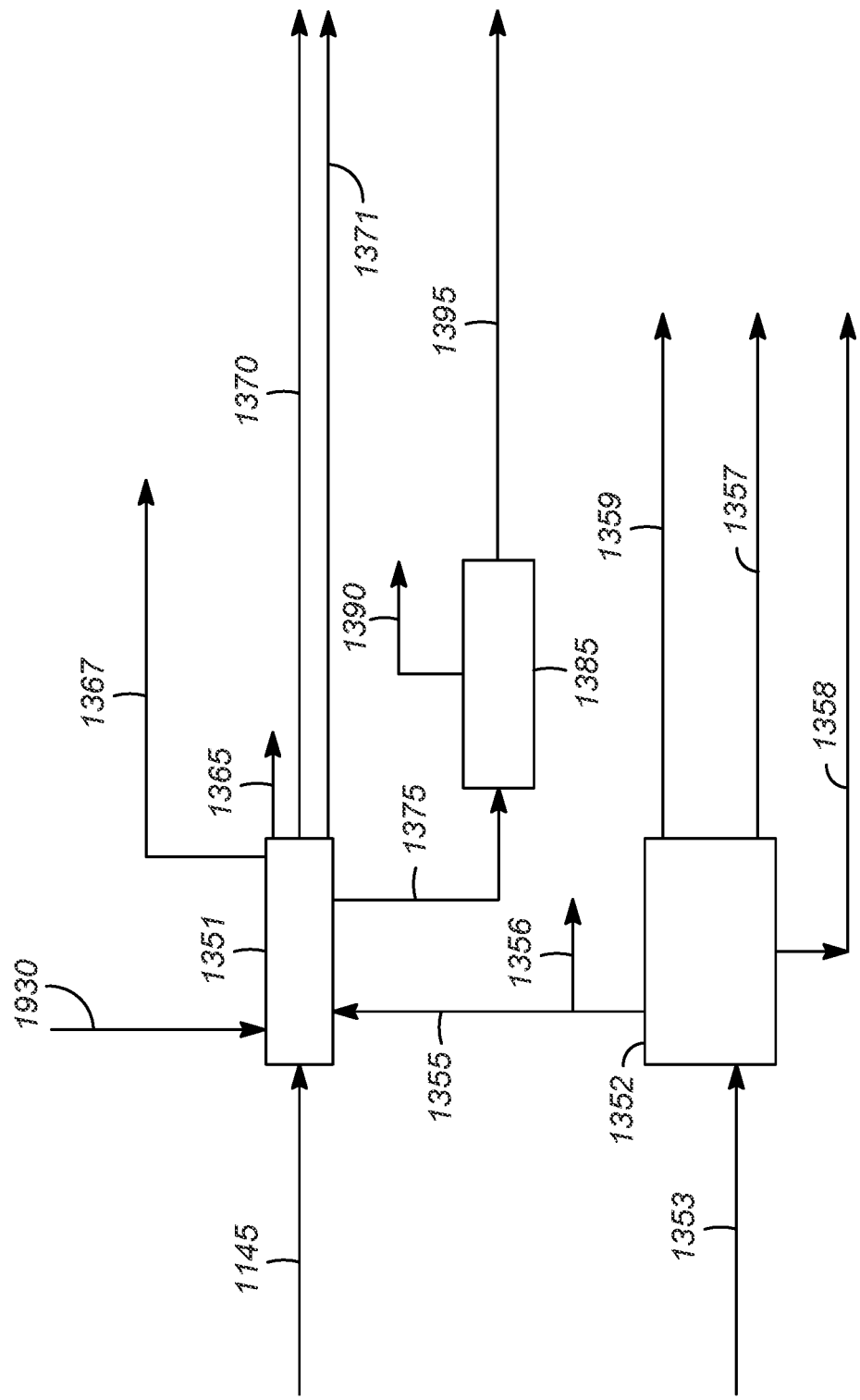

As shown in FIGS. 12B and 13, in the ETBE derivative process unit 1465, connections to the relief header/fuel gas pool and disposal/effluent treatment plant are removed. The waste stream 1370 of spent alcohol/oily water from the ETBE synthesis unit 1351 is sent the hydrocarbon buffer vessel 1505. The water wash ETBE stream 1371 is sent to the waste water buffer vessel 1515. The ORU off-gas stream 1395 from the ORU 1385 is sent to the off-gas knockout drum 1500. The rerun column bottoms stream 1367 is sent to the hydrocarbon buffer vessel 1505.

Figure 12C:
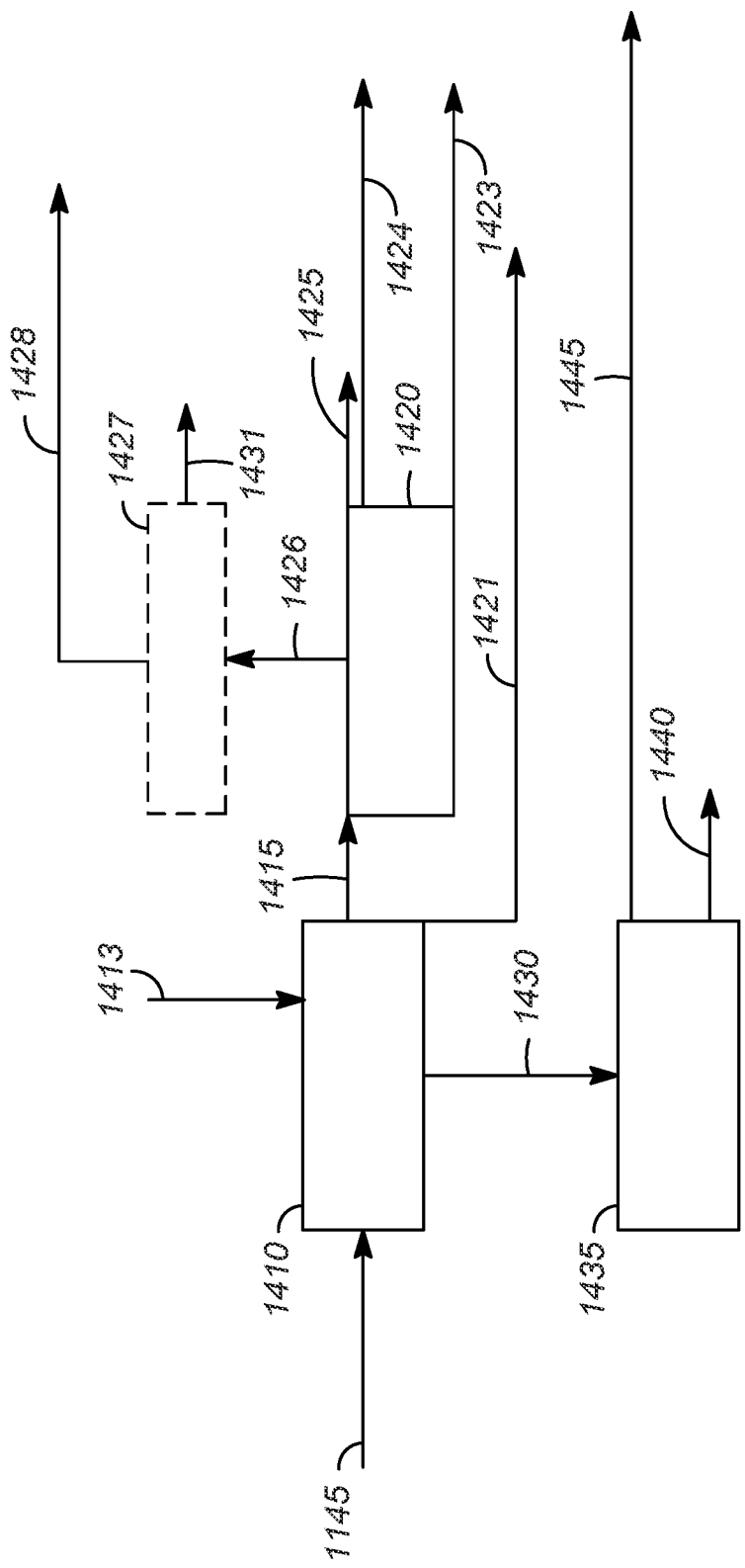

As shown in FIGS. 12C and 13, in the alkylate derivative process unit 1470, connection to the relief header/fuel gas pool are removed. The ORU off-gas stream 1445 from the ORU 1435 is sent to the off-gas knockout drum 1500. The water wash ETBE waste stream 1421 and the sour water stream 1423 are sent to the waste water buffer vessel 1515. The heavies stream 1424 is sent to the hydrocarbon buffer vessel 1505.

An off-gas stream 1540 from the off-gas knockout drum 1500, a liquid hydrocarbon stream 1545 from the hydrocarbon buffer vessel 1505, a spent caustic stream 1550 from the spent caustic buffer vessel 1510, a waste water stream 1555 from the waste water buffer vessel 1515, and a fuel gas stream 1560 from the fuel gas knockout drum 1520 are sent to the thermal oxidation system 1525.

A liquid condensable stream 1565 can be sent from the off-gas knockout drum 1500 to the hydrocarbon buffer vessel 1505.

The hydrocarbon buffer vessel 1505, the spent caustic buffer vessel 1510, and the waste water buffer vessel 1515 can be operated with a push/pull system using liquefied petroleum gas/waste gas/fuel gas to maintain a constant pressure. There is a vent gas stream 1566, 1567, 1568 into and out of each of the hydrocarbon buffer vessel 1505, the spent caustic buffer vessel 1510, and the waste water buffer vessel 1515 to maintain a constant pressure. When the pressure is high, gas will be pushed out of the hydrocarbon buffer vessel 1505, the spent caustic buffer vessel 1510, and the waste water buffer vessel 1515, while it will be pulled into the hydrocarbon buffer vessel 1505, the spent caustic buffer vessel 1510, and the waste water buffer vessel 1515 when the pressure is low via the waste gas/fuel gas supply line 1570.

Figure 14:
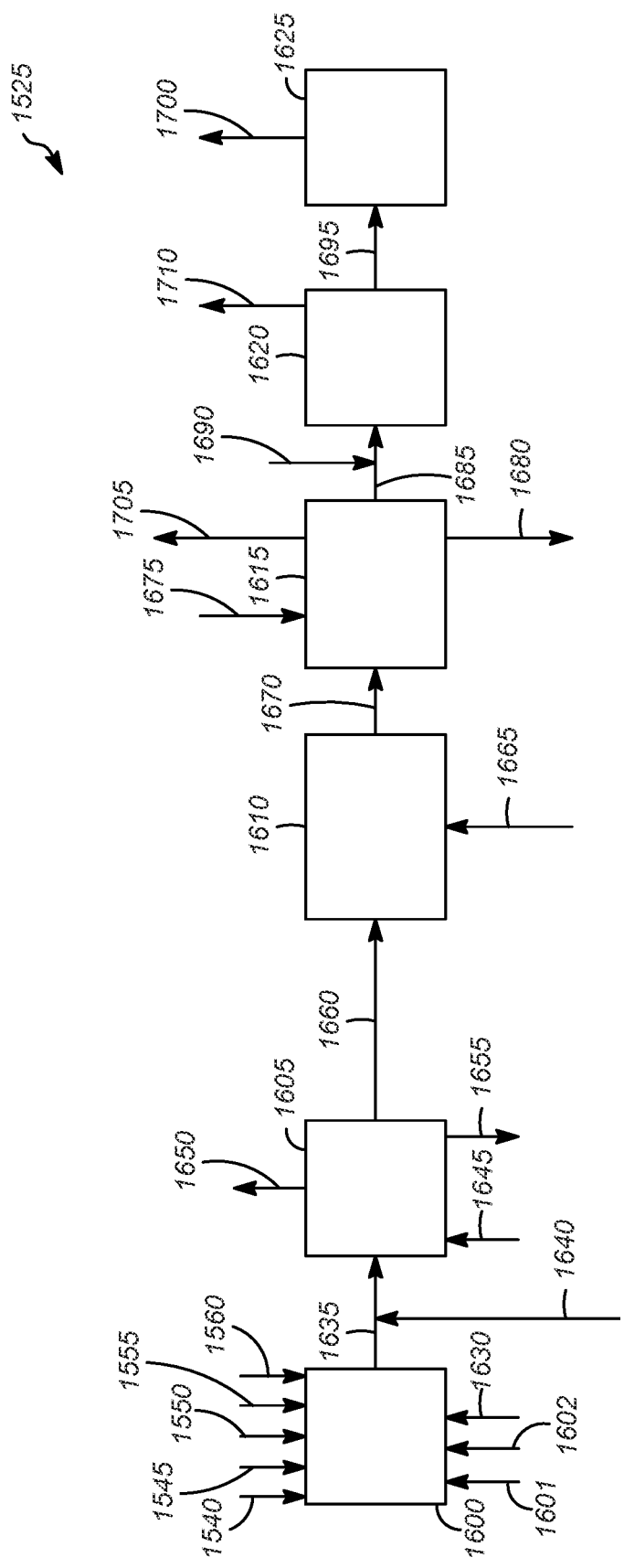
FIG. 14 is an illustration of one embodiment of a thermal oxidation system according to the present invention.

One embodiment of a thermal oxidation system 1525 is illustrated in FIG. 14. The thermal oxidation system 1525 comprises a thermal oxidizing section 1600, an optional waste heat recovery section 1605, a quench/particulate removal section 1610, a SOx removal section 1615, an optional NOx removal section 1620, and an optional dioxin-furan removal section 1625.

At least one of the off-gas stream 1540 from the off-gas knockout drum 1500, the liquid hydrocarbon stream 1545 from the hydrocarbon buffer vessel 1505, the spent caustic stream 1550 from the spent caustic buffer vessel 1510, the waste water stream 1555 from the waste water buffer vessel 1515, and the fuel gas stream 1560 from the fuel gas knockout drum 1520 are sent to the thermal oxidation system 1525, along with a combustion air stream 1630, natural gas/fuel gas stream 1601 and quench air stream 1602.

The inlet temperature of the thermal oxidizing section 1600 is typically in the range of −30-500° C. with a pressure of −1 kPa(g) to 3000 kPa(g). The outlet temperature is typically in the range of 650-1300° C. with a pressure of −1 kPa(g) to 50 kPa(g). The residence time in the thermal oxidizing section 1600 is between 0.5 and 2 seconds. Any suitable thermal oxidizing section 1600 could be used. The thermal oxidizing section 1600 can be forced draft, induced draft, or a combination of both. An optional selective non-catalytic reduction (SNCR) section may be present in some cases. The inlet temperature of the SNCR section is typically in the range of 650-1300° C. with a pressure of −1 kPa(g) to 50 kPa(g). The outlet temperature is typically in the range of 650-1040° C. with a pressure of −1 kPa(g) to 50 kPa(g). The residence time in the SNCR section is between 0.2 and 1 seconds. The thermal oxidation step would be separated from the SNCR step via a choke wall in the vessel. The hydrocarbons are converted to $H_2O$ and $CO_2$. The sulfides from the sulfur species (e.g. $H_2S$) present in feed are converted to oxidized sulfur particulate SOx including, but not limited to, $SO_2$ and $SO_3$, and $H_2O$. The nitrogen from the nitrogen bound molecules (e.g. $NH_3$, di-ethanol urea (DEU), di-ethanol amine (DEA), and mono-ethanol amine (MEA)) present in the feed are converted to nitrogen ($N_2$) and NOx, including but not limited to NO, $NO_2$. The HCl and $Cl_2$ remain.

The flue gas 1635 from the thermal oxidizing section 1600 consists essentially of one or more of $H_2O$, $Na_2CO_3$, $Na_2SO_3$, $Na_2SO_4$, $CO_2$, $N_2$, $O_2$, SOx, (i.e., $SO_2$ and $SO_3$), NOx, (i.e., NO and $NO_2$), NaCl, HCl, $Cl_2$, dioxins, and furans. "Consisting essentially of" means that one of more of the gases, vapors, or liquids are present and there are no other gases, vapors, or liquids present which require treatment before being released to the atmosphere. The flue gas 1635 is quenched with quench stream 1640 to solidify salts, including NaCl, $Na_2CO_3$, $Na_2SO_3$, and $Na_2SO_4$. Suitable quench streams include but are not limited to air, water, flue gas, and combinations thereof.

The flue gas 1635 may be sent to the optional waste heat recovery section 1605. The inlet temperature of the optional waste heat recovery section 1605 is typically in the range of 650-800° C. with a pressure of −2 kPa(g) to 50 kPa(g). The outlet temperature is typically in the range of 200-400° C. with a pressure of −2 kPa(g) to 50 kPa(g). Suitable waste heat recovery apparatus and methods include, but are not limited to, a waste heat recovery boiler, including, but not limited to, a firetube boiler or a watertube boiler. Boiler feed water or oil stream 1645 enters the waste heat recovery section 1605 where a portion is converted to steam or hot oil 1650, with the remainder exiting as blowdown water or oil 1655. In some cases, the steam can be converted to electricity, for example using a steam turbine, if desired.

The recovered waste heat from steam or hot oil 1650 can be in the form of low (e.g., less than 350 kPa(g)), medium (e.g., 350 kPa(g) to 1750 kPa(g)), or high (e.g., greater than 1750 kPa(g)) pressure saturated or superheated steam, hot oil, and/or electricity. The recovered heat can be used to provide heat to one or more pieces of equipment or process streams in the propane/butane dehydrogenation complex or to other parts of the plant. For example, the recovered waste heat from steam or hot oil 1650 can be used in reboilers in the fractionation section of the propane dehydrogenation unit or the butene column in the butane dehydrogenation unit, or for other heat requirements.

The flue gas 1660 from the optional waste heat recovery section 1605 flows to the quench/particulate removal section 1610 where the temperature of the flue gas is reduced to the saturation temperature using quench stream 1665. The inlet temperature of the quench/particulate removal section 1610 is typically in the range of 200-1300° C. with a pressure of −40 kPa(g) to 50 kPa(g). The outlet temperature is typically in the range of 45-150° C. with a pressure of −41 kPa(g) to 50 kPa(g).

When a caustic or $NH_3$ scrubbing section is used, in addition to quenching the flue gas 1660, particulate removed from the flue gas in the quench section is captured in the scrubber sump, and removed from the system via a continuous aqueous stream 1680. When a caustic scrubber is used, the quench section will be a venturi scrubber. The venturi scrubber cools the flue gas to adiabatic saturation temperature (50-150° C.) to allow proper SOx scrubbing (the pressure drop required over the venturi scrubber for quench only is 0-50 mBar). Due to the treatment of spent caustic, and hence particulate generation (NaCl, $Na_2CO_3$, $Na_2SO_3$, $Na_2SO_4$), the quench will also act as a particulate removal device. When particulate removal is also required, the pressure drop will be the sum of the 0-50 mBar pressure drop for the gas quenching plus a pressure drop of 0-330 mBar for particulate removal, and the total pressure drop range will be 0-380 mBar (0.38 Bar). Quench stream 1665 includes, but is not limited to, water, air, recycle flue gas, or combinations thereof.

The quenched flue gas 1670 from the quench/particulate removal section 1610 is sent to the SOx removal section 1615 for removal of at least one of the SOx, HCl and $Cl_2$. The inlet temperature of the SOx removal section 1615 is typically in the range of 45-150° C. with a pressure of −41 kPa(g) to 50 kPa(g). The outlet temperature is typically in the range of 45-150° C. with a pressure of −41 kPa(g) to 50 kPa(g). For example, the SOx removal section 1615 could be a scrubbing section in which a stream 1675 comprising aqueous NaOH is introduced into the SOx removal section 1615 where it reacts with at least one of the SOx, HCl, and $Cl_2$ in the flue gas. The reaction takes place at a temperature in the range of 50-150° C. An aqueous stream 1680 containing aqueous $H_2O$, $Na_2SO_3$, $Na_2SO_4$, $NaHSO_3$, $Na_2CO_3$, and NaCl exits the scrubbing section. If desired, a reducing agent such as $NaHSO_4$ or $H_2O_2$, can be included to react with the $Cl_2$ to form HCl which reacts to form NaCl. Alternatively, stream 1675 could be an $NH_3$ based solution. $NH_3$ based solutions include aqueous and anhydrous $NH_3$. The $NH_3$ reacts with the SOx to form $(NH_4)_2SO_4$. The $NH_3$ reacts with the $Cl_2$ to form $N_2$ and HCl, followed by the reaction of the HCl with the $NH_3$ forming $NH_4Cl$. A separate reducing agent is not needed when $NH_3$ is used. In this case, the aqueous stream 1680 would include $H_2O$, $Na_2SO_3$, $Na_2SO_4$, $NaHSO_3$, $Na_2CO_3$, NaCl, $(NH_4)_2SO_4$, and $NH_4Cl$. Alternatively, a wet electrostatic precipitator (WESP) could be used. This allows ultra-low particulate removal, e.g., below 30 mg/$Nm^3$. This is not achievable using a conventional scrubber.

The de-SOx outlet flue gas stream 1685 from the SOx removal section 1615 has a reduced level of SOx, HCl and $Cl_2$ compared to the incoming quenched flue gas 1670. The de-SOx outlet flue gas stream 1685 comprises one or more of $H_2O$, $CO_2$, $N_2$, $O_2$, NOx, dioxins, and furans.

If NOx is present in the de-SOx outlet flue gas stream 1685, the de-SOx outlet flue gas stream 1685 is sent to the optional NOx removal section 1620 to remove NOx. The inlet temperature of the NOx removal section 1620 is typically in the range of 150-300° C. with a pressure of −42 kPa(g) to 50 kPa(g). The outlet temperature is typically in the range of 200-350° C. with a pressure of −42 kPa(g) to 50 kPa(g). The de-SOx outlet flue gas stream 1685 may need to be heated to obtain the desired inlet temperature for the NOx removal section 1620. For example, the NOx removal section 1620 can be a selective catalytic reduction (SCR) section in which an ammonia and/or urea stream 1690 is introduced into the SCR section where it reacts with the NOx and forms $N_2$ and $H_2O$. Any suitable SCR catalyst could be used, including but not limited to, ceramic carrier materials such as titanium oxide with active catalytic components such as oxides of base metals including $TiO_2$, $WO_3$ and $V_2O_5$, or an activated carbon based catalyst. The de-NOx outlet flue gas stream 1695 comprises one or more of $H_2O$, $CO_2$, $N_2$, $O_2$, dioxins, and furans.

If there are any halogens present in the feed, this may result in the formation of dioxin and/or furans. These compounds must be removed before the gases can be vented to the atmosphere. If dioxins and/or furans are present in the de-SOx outlet flue gas stream 1685 or the de-NOx outlet flue gas stream 1695, the de-SOx outlet flue gas stream 1685 or the de-NOx outlet flue gas stream 1695 is sent to the optional dioxin-furan removal section 1625 for removal of the dioxin and/or furan. The dioxin and furans can be removed using a catalyst. The inlet temperature of the dioxin-furan removal section 1625 is typically in the range of 150-250° C. with a pressure of −43 kPa(g) to 50 kPa(g). The outlet temperature is typically in the range of 150-250° C. with a pressure of −43 kPa(g) to 50 kPa(g). The treated outlet flue gas 1700, consisting essentially of one or more of $H_2O$, $CO_2$, $N_2$, and $O_2$, can be vented to the atmosphere.

If the levels of NOx and dioxins and/or furans in the de-SOx outlet flue gas stream 1685 exceed environmental regulations, the system will probably contain both the NOx removal section 1620 and dioxin-furan removal section 1625. In this case, de-SOx outlet flue gas stream 1685 will have a slightly higher temperature than de-NOx outlet flue gas stream 1695. There may be a need for quenching the de-NOx outlet flue gas stream 1695 before it enters the dioxin-furan removal section 1625.

If the de-SOx outlet flue gas stream 1685 does not contain NOx, dioxin, or furans, the optional NOx removal section 1620 and optional dioxin-furan removal section 1625 are not present. The scrubbed flue gas 1705 from the SOx removal section 1615, consisting essentially of one or more of $H_2O$, $CO_2$, $N_2$, and $O_2$, can be vented to the atmosphere.

If the de-SOx outlet flue gas stream 1685 contains NOx, but no dioxin or furans, the optional dioxin-furan removal section 1625 is not present. The de-NOx outlet flue gas 1710 from the NOx removal section 1620, consisting essentially of one or more of $H_2O$, $CO_2$, $N_2$, and $O_2$, can be vented to the atmosphere.

If the de-SOx outlet flue gas stream 1685 contains dioxin or furans, but not NOx, the optional NOx removal section 1620 is not present. The de-SOx outlet flue gas stream 1685 is sent to the optional dioxin-furan removal section 1625. The treated outlet flue gas 1700, consisting essentially of one or more of $H_2O$, $CO_2$, $N_2$, and $O_2$, can be vented to the atmosphere.

Figure 15:
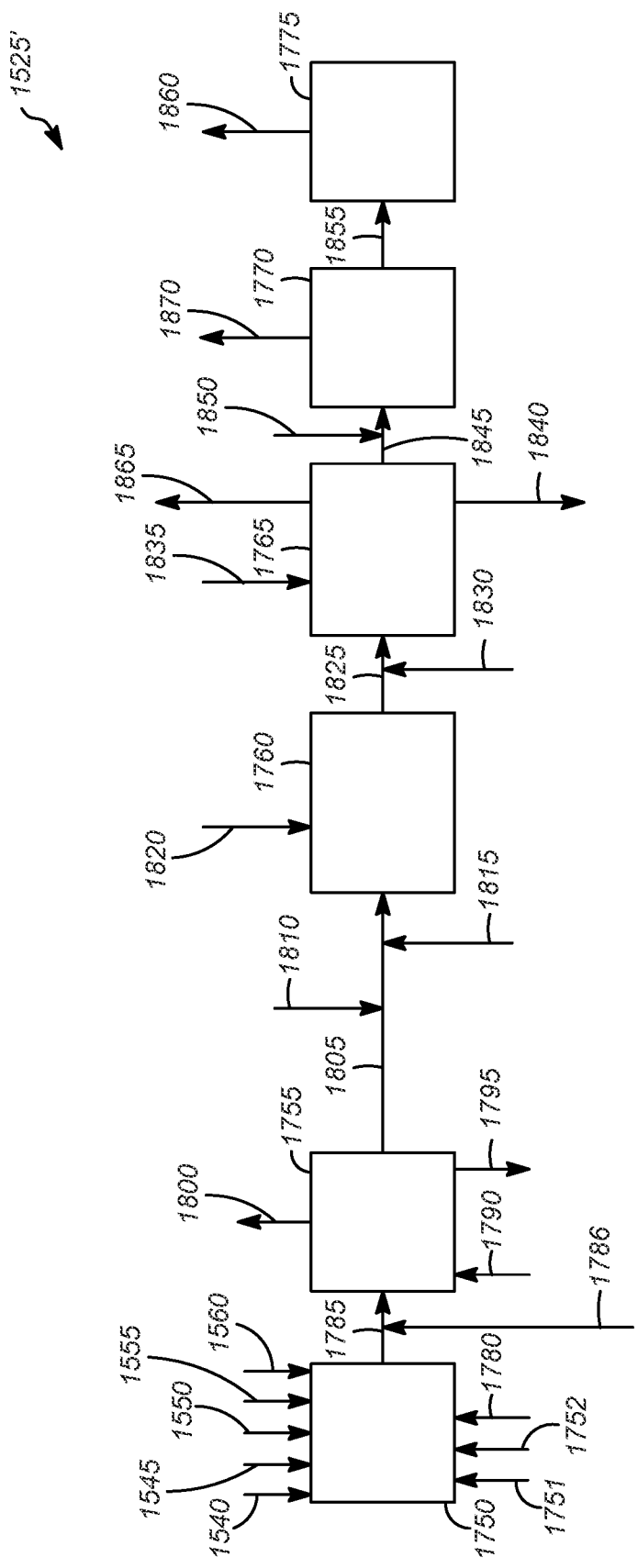
FIG. 15 is an illustration of another embodiment of a thermal oxidation system according to the present invention.

Another embodiment of the thermal oxidation system 1525' is illustrated in FIG. 15. The thermal oxidation system 1525' comprises a thermal oxidizing section 1750, an optional waste heat recovery section 1755, a dry residue reaction section 1760, a filtration section 1765, an optional NOx removal section 1770, and an optional dioxin-furan removal section 1775.

At least one of the off-gas stream 1540 from the off-gas knockout drum 1500, the liquid hydrocarbon stream 1545 from the hydrocarbon buffer vessel 1505, the spent caustic stream 1550 from the spent caustic buffer vessel 1510, the waste water stream 1555 from the waste water buffer vessel 1515, and the fuel gas stream 1560 from the fuel gas knockout drum 1520 are introduced into the thermal oxidizing section 1750, along with a combustion air stream 1780, natural gas/fuel gas stream 1751, and quench stream 1752.

The inlet temperature of the thermal oxidizing section 1750 is typically in the range of −30-500° C. with a pressure of −1 kPa(g) to 3000 kPa(g). The outlet temperature is typically in the range of 650-1300° C. with a pressure of −1 kPa(g) to 50 kPa(g). The residence time in the thermal oxidizing section 1750 is between 0.5 and 2 seconds. Any suitable thermal oxidizing section 1750 could be used. The thermal oxidizing section 1750 can be forced draft, induced draft, or a combination of both. The inlet temperature of the optional SNCR section is typically in the range of 650-1300° C. with a pressure of −1 kPa(g) to 50 kPa(g). The outlet temperature is typically in the range of 650-1040° C. with a pressure of −1 kPa(g) to 50 kPa(g). The residence time in the SNCR section is between 0.2 and 1 seconds. The thermal oxidation step would be separated from the SNCR step via a choke wall in the vessel.

The flue gas 1785 from the thermal oxidizing section 1750 consists essentially of one or more of $H_2O$, $CO_2$, $N_2$, $O_2$, SOx, NOx, HCl, $Cl_2$, dioxins, and furans. The flue gas 1785 is sent to the optional waste heat recovery section 1755. Boiler feed water or oil stream 1790 enters the waste heat recovery section 1755 where a portion is converted to steam or hot oil, with reminder exiting as blowdown water or oil 1795. Suitable waste heat recovery apparatus and methods are described above. The recovered waste heat 1800 can be in the form of low, medium, or high pressure saturated or superheated steam, hot oil, and/or electricity. The recovered waste heat 1800 can be used in reboilers in the fractionation section of the propane dehydrogenation unit or the butene column in the butane dehydrogenation unit, or elsewhere in the plant, or for other heat requirements.

The flue gas 1785 may be quenched with quench stream 1786. Suitable quench streams include but are not limited to air, water, flue gas, and combinations thereof.

The flue gas stream 1805 from the waste heat recovery section 1755 is sent to the dry residue reaction section 1760 to convert at least one of SOx, HCl and $Cl_2$. The inlet temperature of the dry residue reaction section 1760 is typically in the range of 200-400° C. with a pressure of −3 kPa(g) to 50 kPa(g). The outlet temperature is typically in the range of 200-400° C. with a pressure of −3 kPa(g) to 50 kPa(g). Fresh dry sorbent 1810 and optionally recycled sorbent 1815 (comprising a mixture of one or more NaCl, $Na_2CO_3$, $Na_2SO_4$, $NaNO_3$, $CaCl_2$, $CaSO_4$, $CaCO_3$, $Ca(NO_3)_2$ $MgCl_2$, $MgCO_3$, $MgSO_4$, and $Mg(NO3)_2$, depending on the compounds used in the reactant used, as discussed below) can be added to the flue gas stream 1805. For example, the dry residue reaction section 1760 may contain a reactant 1820, such as $NaHCO_3$, $NaHCO_3 \cdot Na_2CO_3 \cdot 2(H_2O)$, $CaCO_3$, $Ca(OH)_2$, and $Mg(OH)_2$; which reacts with the NOx, SOx, $Cl_2$, and HCl to form NaCl, $Na_2CO_3$, $Na_2SO_3$, $Na_2SO_4$, $NaNO_3$, $CaCl_2$, $CaCO_3$, $CaSO_4$, $Ca(NO_3)_2$, $MgCl_2$, $Mg(NO3)_2$ and $MgSO_4$. The reaction section flue gas stream 1825 has a less NOx, HCl, $Cl_2$, and SOx compared to the incoming flue gas stream 1805. The reaction section flue gas stream 1825 consists essentially of one or more of $H_2O$, $CO_2$, $N_2$, $O_2$, NaCl, $Na_2CO_3$, $Na_2SO_4$, $NaNO_3$, $CaCl_2$, $CaCO_3$, $CaSO_4$, $Ca(NO_3)_2$, $MgCl_2$, $MgCO_3$, $MgSO_4$, $Mg(NO_3)_2$, NOx, $Cl_2$, dioxins, and furans.

The reaction section flue gas stream 1825 is cooled with a quench stream 1830 comprising air, and/or water, and/or quenched flue gas. The temperature of the reaction section flue gas stream 1825 is typically reduced from 200-400° C. with a pressure of −4 kPa(g) to 50 kPa(g) to 150-350° C. with a pressure of −4 kPa(g) to 50 kPa(g). The quenched reaction section flue gas stream 1825 is sent to the filtration section 1765 for removal of the NaCl, $Na_2CO_3$, $Na_2SO_4$, $NaNO_3$, $CaCl_2$, $CaCO_3$, $CaSO_4$, $Ca(NO_3)_2$, $MgCl_2$, $MgCO_3$, $MgSO_4$ and $Mg(NO_3)_2$. The inlet temperature of the filtration section 1765 is typically in the range of 150-350° C. with a pressure of −5 kPa(g) to 50 kPa(g). The outlet temperature is typically in the range of 150-350° C. with a pressure of −5 kPa(g) to 50 kPa(g). The filtration section 1765 comprises a bag filter, a ceramic filter, or an electrostatic precipitator. An instrument air purge or high voltage DC 1835 is introduced into the filtration section 1765 to purge the retained material from the filter. Dry residue stream 1840 comprising one or more of NaCl, $Na_2CO_3$, $Na_2SO_4$, $NaNO_3$, $CaCl_2$, $CaCO_3$, $CaSO_4$, $Ca(NO_3)_2$, $MgCl_2$, $MgCO_3$, $Mg(NO_3)_2$, and $MgSO_4$ exits the filtration section 1765. The filtered flue gas 1845 consists essentially of one or more of $H_2O$, $CO_2$, $N_2$, $O_2$, NOx, dioxins, and furans.

If NOx is present in the filtered flue gas 1845, the filtered flue gas 1845 is sent to the optional NOx removal section 1770 to remove NOx as discussed above. The inlet temperature of the NOx removal section 1770 is typically in the range of 150-300° C. with a pressure of −6 kPa(g) to 50 kPa(g). The outlet temperature is typically in the range of 200-350° C. with a pressure of −6 kPa(g) to 50 kPa(g). For example, the NOx removal section 1770 can be a selective catalytic reduction (SCR) section in which an ammonia and/or urea stream 1850 is introduced into the SCR section where it reacts with the NOx and forms $N_2$ and $H_2O$. Any suitable SCR catalyst could be used, including but not limited to, ceramic carrier materials such as titanium oxide with active catalytic components such as oxides of base metals including $TiO_2$, $WO_3$ and $V_2O_5$, or an activated carbon based catalyst. The de-NOx outlet flue gas 1855 consists essentially of one or more of $H_2O$, $CO_2$, $N_2$, $O_2$, dioxins, and furans.

If there are any halogens present in the feed, this may result in the formation of dioxin and/or furans. These compounds must be removed before the gases can be vented to the atmosphere. If dioxins and/or furans are present in the filtered flue gas 1845 or the de-NOx outlet flue gas 1855, the filtered flue gas 1845 or the de-NOx outlet flue gas 1855 is sent to the optional dioxin-furan removal section 1775 for removal of the dioxin and/or furan. The inlet temperature of the dioxin-furan removal section 1775 is typically in the range of 150-250° C. with a pressure of −7 kPa(g) to 50 kPa(g). The outlet temperature is typically in the range of 150-250° C. with a pressure of −7 kPa(g) to 50 kPa(g). The dioxin and furans can be removed using a catalyst, or by co-injecting activated carbon. With the catalyst, the dioxin and furans react the catalyst, such as a catalyst containing e.g., $TiO_2$, $WO_3$ and $V_2O_5$, to form trace amounts of $CO_2$, $H_2O$, and HCl. In the case of the activated carbon, it would be co-injected with the dry sorbent 1810 upstream of the dry residue reaction section 1760. The dioxins and/or furan would be adsorbed on the carbon, and removed from via dry residue stream 1840. The treated outlet flue gas 1860, consisting essentially of one or more of $H_2O$, $CO_2$, $N_2$, and $O_2$, can be vented to the atmosphere.

If the filtered flue gas 1845 does not contain NOx, dioxin, or furans, the optional NOx removal section 1770 and optional dioxin-furan removal section 1775 are not present. The filtered flue gas 1865, consisting essentially of one or more of $H_2O$, $CO_2$, $N_2$, and $O_2$, can be vented to the atmosphere.

If the filtered flue gas 1845 contains NOx, but no dioxin or furans, the optional dioxin-furan removal section 1775 is not present. The de-NOx outlet flue gas 1870, consisting essentially of one or more of $H_2O$, $CO_2$, $N_2$, and $O_2$, can be vented to the atmosphere.

If the filtered flue gas 1845 contains dioxin or furans, but not NOx, the optional NOx removal section 1770 is not present. The filtered flue gas 1845 is sent to the optional dioxin-furan removal section 1775. The treated outlet flue gas 1860, consisting essentially of one or more of $H_2O$, $CO_2$, $N_2$, and $O_2$, can be vented to the atmosphere.

Figure 16:
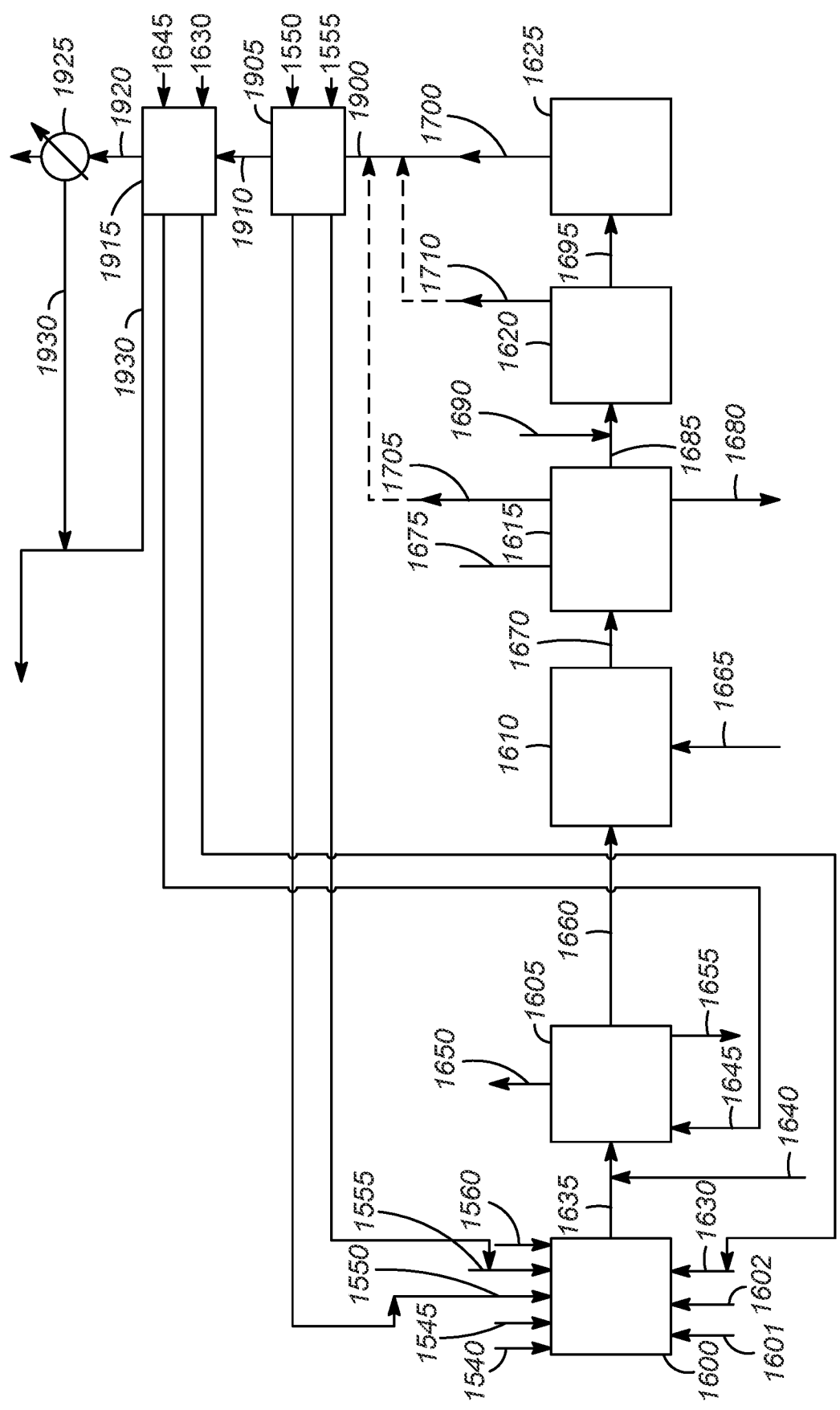
FIG. 16 illustrates another embodiment of the thermal oxidation system of FIG. 14 with improved energy recovery.

FIG. 16 illustrates an embodiment of the thermal oxidation system 1525 of FIG. 14 with improved energy recovery. In this embodiment, energy can be recovered from the exhaust vapor stream 1900 by cooling the vapor and condensing the water in the exhaust vapor stream 1900. The condensate stream can be used as process water for other parts of the process, in some cases after treatments including, but not limited to, one or more of neutralization, dearation, filtration, and degassing (thermal, pressure, and/or chemical).

The exhaust vapor stream 1900 can be sent to an optional secondary heat exchanger 1905. The exhaust vapor stream 1900 may be the treated outlet flue gas 1700 from the dioxin-furan removal section 1625, the de-NOx outlet flue gas 1710 from the NOx removal section 1620, or the scrubbed flue gas 1705 from the SOx removal section 1615. The exhaust vapor stream 1900 is sent to the second side of the secondary heat exchanger 1905.

A waste liquid stream is sent to the first side of the secondary heat exchanger 1905. There can be one or more secondary heat exchangers 1905, depending on temperature of the exhaust vapor stream 1900 and the number of process streams that are to be heated.

The waste liquid stream can be all or a portion of the spent caustic stream 1550 from the spent caustic buffer vessel 1510 as shown in FIG. 13, and/or the waste water stream 1555 from the waste water buffer vessel 1515 as shown in FIG. 13, or the waste water stream 1005 from the waste water buffer vessel 965 as shown in FIG. 8, and/or the spent caustic stream 1000 from the spent caustic buffer vessel 960 as shown in FIG. 8.

The process stream is heated by the heat exchange with the exhaust vapor stream 1900 which is cooled as a result to form a first cooled exhaust vapor stream 1910.

The heated spent caustic stream 1550, and/or the waste water stream 1555 are sent to the thermal oxidizing section 1600 of the thermal oxidation system 1525. The waste water stream 1005, and/or the spent caustic stream 1000 are sent to the thermal oxidizing section of the thermal oxidation system 975, which is similar to the thermal oxidation system 1525.

A process fluid stream is passed through the first side of a primary heat exchanger 1915. There can be one or more primary heat exchangers 1915 depending on the temperature of the exhaust vapor stream 1900 or first cooled exhaust vapor stream 1910 and the number of process fluid streams that are to be heated.

The process fluid stream can be all or a portion of a boiler feed water or oil stream 1645, a combustion air stream 1630, and an off-gas stream 678 from a polypropylene storage silo for the polypropylene product 675.

The first cooled exhaust vapor stream 1910 is sent to the second side of the primary heat exchanger 1915. Alternatively, in the absence of the secondary heat exchanger 1905, exhaust vapor stream 1900 is sent to the primary heat exchanger 1915.

The first cooled exhaust vapor stream 1910 entering the primary heat exchanger 1915 has a temperature above the dew point. The heat exchange with the process fluid stream lowers the temperature of the first cooled exhaust vapor stream 1910. In some cases, the temperature will be lowered to a temperature at or below the dew point which results in condensation of the water out of the first cooled exhaust vapor stream 1910. The resulting second cooled exhaust vapor stream 1920 can be sent to an exhaust stack and released to the atmosphere.

In other cases, the temperature will not be lowered sufficiently to condense water (any, most, or all) from the first cooled exhaust vapor stream 1910. In this case, an optional third heat exchanger 1925 can be used to lower the temperature of the second cooled exhaust vapor stream 1920 to a temperature at or below the dew point leading to the formation of water condensate. The cooling medium for the third heat exchanger 1925 can be cold/ambient air or cold water, for example.

The water condensate is recovered and exits the primary heat exchanger 1915 and/or the third heat exchanger 1925 as condensate stream 1930. Condensate stream 1930 can be sent to at least one of a feed preparation section 510 of a propane dehydrogenation complex 500 (in addition to or as replacement for make-up wash water 506, as shown in FIGS. 4 and 6), a MTBE synthesis unit 1246 of a MTBE/high purity iso-butylene derivative process unit 1245 (in addition to or as replacement for make-up wash water stream 1247 as shown in FIGS. 10A and 12A), an ETBE synthesis unit 1351 of an ETBE derivative process unit 1350 (in addition to or as replacement for make-up wash water 1354 as shown in FIGS. 10B and 12B), and an indirect alkylation reaction section 1410 of an alkylate derivative process unit 1405 (in addition to or as replacement for make-up wash water 1413 as shown in FIGS. 10C and 12C), in some cases after treatments including, but not limited to, one or more of neutralization, deaeration, filtration, and degassing (thermal, pressure, and/or chemical). The condensate stream 1930 would be sent to the MTBE synthesis unit 1246, ETBE synthesis unit 1351, or the indirect alkylation reaction section 1410 when the iso-butylene product stream 1145 originates from fluid catalytic cracking (FCC) based processes in order to remove unwanted acetone and acrylonitrile species from the iso-butylene.

The heated boiler feed water or oil stream 1645 is sent to the waste heat recovery section 1605, the combustion air stream 1630 is sent to the thermal oxidizing section 1600, and the off-gas stream 678 from the polypropylene storage silo 676 for the polypropylene product 675 is sent thermal oxidizing section of the thermal oxidation system 975.

Figure 17:
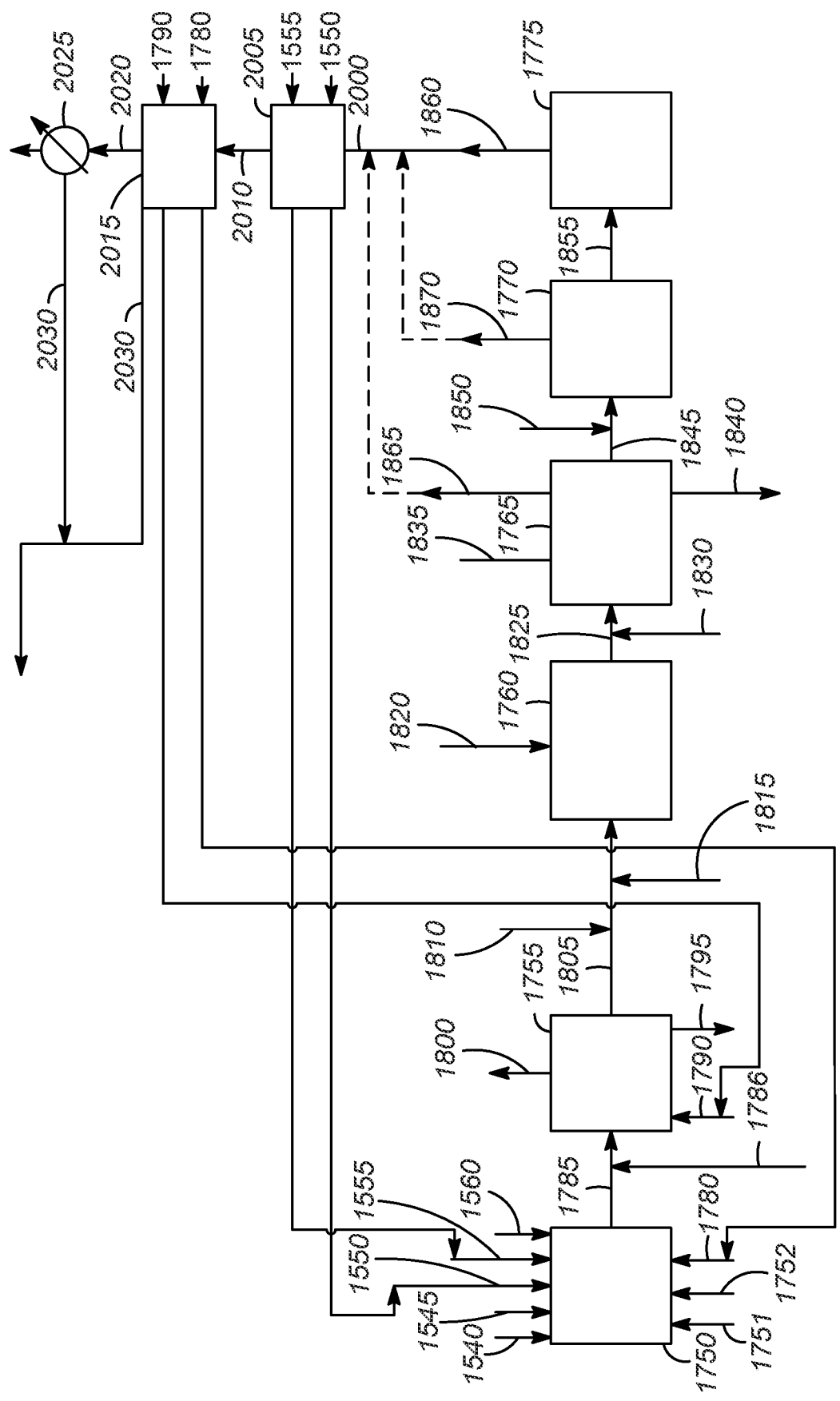
FIG. 17 illustrates another embodiment of the thermal oxidation system of FIG. 15 with improved energy recovery.

FIG. 17 illustrates an embodiment of the thermal oxidation system 1525' of FIG. 15 with improved energy recovery. In this embodiment, energy can be recovered from the exhaust vapor stream 2000 by cooling the vapor and condensing the water in the exhaust vapor stream 2000. The condensate stream can be used as process water for other parts of the process, in some cases after treatments including, but not limited to, one or more of neutralization, dearation, filtration, and degassing (thermal, pressure, chemical).

The exhaust vapor stream 2000 can be sent to an optional secondary heat exchanger 2005. The exhaust vapor stream 2000 may be the treated outlet flue gas 1860 from the dioxin-furan removal section 1775, the de-NOx outlet flue gas 1870 from the NOx removal section 1770, or the filtered flue gas 1865 from the filtration section 1765. The exhaust vapor stream 2000 is sent to the second side of the secondary heat exchanger 2005.

A waste liquid stream is sent to the first side of the secondary heat exchanger 2005. There can be one or more secondary heat exchangers 2005, depending on temperature of the exhaust vapor stream 2000 and the number of process streams that are to be heated.

The waste liquid stream can be all or a portion of the spent caustic stream 1550 from the spent caustic buffer vessel 1510 as shown in FIG. 13, and/or the waste water stream 1555 from the waste water buffer vessel 1515 as shown in FIG. 13, or the waste water stream 1005 from the waste water buffer vessel 965 as shown in FIG. 8, and/or the spent caustic stream 1000 from the spent caustic buffer vessel 960 as shown in FIG. 8.

The process stream is heated by the heat exchange with the exhaust vapor stream 2000 which is cooled as a result to form a first cooled exhaust vapor stream 2010.

The heated spent caustic stream 1550, and/or the waste water stream 1555 are sent to the thermal oxidizing section 1750 of the thermal oxidation system 1525'. The waste water stream 1005 is sent to the thermal oxidizing section of the thermal oxidation system 975, which is similar to the thermal oxidation system 1525'.

A process fluid stream is passed through the first side of a primary heat exchanger 2015. There can be one or more primary heat exchangers 2015 depending on the temperature of the exhaust vapor stream 2000 or first cooled exhaust vapor stream 2010 and the number of process fluid streams that are to be heated.

The process fluid stream can be all or a portion of a boiler feed water or oil stream 1790, a combustion air stream 1780, and an off-gas stream 678 from a polypropylene storage silo 676 for the polypropylene product 675.

The first cooled exhaust vapor stream 2010 is sent to the second side of the primary heat exchanger 2015. Alternatively, in the absence of the secondary heat exchanger 2005, exhaust vapor stream 2000 is sent to the primary heat exchanger 2015.

The first cooled exhaust vapor stream 2010 entering the primary heat exchanger 2015 has a temperature above the dew point. The heat exchange with the process fluid stream lowers the temperature of the first cooled exhaust vapor stream 2010. In some cases, the temperature will be lowered to a temperature at or below the dew point which results in condensation of the water out of the first cooled exhaust vapor stream 2010. The resulting second cooled exhaust vapor stream 2020 can be sent to an exhaust stack and released to the atmosphere.

In other cases, the temperature will not be lowered sufficiently to condense water (any, most, or all) from the first cooled exhaust vapor stream 2010. In this case, an optional third heat exchanger 2025 can be used to lower the temperature of the second cooled exhaust vapor stream 2020 to a temperature at or below the dew point leading to the formation of water condensate. The cooling medium for the third heat exchanger 2025 can be cold/ambient air or cold water, for example.

The water condensate is recovered and exits the primary heat exchanger 2015 and/or the third heat exchanger 2025 as condensate stream 2030. Condensate stream 2030 can be sent to at least one of a feed preparation section 510 of a propane dehydrogenation complex 500 (in addition to or as replacement for make-up wash water 506, as shown in FIG. 4), a MTBE synthesis unit 1246 of a MTBE/high purity iso-butylene derivative process unit 1245 (in addition to or as replacement for make-up wash water stream 1247 as shown in FIG. 10A), and an ETBE synthesis unit 1351 of an ETBE derivative process unit 1350 (in addition to or as replacement for make-up wash water 1354 as shown in FIG. 10B), and an indirect alkylation reaction section 1410 of an alkylate derivative process unit 1405 (in addition to or as replacement for make-up wash water 1413 as shown in FIG. 10C), in some cases after treatments including, but not limited to, one or more of neutralization, deaeration, filtration, and degassing (thermal, pressure, chemical). The condensate stream 2030 would be sent to the MTBE synthesis unit 1246, ETBE synthesis unit 1351, or the indirect alkylation reaction section 1410 when the iso-butylene product stream 1145 originates from fluid catalytic cracking (FCC) based processes in order to remove unwanted acetone and acrylonitrile species from the iso-butylene.

The heated boiler feed water or oil stream 1790 is sent to the waste heat recovery section 1755, the combustion air stream 1780 is sent to the thermal oxidizing section 1750, and the off-gas stream 678 from the polypropylene storage silo 676 for the polypropylene product 675 is sent thermal oxidizing section of the thermal oxidation system 975.

As used herein, the terms "unit," "zone," and "section" can refer to an area including one or more equipment items as appropriate for the type of unit, zone, or section and/or one or more sub-zones or sub-sections. Equipment items can include, but are not limited to, one or more reactors or reactor vessels, separation vessels, adsorbent chamber or chambers, distillation towers, heaters, exchangers, pipes, pumps, compressors, and controllers. Additionally, an equipment item, such as a reactor, dryer, adsorbent chamber or vessel, can further include one or more sections, sub-sections, zones, or sub-zones.

SPECIFIC EMBODIMENTS

While the following is described in conjunction with specific embodiments, it will be understood that this description is intended to illustrate and not limit the scope of the preceding description and the appended claims.

A first embodiment of the invention is a process, the process comprising dehydrogenating an alkane feed stream comprising propane, butane, or mixtures thereof in a dehydrogenation reaction zone in the presence of a dehydrogenation catalyst under dehydrogenation conditions to form a dehydrogenated product stream comprising propylene, iso-butylene, or mixtures thereof; recovering the dehydrogenated product stream; at least one of introducing a sulfidic spent caustic stream from a regenerant gas scrubbing zone into a spent caustic buffer vessel; introducing at least one of a spent solvent stream from a solvent recovery section, and a purge stream from a solvent recovery section into a hydrocarbon buffer vessel; and thermally oxidizing at least one of a spent caustic stream from the spent caustic buffer vessel, a liquid hydrocarbon stream from the hydrocarbon buffer vessel, an off-gas stream from an off-gas knockout drum, and a fuel gas stream from a fuel gas knockout drum in a thermal oxidation system. An embodiment of the invention is one, any or all of prior embodiments in this paragraph up through the first embodiment in this paragraph wherein thermally oxidizing the at least one of the spent caustic stream, the liquid hydrocarbon stream, the off-gas stream, and the fuel gas stream comprises thermally oxidizing the at least one of the spent caustic stream, the liquid hydrocarbon stream, the off-gas stream, and the fuel gas stream in a thermal oxidizing section to form a flue gas consisting essentially of at least one of $H_2O$, $Na_2CO_3$, $Na_2SO_3$, $Na_2SO_4$, $CO_2$, $N_2$, $O_2$, SOx, NOx, NaCl, HCl, $Cl_2$, dioxins, and furans; optionally recovering waste heat from the flue gas in a waste heat recovery section; removing at least one of SOx, HCl, and $Cl_2$ from the flue gas in a SOx removal section to form a de-SOx outlet flue gas consisting essentially of at least one of $H_2O$, $CO_2$, $N_2$, $O_2$, NOx, dioxins, and furans, wherein removing the at least one of SOx, HCl, and $Cl_2$ from the flue gas comprises quenching the flue gas in a quench section to form quenched flue gas after recovering the waste heat; and contacting a caustic solution or an $NH_3$ based solution with the quenched flue gas in a SOx scrubbing section to form the de-SOx outlet flue gas and a liquid stream comprising at least one of $H_2O$, $Na_2SO_3$, $Na_2SO_4$, $NaHSO_3$, $Na_2CO_3$, NaCl, $(NH_4)SO_4$, and NH4Cl; or reacting the flue gas with a reactant in an SOx reaction section to form a reaction section flue gas consisting essentially of at least one of $H_2O$, $CO_2$, $N_2$, $O_2$, NaCl, $Na_2CO_3$, $Na_2SO_4$, $NaNO_3$, $CaCl_2$), $CaSO_4$, $Ca(NO_3)_2$, $MgCl_2$, $MgCO_3$, $MgSO_4$, $Mg(NO_3)_2$, NOx, $Cl_2$, dioxins, and furans, wherein the reactant comprises at least one of $NaHCO_3$, $NaHCO_3 \cdot Na_2CO_3 \cdot 2(H_2O)$, $CaCO_3$, $Ca(OH)_2$, and $Mg(OH)_2$; and optionally filtering the reaction section flue gas in a filter section to remove at least one of NaCl, $Na_2CO_3$, $Na_2SO_4$, $NaNO_3$, $CaCl_2$), $CaCO_3$, $CaSO_4$, $Ca(NO_3)_2$, $MgCl_2$, $MgCO_3$, $MgSO_4$, and $Mg(NO_3)_2$, to form the de-SOx outlet flue gas; optionally removing NOx from the de-SOx outlet flue gas in a NOx removal section to form a de-NOx outlet flue gas consisting essentially of at least one of $H_2O$, $CO_2$, $N_2$, $O_2$, dioxins, and furans; and optionally removing dioxin, furan, or both in a dioxin-furan removal section from the de-SOx outlet flue gas or the de-NOx outlet flue gas to form a treated outlet flue gas consisting essentially of at least one of $H_2O$, $CO_2$, $N_2$, and O2. An embodiment of the invention is one, any or all of prior embodiments in this paragraph up through the first embodiment in this paragraph wherein removing NOx from the de-SOx outlet flue gas comprises reacting NOx with anhydrous $NH_3$, aqueous $NH_3$, or urea. An embodiment of the invention is one, any or all of prior embodiments in this paragraph up through the first embodiment in this paragraph further comprising cooling the dehydrogenated product stream with a solvent forming a cooled dehydrogenated product stream and a used solvent stream; and separating at least a portion of the used solvent stream into a recovered solvent stream and the spent solvent stream in the solvent recovery section; and introducing at least one of the spent solvent stream from the solvent recovery section, and the purge stream from the solvent recovery section to the hydrocarbon buffer vessel. An embodiment of the invention is one, any or all of prior embodiments in this paragraph up through the first embodiment in this paragraph further comprising cooling the dehydrogenated product stream; passing the cooled dehydrogenated product stream to an adsorbent bed to produce a purified dehydrogenated product stream; separating the purified dehydrogenated product stream into a recycle feed stream comprising unreacted propane, butane, or mixtures thereof, a recovered dehydrogenated product stream comprising the propylene, butylene, or mixtures thereof, and a net gas stream comprising hydrogen in a cryogenic separation zone; regenerating the adsorbent bed by passing at least a portion of the net gas stream from the cryogenic separation zone to the adsorbent bed and forming a regenerant gas stream; introducing a NaOH stream and the regenerant gas stream into a regenerant gas scrubbing zone to remove sulfur from the regenerant gas stream forming the sulfidic spent caustic stream and a scrubbed regenerant gas stream; introducing the sulfidic spent caustic stream to the spent caustic buffer vessel. An embodiment of the invention is one, any or all of prior embodiments in this paragraph up through the first embodiment in this paragraph further comprising at least one of passing at least a portion of the net gas stream from the cryogenic separation zone to a hydrogen purification zone forming a purified hydrogen stream and a tail gas stream; passing at least a portion of the tail gas stream to at least one of a fired heater as fuel and the fuel gas knockout drum; passing the scrubbed regenerant gas stream to at least one of the dehydrogenation reaction zone, the hydrogen purification zone, and the fuel gas knockout drum; and passing at least a portion of the net gas stream from the cryogenic separation zone to the fuel gas knockout drum. An embodiment of the invention is one, any or all of prior embodiments in this paragraph up through the first embodiment in this paragraph further comprising regenerating the dehydrogenation catalyst in a catalyst regeneration zone forming regenerated catalyst and a catalyst regeneration vent gas stream; adjusting at least one of a pressure or a temperature of the catalyst regeneration vent gas stream to form a conditioned catalyst regeneration vent gas stream; at least one of passing at least a portion of the conditioned catalyst regeneration vent gas stream to the spent caustic buffer vessel, and thermally oxidizing at least a portion of the conditioned catalyst regeneration vent gas stream; and recycling the regenerated catalyst to the dehydrogenation reaction zone. An embodiment of the invention is one, any or all of prior embodiments in this paragraph up through the first embodiment in this paragraph wherein the conditioned catalyst regeneration vent gas stream comprises chlorine gas and wherein the temperature is adjusted using a portion of the sulfidic spent caustic stream which reacts with the chlorine gas. An embodiment of the invention is one, any or all of prior embodiments in this paragraph up through the first embodiment in this paragraph wherein the conditioned catalyst regeneration vent gas stream comprises chlorine gas; and introducing the conditioned catalyst regeneration vent gas stream into the spent caustic buffer vessel; and wherein the chlorine gas in the conditioned catalyst regeneration vent gas stream reacts with sulfide, NaOH, and water in the spent sulfidic caustic stream decreasing an amount of reducing agent needed to reduce the chlorine gas compared to a regenerant vent gas treatment system using $NaHSO_3$ or $H_2O_2$. An embodiment of the invention is one, any or all of prior embodiments in this paragraph up through the first embodiment in this paragraph further comprising controlling a pressure in at least one of the spent caustic buffer vessel and the hydrocarbon buffer vessel in a push-pull system by introducing a gas stream comprising at least one of fuel gas, off-gas, or waste gas into the at least one of the spent caustic buffer vessel and the hydrocarbon buffer vessel; sending an excess gas stream to the off-gas knockout drum; separating a liquid stream from the excess gas stream in the off-gas knockout drum; and passing the liquid stream to the hydrocarbon buffer vessel. An embodiment of the invention is one, any or all of prior embodiments in this paragraph up through the first embodiment in this paragraph, further comprising passing the dehydrogenated product stream to a propylene-iso-butylene derivative process unit to form a propylene-iso-butylene derivative product comprising a propylene derivative product, an iso-butylene derivative product, or mixtures thereof, and at least one of a gaseous effluent, a hydrocarbon liquid effluent, and an aqueous effluent; recovering the propylene-iso-butylene derivative product; passing at least one of the gaseous effluent to the off-gas knockout drum, and the hydrocarbon liquid effluent to the hydrocarbon surge vessel; and optionally passing the aqueous effluent to an aqueous effluent treatment plant. An embodiment of the invention is one, any or all of prior embodiments in this paragraph up through the first embodiment in this paragraph wherein the propylene-iso-butylene derivative process unit comprises a propylene derivative process unit comprising a polymerization unit, further comprising; polymerizing the propylene in a polymerization section to form the propylene derivative product comprising polypropylene; separating the polypropylene from the propylene in a monomer recovery section using steam forming a polypropylene stream and a steamer off-gas stream; optionally extruding the polypropylene stream in an extruder section to form a polypropylene product and a tempered water bleed stream; passing at least one of the steamer off-gas stream from the monomer recovery unit to the fuel gas knockout drum, and the tempered water bleed stream from the extruder section to a waste water buffer vessel; and thermally oxidizing a waste water stream from the waste water buffer vessel. An embodiment of the invention is one, any or all of prior embodiments in this paragraph up through the first embodiment in this paragraph wherein the propylene-iso-butylene derivative process unit comprises a propylene derivative process unit comprising an acrylonitrile unit, further comprising reacting the propylene with ammonia and air in an ammoxidation reaction section to form an acrylonitrile reaction mixture; removing a cyanidic off-gas stream and a cyanidic waste water stream from the acrylonitrile mixture; separating the acrylonitrile reaction mixture into an HCN product stream and an acrylonitrile product stream; passing at least one of the cyanidic off-gas stream to the off-gas knockout drum and the cyanidic waste water stream to a waste water buffer vessel; and thermally oxidizing a waste water stream from the waste water buffer vessel. An embodiment of the invention is one, any or all of prior embodiments in this paragraph up through the first embodiment in this paragraph wherein the wherein the propylene-iso-butylene derivative process unit comprises a propylene derivative process unit comprising an oxo-alcohol unit, further comprising reacting the propylene with synthesis gas in an oxo-alcohol reaction section to form a reaction mixture comprising butyraldehyde; separating the reaction mixture into an n-butyraldehyde stream, an iso-butyraldehyde stream, and an oxo-alcohol off-gas stream; passing the oxo-alcohol off-gas stream to the off-gas knockout drum. An embodiment of the invention is one, any or all of prior embodiments in this paragraph up through the first embodiment in this paragraph wherein the wherein the propylene-iso-butylene derivative process unit comprises a propylene derivative process unit comprising an acrylic acid unit, further comprising partially oxidizing the propylene in an acrylic acid reaction section to form a reaction mixture comprising acrylic acid, acetic acid, $CO_2$, and water; quenching the reaction mixture and separating the quenched reaction mixture into a liquid stream comprising the acrylic acid and the acetic acid, a recycle gas stream, and an acrylic acid off-gas stream; separating the acrylic acid and the acetic acid from the liquid stream in a solvent extraction section to form a lean aqueous raffinate stream and a solvent rich stream comprising the acrylic acid, the acetic acid, and the solvent; fractionating the solvent rich stream in a fractionation section to form a recycle solvent stream and a crude acid stream comprising the acrylic acid and the acetic acid; purifying the crude acid stream in a product purification section to form an acrylic acid product stream, an acetic acid stream, and an acrylic acid waste organic stream; stripping the lean aqueous stream in a stripping section to form an acrylic acid waste water stream and an acid stream; passing at least one of the recycle solvent stream and the acid stream to the solvent extraction section; passing at least one of the acrylic acid off-gas stream to the off-gas knockout drum, the acrylic acid waste organic stream to the hydrocarbon surge drum, and the acrylic acid waste water stream to a waste water buffer vessel; and thermally oxidizing a waste water stream from the waste water buffer vessel. An embodiment of the invention is one, any or all of prior embodiments in this paragraph up through the first embodiment in this paragraph wherein propylene-iso-butylene derivative process unit comprises an iso-butylene derivative process unit comprising a MTBE unit, further comprising reacting the iso-butylene with natural gas in a MeOH/MTBE reaction section to produce a MTBE stream comprising methyl tert-butyl ether (MTBE), an ORU off-gas stream, a fusel oil stream, and a spent alcohol-oily water stream comprising at least one of spent alcohol and oily water; recovering the MTBE stream; optionally cracking a portion of the MTBE to form an iso-butylene stream comprising high purity iso-butylene, a MTBE light ends purge stream, and a MTBE heavies purge stream; passing at least one of the MTBE light ends purge stream to the off-gas knockout drum, the ORU off-gas stream to the off-gas knockout drum, the fusel oil stream to the hydrocarbon buffer vessel, the spent alcohol-oily water stream to the hydrocarbon buffer vessel, the MTBE light ends purge stream to the off-gas knockout drum, and the MTBE heavies purge stream to the off-gas knockout drum. An embodiment of the invention is one, any or all of prior embodiments in this paragraph up through the first embodiment in this paragraph wherein the propylene-iso-butylene derivative process unit comprises an iso-butylene derivative process unit comprising an ETBE unit, further comprising reacting the iso-butylene with natural gas in an EtOH/ETBE reaction section to produce an ETBE stream comprising ethyl tert-butyl ether (ETBE), an oxygenate containing stream, and a spent alcohol-oily water stream comprising at least one of spent alcohol and oily water; recovering the ETBE stream; optionally separating the oxygenate containing stream into an isobutane stream and an ORU off-gas stream, and recycling the isobutane stream to the dehydrogenation reaction zone, and wherein the recycled isobutane stream comprises at least a portion of the alkane feed stream; passing at least one of the spent alcohol-oily water stream to the hydrocarbon buffer vessel, and the ORU off-gas stream to the off-gas knockout drum. An embodiment of the invention is one, any or all of prior embodiments in this paragraph up through the first embodiment in this paragraph wherein the propylene-iso-butylene derivative unit comprises an iso-butylene derivative process unit comprising an alkylate unit, further comprising reacting the iso-butylene in an indirect alkylation section to form an iso-octene stream and an oxygenate containing stream; hydrogenating the iso-octene stream to form an iso-octane stream; recovering the iso-octane stream; optionally separating the oxygenate containing stream into an isobutane stream and an ORU off-gas stream, and recycling the isobutane stream to the dehydrogenation reaction zone and wherein the recycled isobutane stream comprises at least a portion of the alkane feed stream; passing the ORU off-gas stream to the off-gas knockout drum. An embodiment of the invention is one, any or all of prior embodiments in this paragraph up through the first embodiment in this paragraph wherein the alkane feed comprises butane and the product stream comprises iso-butylene, further comprising separating the butane feed stream into a butane stream comprising n-butane and an isobutane stream comprising isobutane and a C5+ heavies purge stream in a de-isobutanizer zone; passing the butane stream to the dehydrogenation zone; isomerizing the isobutane stream in a butane isomerization zone to form a butane isomerate stream; passing the butane isomerate stream to the deisobutanizer section; passing at least one of the C5+ heavies purge stream to the hydrocarbon buffer vessel and an isomerization off-gas stream from the butane isomerization zone to the off-gas knockout drum. An embodiment of the invention is one, any or all of prior embodiments in this paragraph up through the first embodiment in this paragraph wherein the alkane feed stream comprises propane and the product stream comprises propylene further comprising separating the product stream into an unreacted propane stream, a recovered product stream comprising the propylene, and a de-ethanizer off-gas stream; passing the recovered product stream to a product recovery zone; and recycling the unreacted propane stream to the dehydrogenation reaction zone; and passing the de-ethanizer off-gas stream to the fuel gas knockout drum. An embodiment of the invention is one, any or all of prior embodiments in this paragraph up through the first embodiment in this paragraph further comprising passing a process fluid stream through a first side of a primary heat exchanger, wherein the process fluid stream comprises all or a portion of at least one of a boiler feed water or oil stream, a combustion air stream, and an offgas stream from a polypropylene storage silo; passing an exhaust vapor stream from the thermal oxidation system through a second side of the primary heat exchanger, wherein the exhaust vapor stream comprises the treated outlet flue gas, the de-NOx outlet flue gas, or the de-SOx outlet flue gas; transferring heat from the exhaust vapor stream to the process fluid stream, cooling the exhaust vapor stream forming a cooled exhaust stream and heating the process fluid stream forming a heated process fluid stream, wherein the heated process fluid stream comprises at least one of a heated boiler feed water or oil stream, a heated combustion air stream, and a heated offgas stream; passing at least one of the heated boiler feed water or oil stream to the waste heat recovery section, the heated combustion air stream to the thermal oxidizing section, and the heated offgas stream to the thermal oxidizing section; and passing the cooled exhaust stream to an exhaust stack. An embodiment of the invention is one, any or all of prior embodiments in this paragraph up through the first embodiment in this paragraph further comprising passing a waste liquid stream to a first side of a secondary heat exchanger before passing the exhaust vapor stream to the primary heat exchanger to reduce a temperature of the exhaust vapor stream forming a second cooled vapor stream and to heat the waste liquid stream forming a heated waste liquid stream, wherein the waste liquid stream comprises at least one of the spent caustic stream from the spent caustic buffer vessel, and a waste water stream from a waste water buffer vessel, spent caustic buffer vessel; passing the second cooled vapor stream to the primary heat exchanger and wherein passing the exhaust vapor stream through the second side of the primary heat exchanger comprises passing the second cooled exhaust vapor stream through the second side of the primary heat exchanger; and passing the heated waste liquid stream to the thermal oxidizing section of the thermal oxidation system. An embodiment of the invention is one, any or all of prior embodiments in this paragraph up through the first embodiment in this paragraph wherein the exhaust vapor stream is cooled in the primary heat exchanger to a temperature at or below a dew point to condense water from the exhaust vapor stream, forming a first condensate stream. An embodiment of the invention is one, any or all of prior embodiments in this paragraph up through the first embodiment in this paragraph further comprising passing the first condensate stream to at least one of a feed preparation section of a propane dehydrogenation complex, a methyl tert-butyl ether (MTBE) synthesis unit of a MTBE/high purity iso-butylene derivative process unit, an ethyl tert-butyl ether (ETBE) synthesis unit of an ETBE derivative process unit, and an indirect alkylation reaction section of an alkylate derivative process unit. An embodiment of the invention is one, any or all of prior embodiments in this paragraph up through the first embodiment in this paragraph wherein the cooled exhaust vapor stream is passed to a third heat exchanger before being passed to the exhaust stack, and wherein the cooled exhaust vapor stream is further cooled in the third heat exchanger to a temperature at or below a dew point to condense water from the cooled exhaust vapor stream, forming a second condensate stream. An embodiment of the invention is one, any or all of prior embodiments in this paragraph up through the first embodiment in this paragraph further comprising passing the second condensate stream to at least one of a feed preparation section of a propane dehydrogenation complex, a methyl tert-butyl ether (MTBE) synthesis unit of a MTBE/high purity iso-butylene derivative process unit, an ethyl tert-butyl ether (ETBE) synthesis unit of an ETBE derivative process unit, and an indirect alkylation reaction section of an alkylate derivative process unit.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. An integrated propane or butane dehydrogenation and thermal oxidation process, the process comprising:
dehydrogenating an alkane feed stream comprising propane, butane, or mixtures thereof in a dehydrogenation reaction zone in the presence of a dehydrogenation catalyst under dehydrogenation conditions to form a dehydrogenated product stream comprising propylene, iso-butylene, or mixtures thereof;
recovering the dehydrogenated product stream and thereby producing a sulfidic spent caustic stream and a spent solvent stream;
at least one of:
introducing the sulfidic spent caustic stream from a regenerant gas scrubbing zone into a spent caustic buffer vessel;
introducing at least one of the spent solvent stream from a solvent recovery section, and a purge stream into a hydrocarbon buffer vessel; and
thermally oxidizing at least one of the sulfidic spent caustic stream from the spent caustic buffer vessel, a liquid hydrocarbon stream from the hydrocarbon buffer vessel,
an off-gas stream from an off-gas knockout drum, and a fuel gas stream from a fuel gas knockout drum in a thermal oxidation system.

2. The process of claim 1 wherein thermally oxidizing the at least one of the sulfidic spent caustic stream, the liquid hydrocarbon stream, the off-gas stream, and the fuel gas stream comprises:
thermally oxidizing the at least one of the sulfidic spent caustic stream, the liquid hydrocarbon stream, the off-gas stream, and the fuel gas stream in a thermal oxidizing section to form a flue gas consisting essentially of at least one of $H_2O$, $Na_2CO_3$, $Na_2SO_3$, $Na_2SO_4$, $CO_2$, $N_2$, $O_2$, SOx, NOx, NaCl, HCl, $Cl_2$, dioxins, and furans;
optionally recovering waste heat from the flue gas in a waste heat recovery section;
removing at least one of SOx, HCl, and $Cl_2$ from the flue gas in a SOx removal section to form a de-SOx outlet flue gas consisting essentially of at least one of $H_2O$, $CO_2$, $N_2$, $O_2$, NOx, dioxins, and furans, wherein removing the at least one of SOx, HCl, and $Cl_2$ from the flue gas comprises:
quenching the flue gas in a quench section to form quenched flue gas after recovering the waste heat; and
contacting a caustic solution or an $NH_3$ based solution with the quenched flue gas in a SOx scrubbing section to form the de-SOx outlet flue gas and a liquid stream comprising at least one of $H_2O$, $Na_2SO_3$, $Na_2SO_4$, NaHSO3, $Na_2CO_3$, NaCl, $(NH_4)SO_4$, and $NH_4Cl$;
or
reacting the flue gas with a reactant in an SOx reaction section to form a reaction section flue gas consisting essentially of at least one of $H_2O$, $CO_2$, $N_2$, $O_2$, NaCl, $Na_2CO_3$, $Na_2SO_4$, $NaNO_3$, $CaCl_2$, $CaSO_4$, $Ca(NO_3)_2$, $MgCl_2$, $MgCO_3$, $MgSO_4$, $Mg(NO_3)_2$, NOx, $Cl_2$, dioxins, and furans, wherein the reactant comprises at least one of $NaHCO_3$, $NaHCO_3 \cdot Na_2CO_3 \cdot 2(H_2O)$, $CaCO_3$, $Ca(OH)_2$, and $Mg(OH)_2$; and
optionally filtering the reaction section flue gas in a filter section to remove at least one of NaCl, $Na_2CO_3$, $Na_2SO_4$, $NaNO_3$, $CaCl_2$, $CaCO_3$, $CaSO_4$, $Ca(NO_3)_2$, $MgCl_2$, $MgCO_3$, $MgSO_4$, and Mg(NO3)2 to form the de-SOx outlet flue gas;
optionally removing NOx from the de-SOx outlet flue gas in a NOx removal section to form a de-NOx outlet flue gas consisting essentially of at least one of $H_2O$, $CO_2$, $N_2$, $O_2$, dioxins, and furans; and
optionally removing dioxin, furan, or both in a dioxin-furan removal section from the de-SOx outlet flue gas or the de-NOx outlet flue gas to form a treated outlet flue gas consisting essentially of at least one of $H_2O$, $CO_2$, $N_2$, and $O_2$.

3. The process of claim 1 wherein recovering the dehydrogenated product stream comprises:
cooling the dehydrogenated product stream;
passing the cooled dehydrogenated product stream to an adsorbent bed to produce a purified dehydrogenated product stream;
separating the purified dehydrogenated product stream into a recycle feed stream comprising unreacted propane, butane, or mixtures thereof, a recovered dehydrogenated product stream comprising the propylene, iso-butylene, or mixtures thereof, and a net gas stream comprising hydrogen in a cryogenic separation zone:
regenerating the adsorbent bed by passing at least a portion of the net gas stream from the cryogenic separation zone to the adsorbent bed and forming a regenerant gas stream;
introducing a NaOH stream and the regenerant gas stream into a regenerant gas scrubbing zone to remove sulfur from the regenerant gas stream, thus forming the sulfidic spent caustic stream and a scrubbed regenerant gas stream;
introducing the sulfidic spent caustic stream to the spent caustic buffer vessel; and
at least one of:
passing at least a portion of the net gas stream from the cryogenic separation zone to a hydrogen purification zone forming a purified hydrogen stream and a tail gas stream;
passing at least a portion of the tail gas stream to at least one of a fired heater as fuel and the fuel gas knockout drum;
passing the scrubbed regenerant gas stream to at least one of the dehydrogenation reaction zone, the hydrogen purification zone, and the fuel gas knockout drum; and
passing at least a portion of the net gas stream from the cryogenic separation zone to the fuel gas knockout drum.

4. The process of claim 1 further comprising:
controlling a pressure in at least one of the spent caustic buffer vessel and the hydrocarbon buffer vessel in a push-pull system by introducing a gas stream comprising at least one of fuel gas, off-gas, or waste gas into at least one of the spent caustic buffer vessel and the hydrocarbon buffer vessel;
sending an excess gas stream from the spent caustic buffer vessel or the hydrocarbon buffer vessel to the off-gas knockout drum;
separating a liquid stream from the excess gas stream in the off-gas knockout drum; and
passing the liquid stream to the hydrocarbon buffer vessel.

5. The process of claim 1, further comprising
passing the dehydrogenated product stream to a propylene-iso-butylene derivative process unit to form a propylene-iso-butylene derivative product comprising a propylene derivative product, an iso-butylene derivative product, or mixtures thereof, and at least one of a gaseous effluent, a hydrocarbon liquid effluent, and an aqueous effluent;
recovering the propylene-iso-butylene derivative product;
passing at least one of: the gaseous effluent to the off-gas knockout drum, and the hydrocarbon liquid effluent to the hydrocarbon buffer vessel; and
optionally passing the aqueous effluent to an aqueous effluent treatment plant.

6. The process of claim 5 wherein the propylene-iso-butylene derivative process unit comprises a propylene derivative process unit comprising a polymerization unit, further comprising:
polymerizing the propylene in a polymerization section to form the propylene derivative product comprising polypropylene;
separating the polypropylene from the propylene in a monomer recovery section using steam, thus forming a polypropylene stream and a steamer off-gas stream;
optionally extruding the polypropylene stream in an extruder section to form a polypropylene product and a tempered water bleed stream;
passing at least one of the steamer off-gas stream from the monomer recovery unit to the fuel gas knockout drum, and the tempered water bleed stream from the extruder section to a waste water buffer vessel; and
thermally oxidizing a waste water stream from the waste water buffer vessel.

7. The process of claim 5 wherein the propylene-iso-butylene derivative process unit comprises a propylene derivative process unit comprising an acrylonitrile unit, further comprising:
reacting the propylene with ammonia and air in an ammoxidation reaction section to form an acrylonitrile reaction mixture;
removing a cyanidic off-gas stream and a cyanidic waste water stream from the acrylonitrile reaction mixture;
separating the acrylonitrile reaction mixture into an HCN product stream and an acrylonitrile product stream;

passing at least one of the cyanidic off-gas stream to the off-gas knockout drum and the cyanidic waste water stream to a waste water buffer vessel; and thermally oxidizing a waste water stream from the waste water buffer vessel.

8. The process of claim 5 wherein the wherein the propylene-iso-butylene derivative process unit comprises a propylene derivative process unit comprising an oxo-alcohol unit, further comprising:

reacting the propylene with synthesis gas in an oxo-alcohol reaction section to form a reaction mixture comprising butyraldehyde;

separating the reaction mixture into an n-butyraldehyde stream, an iso-butyraldehyde stream, and an oxo-alcohol off-gas stream; and passing the oxo-alcohol off-gas stream to the off-gas knockout drum.

9. The process of claim 5 wherein the wherein the propylene-iso-butylene derivative process unit comprises a propylene derivative process unit comprising an acrylic acid unit, further comprising:

partially oxidizing the propylene in an acrylic acid reaction section to form a reaction mixture comprising acrylic acid, acetic acid, CO2, and water;

quenching the reaction mixture and separating the quenched reaction mixture into a liquid stream comprising the acrylic acid and the acetic acid, a recycle gas stream, and an acrylic acid off-gas stream;

separating the acrylic acid and the acetic acid from the liquid stream in a solvent extraction section to form a lean aqueous raffinate stream and a solvent rich stream comprising the acrylic acid, the acetic acid, and the solvent;

fractionating the solvent rich stream in a fractionation section to form a recycle solvent stream and a crude acid stream comprising the acrylic acid and the acetic acid;

purifying the crude acid stream in a product purification section to form an acrylic acid product stream, an acetic acid stream, and an acrylic acid waste organic stream;

stripping the lean aqueous raffinate stream in a stripping section to form an acrylic acid waste water stream and an acid stream;

passing at least one of the recycle solvent stream and the acid stream to the solvent extraction section;

passing at least one of the acrylic acid off-gas stream to the off-gas knockout drum, the acrylic acid waste organic stream to the hydrocarbon buffer vessel, and the acrylic acid waste water stream to a waste water buffer vessel; and thermally oxidizing a waste water stream from the waste water buffer vessel.

10. The process of claim 5 wherein propylene-iso-butylene derivative process unit comprises an iso-butylene derivative process unit comprising a MTBE unit, further comprising:

reacting the iso-butylene with natural gas in a MeOH/MTBE reaction section to produce a MTBE stream comprising methyl tert-butyl ether (MTBE), an ORU off-gas stream, a fusel oil stream, and a spent alcohol-oily water stream comprising at least one of spent alcohol and oily water;

recovering the MTBE stream;

optionally cracking a portion of the MTBE to form an iso-butylene stream comprising high purity iso-butylene, a MTBE light ends purge stream, and a MTBE heavies purge stream; and passing at least one of the MTBE light ends purge stream to the off-gas knockout drum, the ORU off-gas stream to the off-gas knockout drum, the fusel oil stream to the hydrocarbon buffer vessel, the spent alcohol-oily water stream to the hydrocarbon buffer vessel, the MTBE light ends purge stream to the off-gas knockout drum, and the MTBE heavies purge stream to the off-gas knockout drum.

11. The process of claim 5 wherein the propylene-iso-butylene derivative process unit comprises an iso-butylene derivative process unit comprising an ETBE unit, further comprising:

reacting the iso-butylene with natural gas in an EtOH/ETBE reaction section to produce an ETBE stream comprising ethyl tert-butyl ether (ETBE), an oxygenate containing stream, and a spent alcohol-oily water stream comprising at least one of spent alcohol and oily water;

recovering the ETBE stream;

optionally separating the oxygenate containing stream into an isobutane stream and an ORU off-gas stream, and recycling the isobutane stream to the dehydrogenation reaction zone, and wherein the recycled isobutane stream comprises at least a portion of the alkane feed stream; and passing at least one of the spent alcohol-oily water stream to the hydrocarbon buffer vessel, and the ORU off-gas stream to the off-gas knockout drum.

12. The process of claim 5 wherein the propylene-iso-butylene derivative unit comprises an iso-butylene derivative process unit comprising an alkylate unit, further comprising:

reacting the iso-butylene in an indirect alkylation section to form an iso-octene stream and an oxygenate containing stream;

hydrogenating the iso-octene stream to form an iso-octane stream;

recovering the iso-octane stream;

optionally separating the oxygenate containing stream into an isobutane stream and an ORU off-gas stream, and recycling the isobutane stream to the dehydrogenation reaction zone and wherein the recycled isobutane stream comprises at least a portion of the alkane feed stream; and optionally passing the ORU off-gas stream to the off-gas knockout drum.

13. The process of claim 1 wherein the alkane feed comprises butane and the product stream comprises iso-butylene, further comprising:

separating the butane feed stream into a butane stream comprising n-butane, and an isobutane stream comprising isobutane, and a C5+ heavies purge stream in a de-isobutanizer zone;

passing the butane stream to the dehydrogenation zone;

isomerizing the isobutane stream in a butane isomerization zone to form a butane isomerate stream;

passing the butane isomerate stream to the deisobutanizer zone; and passing at least one of the C5+ heavies purge stream to the hydrocarbon buffer vessel and an isomerization off-gas stream from the butane isomerization zone to the off-gas knockout drum.

14. The process of claim 1 wherein the alkane feed stream comprises propane and the dehydrogenated product stream comprises propylene, and further comprising: separating the dehydrogenated product stream into an unreacted propane stream, a recovered product stream comprising the propylene, and a de-ethanizer off-gas stream; passing the recovered product stream to a product recovery zone; recycling the unreacted propane stream to the dehydrogenation reaction zone; and passing the de-ethanizer off-gas stream to the fuel gas knockout drum.

15. The process of claim 2 further comprising:
passing a process fluid stream through a first side of a primary heat
exchanger, wherein the process fluid stream comprises all or a portion of at least one of a boiler feed water or oil stream, a combustion air stream, and an offgas stream from a polypropylene storage silo;
passing an exhaust vapor stream from the thermal oxidation system through a second side of the primary heat exchanger, wherein the exhaust vapor stream comprises the treated outlet flue gas, the de-NOx outlet flue gas, or the de-SOx outlet flue gas;
transferring heat from the exhaust vapor stream to the process fluid stream, cooling the exhaust vapor stream forming a cooled exhaust stream and heating the process fluid stream forming a heated process fluid stream, wherein the heated process fluid stream comprises at least one of a heated boiler feed water or oil stream, a heated combustion air stream, and a heated off gas stream;
passing at least one of: the heated boiler feed water or oil stream to the waste heat recovery section, the heated combustion air stream to the thermal oxidizing section, and the heated offgas stream to the thermal oxidizing section; and
passing the cooled exhaust stream to an exhaust stack.

16. The process of claim 15 further comprising:
before passing the exhaust vapor stream to the primary heat exchanger, passing a waste liquid stream to a first side of a secondary heat exchanger and the exhaust vapor stream to a second side of the secondary heat exchanger to reduce a temperature of the exhaust vapor stream forming a second cooled vapor stream and to heat the waste liquid stream forming a heated waste liquid stream, wherein the waste liquid stream comprises at least one of the spent caustic stream from the spent caustic buffer vessel, and a waste water stream from a waste water buffer vessel;
passing the second cooled vapor stream to the primary heat exchanger and wherein passing the exhaust vapor stream through the second side of the primary heat exchanger comprises passing the second cooled exhaust vapor stream through the second side of the primary heat exchanger; and
passing the heated waste liquid stream to the thermal oxidizing section of the thermal oxidation system.

17. The process of claim 15 wherein the exhaust vapor stream is cooled in the primary heat exchanger to a temperature at or below a dew point to condense water from the exhaust vapor stream, forming a first condensate stream.

18. The process of claim 17 further comprising:
passing the first condensate stream to at least one of a feed preparation section of a propane dehydrogenation complex, a methyl tert-butyl ether (MTBE) synthesis unit of a MTBE/high purity iso-butylene derivative process unit, an ethyl tert-butyl ether (ETBE) synthesis unit of an ETBE derivative process unit, and an indirect alkylation reaction section of an alkylate derivative process unit.

19. The process of claim 17 wherein the cooled exhaust vapor stream is passed to a third heat exchanger before being passed to the exhaust stack, and wherein the cooled exhaust vapor stream is further cooled in the third heat exchanger to a temperature at or below a dew point to condense water from the cooled exhaust vapor stream, forming a second condensate stream.

20. The process of claim 19 further comprising:
passing the second condensate stream to at least one of a feed preparation section of a propane dehydrogenation complex, a methyl tert-butyl ether (MTBE) synthesis unit of a MTBE/high purity iso-butylene derivative process unit, an ethyl tert-butyl ether (ETBE) synthesis unit of an ETBE derivative process unit, and an indirect alkylation reaction section of an alkylate derivative process unit.

* * * * *